US012590324B2

(12) United States Patent
Stemple et al.

(10) Patent No.: US 12,590,324 B2
(45) Date of Patent: Mar. 31, 2026

(54) COMPOSITIONS AND METHODS FOR TEMPLATE-FREE GEOMETRIC ENZYMATIC NUCLEIC ACID SYNTHESIS

(71) Applicant: CAMENA BIOSCIENCE LIMITED, Essex (GB)

(72) Inventors: Derek L. Stemple, Newton, MA (US); Andrew G. Fraser, Toronto (CA); Sylwia Mankowska, Essex (GB); Neil Bell, Essex (GB)

(73) Assignee: CAMENA BIOSCIENCE LIMITED, Little Chesterford (GB)

( * ) Notice: Subject to any disclaimer, the term of this patent is extended or adjusted under 35 U.S.C. 154(b) by 1204 days.

(21) Appl. No.: 17/422,967

(22) PCT Filed: Jan. 13, 2020

(86) PCT No.: PCT/US2020/013331
§ 371 (c)(1),
(2) Date: Jul. 14, 2021

(87) PCT Pub. No.: WO2020/150143
PCT Pub. Date: Jul. 23, 2020

(65) Prior Publication Data
US 2022/0145346 A1 May 12, 2022

Related U.S. Application Data

(60) Provisional application No. 62/792,341, filed on Jan. 14, 2019.

(51) Int. Cl.
*C07H 21/00* (2006.01)
*C12P 19/34* (2006.01)

(52) U.S. Cl.
CPC .............. *C12P 19/34* (2013.01); *C07H 21/00* (2013.01)

(58) Field of Classification Search
None
See application file for complete search history.

(56) References Cited

U.S. PATENT DOCUMENTS

| | | | |
|---|---|---|---|
| 5,114,839 A | 5/1992 | Blocker | |
| 5,602,000 A | 2/1997 | Hyman | |
| 6,479,262 B1 | 11/2002 | Delagrave | |
| 6,521,427 B1 | 2/2003 | Evans | |
| 6,635,453 B2 | 10/2003 | Delagrave et al. | |
| 6,670,127 B2 | 12/2003 | Evans | |
| 8,034,923 B1 | 10/2011 | Benner et al. | |
| 9,068,209 B2 | 6/2015 | Coope et al. | |
| 9,410,887 B2 | 8/2016 | Walavalkar et al. | |
| 11,667,941 B2 | 6/2023 | Stemple et al. | |
| 2004/0038253 A1* | 2/2004 | Nagamine ............ | C12Q 1/6844 435/6.12 |
| 2004/0091920 A1 | 5/2004 | Tsuji et al. | |
| 2011/0104785 A1 | 5/2011 | Vaidyanathan et al. | |

| | | |
|---|---|---|
| 2012/0190728 A1 | 7/2012 | Bennett et al. |
| 2014/0363851 A1 | 12/2014 | Efcavitch et al. |
| 2015/0376602 A1 | 12/2015 | Jacobson et al. |
| 2016/0108382 A1 | 4/2016 | Efcavitch et al. |
| 2019/0169665 A1 | 6/2019 | Pedersen et al. |
| 2021/0087600 A1 | 3/2021 | Stemple et al. |

FOREIGN PATENT DOCUMENTS

| | | |
|---|---|---|
| DE | 4343591 A1 | 6/1995 |
| EP | 2711370 A1 | 3/2014 |
| EP | 3115462 A1 | 1/2017 |
| EP | 2711370 B1 | 1/2018 |
| WO | WO-8911211 A2 | 11/1989 |
| WO | WO-9517413 A1 | 6/1995 |
| WO | WO-9914318 A1 | 3/1999 |
| WO | WO-0029616 A1 | 5/2000 |
| WO | WO-0049142 A1 | 8/2000 |
| WO | WO-0188173 A2 | 11/2001 |
| WO | WO-2005051174 A2 | 6/2005 |
| WO | WO-2006086669 A2 | 8/2006 |
| WO | WO-2011056866 A2 | 5/2011 |
| WO | WO-2012078312 A2 | 6/2012 |
| WO | WO-2012101151 A1 | 8/2012 |
| WO | WO-2013012674 A1 | 1/2013 |
| WO | WO-2013016694 A2 | 1/2013 |
| WO | WO-2013036810 A1 | 3/2013 |
| WO | WO-2013142389 A1 | 9/2013 |
| WO | WO-2015195257 A1 | 12/2015 |
| WO | WO-2016128731 A1 | 8/2016 |
| WO | WO-2018050722 A1 | 3/2018 |
| WO | WO-2018152323 A1 | 8/2018 |
| WO | WO-2018175997 A1 | 9/2018 |
| WO | WO-2019051470 A1 | 3/2019 |
| WO | WO-2019073072 A1 | 4/2019 |
| WO | WO-2019094651 A1 | 5/2019 |
| WO | WO-2019140353 A1 | 7/2019 |

(Continued)

OTHER PUBLICATIONS

Beskin et al. "On the mechanism of the modular primer effect" Nucleic Acids Research (1995); 23(15):2881-2885.

Davies et al. "Three-Dimensional Structure of the Tn5 Synaptic Complex Transposition Intermediate" Science (2000); 289(5476):77-85.

England, T. E., "Dinucleoside pyrophosphate are substrates for T4-induced RNA ligase" Proc Natl Acad Sci USA (1977); 74:4839-4842.

GenBank Accession No. L29345 "Aequorea victoria green-fluorescent protein (GFP) mRNA, complete cds" dated Dec. 30, 1994, 2 pages.

Hao, J. et al. "A mild and reliable method to label enveloped virus with quantum dots by copper-free click chemistry" Anal Chem (2012); 84:8364-8370.

(Continued)

*Primary Examiner* — Katherine D Salmon
(74) *Attorney, Agent, or Firm* — WILSON SONSINI GOODRICH & ROSATI

(57) ABSTRACT

Disclosed are compositions and methods for template-free nucleic acid synthesis using N-mers and/or anchor primers that comprise at least one XNA or a combination of RNA and DNA.

20 Claims, 17 Drawing Sheets

Specification includes a Sequence Listing.

(56) References Cited

FOREIGN PATENT DOCUMENTS

| WO | WO-2020150143 A2 | 7/2020 |
| WO | WO-2020185967 A1 | 9/2020 |
| WO | WO-2021055962 A1 | 3/2021 |
| WO | WO-2022109389 A1 | 5/2022 |

OTHER PUBLICATIONS

Kelly, G. "Studies on Nucleic Acids: 1. The Use of T4 RNA Ligase to Join Chemically Synthesized Oligo Deoxyribonucleotides II. Chemical Synthesis and Purification of Phasing Primers" Ph.D. Thesis, Purdue University. Part I only, (1983); 122 pages.

Kotler et al. "DNA sequencing: modular primers assembled from a library of hexamers or pentamers" Proceedings of the National Academy of Sciences (1993); 90(9):4241-4245.

Levin "Homogeneous *Escherichia coli* endonuclease IV. Characterization of an enzyme that recognizes oxidative damage in DNA" J Biol Chem (1988); 263:8066-8071.

Lindahl "DNA N-glycosidases: properties of uracil-DNA glycosidase from *Escherichia coli*" J Biol Chem (1977); 252:3286-3294.

Mathews et al. "Photo-cleavable nucleotides for primer free enzyme mediated DNA synthesis" Organic & Biomolecular Chemistry (2016); 14(35):8278-8288.

Okuda et al. "Use of Baby Spinach and Broccoli for imaging of structured cellular RNAs" Nucleic Acids Research (2017); 45:1404-1415.

Paige et al. "RNA mimics of green fluorescent protein" Science (2011); 333:642-646.

Robson et al. "Isolation of cDNA clones encoding a human apurinic/apyrimidinic endonuclease that corrects DNA repair and mutagenesis defects in *E. coli* xth (exonuclease III) mutants" Nucleic Acids Research (1991); 19:5519-5523.

Torchia et al. "Archaeal RNA ligase is a homodimeric protein that catalyzes intramolecular ligation of single-stranded RNA and DNA" Nucleic Acids Research (2008); 36:6218-6227.

Abe, Takayuki. et al. Specific inhibition of influenza virus RNA polymerase and nucleoprotein gene expression by circular dumbbell RNA/DNA chimeric oligonucleotides containing antisense phosphodiester oligonucleotides. FEBS letters 425(1):91-96 (1998).

Andrade, Paula. et al. Limited terminal transferase in human DNA polymerase μ defines the required balance between accuracy and efficiency in NHEJ. Proceedings of the National Academy of Sciences 106(38):16203-16208 (2009).

Berdis, Anthony J, and David McCutcheon. The use of non-natural nucleotides to probe template-independent DNA synthesis. Chembiochem 8(12):1399-1408 (2007).

Chen, Yang. et al. Selection of DNA aptamers for the development of light-up biosensor to detect Pb(II). Sensors and Actuators B Chemical 254:214-221 (2018).

De Falco, Mariarosaria. et al. The DNA primase of Sulfolobus solfataricus is activated by substrates containing a thymine-rich bubble and has a 3'-terminal nucleotidyl-transferase activity. Nucleic acids research 32(17):5223-5230 (2004).

Den Dunnen, Johan T. et al. HGVS recommendations for the description of sequence variants: 2016 update. Human mutation 37(6):564-569 (2016).

Den Dunnen, Johan T., and Stylianos E. Antonarakis. Mutation nomenclature extensions and suggestions to describe complex mutations: a discussion. Human mutation 15(1):7-12 (2000).

Gill, Sukhvinder. et al. A highly divergent archaeo-eukaryotic primase from the Thermococcus nautilus plasmid, pTN2. Nucleic Acids Res 42(6):3707-3719 (2014).

Hamedirad, Mohammad. et al. Highly efficient single-pot scarless Golden Gate assembly. ACS synthetic biology 8(5):1047-1054 (2019).

Horning, David P, and Gerald F. Joyce. Amplification of RNA by an RNA polymerase ribozyme. Proceedings of the National Academy of Sciences 113(35):9786-9791 (2016).

Ilgu, Muslum, and Marit Nilsen-Hamilton. Aptamers in analytics. The Analyst 141(5):1551-1568 (2016).

Kou, Ruqin. et al. Benefits and Challenges with Applying Unique Molecular Identifiers in Next Generation Sequencing to Detect Low Frequency Mutations. PloS one 11(1):e0146638, 1-15 (2016).

Lao-Sirieix, Si-houy, and Stephen D. Bell. The heterodimeric primase of the hyperthermophilic archaeon Sulfolobus solfataricus possesses DNA and RNA primase, polymerase and 3'-terminal nucleotidyl transferase activities. Journal of molecular biology 344(5):1251-1263 (2004).

Lao-Sirieix, Si-houy. et al. The promiscuous primase. Trends in Genetics 21(10):568-572 (2005).

Lehman, I.R. and A.L. Nussbaum. The Deoxyribonucleases of *Escherichia coli*. V. On the Specificity of Exonuclease I Phosphodiesterase). The Journal of biological chemistry 239:2628-2636 (1964).

Kotler, Lev. et al. DNA sequencing: Modular primers assembled from a library of hexamers or pentamers. Biochemistry Communicated by Charles R. Cantor (1993) [retrieved on May 4, 2020]. Available at URL: https://www.pnas.org/content/pnas/90/9 /4241.full.pdf pp. 421-425 [abstract].

Levin, Joshua D. et al. Homogeneous *Escherichia coli* endonuclease IV. Characterization of an enzyme that recognizes oxidative damage in DNA. Journal of Biological Chemistry 263(17):8066-8071 (1988).

Litosh, Vladislav A. et al. Improved nucleotide selectivity and termination of 3'-OH unblocked reversible terminators by molecular tuning of 2-nitrobenzyl alkylated HOMedU triphosphates. Nucleic Acids Res 39(6):e39, 1-13 (2011).

Little, John W. Lambda exonuclease. Gene amplification and analysis 2:135-145 (1981).

Mathews, Anu Stella. et al. Photo-cleavable nucleotides for primer free enzyme mediated DNA synthesis. Organic & Biomolecular Chemistry 14(35):8278-8288 (2016).

Mitra, Robi D, and George M. Church. In situ localized amplification and contact replication of many individual DNA molecules. Nucleic Acids Research 27(24):e34-e39 (1999).

Moon, Andrea F. et al. The X family portrait: structural insights into biological functions of X family polymerases. DNA repair 6(12):1709-1725 (2007).

Okuda, Maho. et al. Use of Baby Spinach and Broccoli for imaging of structured cellular RNAs. Nucleic acids research 45(3):1404-1415 (2017).

Paige, Jeremy S, et al. RNA Mimics of Green Fluorescent Protein. Science 333(6042):642-646 (2011).

PCT/US2018/018365 International Preliminary Report on Patentability dated Aug. 29, 2019.

PCT/US2018/018365 International Search Report and Written Opinion dated Apr. 11, 2018.

PCT/US2018/050398 International Preliminary Report on Patentability dated Mar. 26, 2020.

PCT/US2018/050398 International Search Report and Written Opinion dated Nov. 29, 2018.

PCT/US2019/013441 International Preliminary Report on Patentability dated Jul. 23, 2020.

PCT/US2019/013441 International Search Report and Written Opinion dated Apr. 6, 2019.

PCT/US2020/013331 International Preliminary Report on Patentability dated Jul. 29, 2021.

PCT/US2020/013331 International Search Report and Written Opinion dated Jul. 13, 2020.

PCT/US2020/051838 International Preliminary report on Patentability dated Mar. 31, 2022.

PCT/US2020/051838 International Search Report and Witten Opinion dated Dec. 23, 2020.

PCT/US2021/060328 International Preliminary Report on Patentability dated Jun. 1, 2023.

PCT/US2021/060328 International Search Report and Written Opinion dated Mar. 14, 2022.

Pinheiro, Vitor B. et al. Synthetic genetic polymers capable of heredity and evolution. Science 336(6079):341-344 (2012).

Polymerase chain reaction. Wikipedia the Free Encylopedia, [retrieved on Jan. 13, 2024]. Available at URL:https://en.wikipedia.org/wiki/Polymerase_chain_reaction pp. 1-13.

(56) References Cited

OTHER PUBLICATIONS

Potapov, Vladimir/ et al. Comprehensive profiling of four base overhang ligation fidelity by T4 DNA ligase and application to DNA assembly. ACS synthetic biology 7(11):2665-2674 (2018).

Ramadan, Kristijan/ et al. Human DNA polymerase λ possesses terminal deoxyribonucleotidyl transferase activity and can elongate RNA primers: implications for novel functions. Journal of molecular biology 328(1):63-72 (2003).

Ranjith-Kumar, C. T. et al. Terminal nucleotidyl transferase activity of recombinant Flaviviridae RNA-dependent RNA polymerases: implication for viral RNA synthesis. Journal of virology 75(18):8615-8623 (2001).

Recombinase polymerase amplification. Wikipedia the free Encyclopedia, [retrieved on Jan. 13, 2024]. Available at URL:https://en.wikipedia.org/wiki/Recombinase_polymerase_amplification pp. 1-4.

Robson, Craig N, and Ian D. Hickson. Isolation of cDNA clones encoding a human apurini/apyrimidinic endonuclease that corects DNA repair and mutagenisis defects in *E. coli* xth (exonuclease III) mutants. Nucleic acids research 19(20):5519-5523 (1991).

Rohland, Nadin, and David Reich. Cost-effective, High-throughput DNA Sequencing Libraries for Multiplexed Target Capture. Genome Research 22(5):939-946 (2012).

Romain, Felix/ et al. Conferring a template-dependent polymerase activity to terminal deoxynucleotidyltransferase by mutations in the Loop1 region. Nucleic acids research 37(14):4642-4656 (2009).

Sanger, F, and A.R. Coulson. A rapid method for determining sequences in DNA by primed synthesis with DNA polymerase. J Mol Biol 94(3):441-448 (1975).

Sawano, Asako, and Atsushi Miyawaki. Directed evolution of green fluorescent protein by a new versatile PCR strategy for site-directed and semi-random mutagenesis. Nucleic acids research 28(16):e78, 1-7 (2000).

Sefah, Kwame. et al. In vitro selection with artificial expanded genetic information systems. Proceedings of the National Academy of Sciences 111(4):1449-1454 (2014).

Torchia, Christopher. et al. Archaeal RNA ligase is a homodimeric protein that catalyzes intramolecular ligation of single-stranded RNA and DNA. Nucleic Acids Research 36(19):6218-6227 (2008).

Tsien, Roger Y. The green fluorescent protein. Annual review of biochemistry 67(1):509-544 (1998).

U.S. Appl. No. 16/961,465 Notice of Allowance dated Jan. 25, 2023.

U.S. Appl. No. 16/961,465 Office Action dated Apr. 29, 2022.

U.S. Appl. No. 16/961,465 Restriction Requirement dated Aug. 11, 2021.

U.S. Appl. No. 17/761,696 Office Action dated Aug. 14, 2025.

Potapov, Vladimir. et al. Optimization of Golden Gate assembly through application of ligation sequence-dependent fidelity and bias profiling. BioRxiv preprint (2018):322297, 1-26 (2018).

Wang, Hongyan. et al. Selection and characterization of DNA aptamers for the development of light-up biosensor to detect Cd(II). Talanta 154:498-503 (2016).

Wang, Zhaowei. et al. Characterization of a nodavirus replicase revealed a de novo initiation mechanism of RNA synthesis and terminal nucleotidyltransferase activity. Journal of Biological Chemistry 288(43):30785-30801 (2013).

Wu, Wenzhe. et al. Flock house virus RNA polymerase initiates RNA synthesis de novo and possesses a terminal nucleotidyl transferase activity. PLoS One 9(1):e86876, 1-11 (2014).

Yamashita, Tatsuya. et al. RNA-dependent RNA polymerase activity of the soluble recombinant hepatitis C virus NS5B protein truncated at the C-terminal region. Journal of Biological Chemistry 273(25):15479-15486 (1998).

Yamtich, Jennifer, and Joann B. Sweasy. DNA polymerase family X: function, structure, and cellular roles. Biochimica et Biophysica Acta (BBA)-Proteins and Proteomics 1804(5):1136-1150 (2010).

Zuo, Zhongfeng. et al. Strand annealing and terminal transferase activities of a B-family DNA polymerase. Biochemistry 50(23):5379-5390 (2011).

* cited by examiner

>L29345.1 Aequorea victoria green-fluorescent protein (GFP) mRNA, complete cds

SEQ ID NO: 19

FIG. 3A

Plate Set "a" (SEQ ID NOs: 20-41)

| | |
|---|---|
| 1aA1 | TACACACGAATAAAAGATAAC |
| 1aA2 | ACTTTTCACTGGAGTTGTCCC |
| 1aA3 | CGATGTTAATGGGCAAAAATT |
| 1aA4 | AAGTGATGCAACATACGGAAA |
| 1aA5 | CACTACTGGGAAGCTACCTGT |
| 1aA6 | TACTTCTCTTTATGGTGTTCA |
| 1aA7 | TCATATGAAACAGCATGACTT |
| 1aA8 | AGGTTATGTACAGGAAGAAC |
| 1aA9 | GAACTACAAGACACGTGCTGA |
| 1aA10 | CTTTTGTTAATAGAATCGAGTT |
| 1aA11 | AGATGGAAACATTCTTGGACA |
| 1aA12 | CTTCACATAATGTATACATCAT |
| 1aB1 | AATCAAAGTTAACTTCAAAAT |
| 1aB2 | AAGCGTTCAATTAGCAGACCA |
| 1aB3 | TGGGGATGGCCCTGTCCTTTT |
| 1aB4 | CACACAATCTGCCCTTTCCAA |
| 1aB5 | TCACATGATCCTTTCTGAGTT |
| 1aB6 | ACAATGGCATGGATGAACTATA |
| 1aB7 | AATTCACACTAAAGTGTCCGA |
| 1aB8 | TTCCTGGTTAAATTCAGGCTG |
| 1aB9 | AGATTCATTAAAATTTTATGA |
| 1aB10 | TAGGGGTCTATTTTCTTATTTA |

Plate Set "b" (SEQ ID NOs: 42-63)

| | |
|---|---|
| 1bA1 | AAAGATGGTAAAGGAGAGA |
| 1bA2 | AATTCTTGTTGAATTAGATGG |
| 1bA3 | CTCTGTCAGTGGAGAGGGTGA |
| 1bA4 | ACTTACCCTTAAATTTATTTG |
| 1bA5 | TCCATGGCCAACACTTGTCAC |
| 1bA6 | ATGCTTTTCAAGATACCCAGA |
| 1bA7 | TTTCAAGAGTGCCATGCCCGA |
| 1bA8 | TATATTTTACAAAGATGACGG |
| 1bA9 | ACTCAATTTGAAGGTGATAAC |
| 1bA10 | AAAGGTATTTGATTCAACTATAA |
| 1bA11 | CAAAATGGAATACAAACTATAA |
| 1bA12 | GGCAGACAAGCAAAGAAATGG |
| 1bB1 | TAGACACAACATTAAAGATGG |
| 1bB2 | TTATCAACAAAATACTTCAAT |
| 1bB3 | ACCAGACAACCATTACCTGTC |
| 1bB4 | AGATCCCAACGAAAAGAGAGA |
| 1bB5 | TGTAACAGCTGCTGGGATTAC |
| 1bB6 | CAAATAAAGTCCAGACTTCC |
| 1bB7 | ACAATTACTAAAATTCTCAGGG |
| 1bB8 | AGACTTTATTTATTATATTTAT |
| 1bB9 | ATAATTTATTGATCTTATTAAA |
| 1bB10 | ATAGGCTACTGGAGTGTAT |

FIG. 3B

Plate layout and pipetting moves

Geometric Synthesis with Transposase

Internal Cy3

Locked Nucleic Acid (LNA)

FIG. 16

COMPOSITIONS AND METHODS FOR TEMPLATE-FREE GEOMETRIC ENZYMATIC NUCLEIC ACID SYNTHESIS

CROSS-REFERENCE TO RELATED APPLICATIONS

This application is a U.S. National Stage Application, filed under 35 U.S.C. § 371 of International Application No. PCT/US2020/013331, filed Jan. 13, 2020, which claims priority to and the benefit of U.S. Provisional Application No. 62/792,341, filed Jan. 14, 2019, the contents of each of which are incorporated herein by reference in their entireties for all purposes.

SEQUENCE LISTING

The instant application contains a Sequence Listing which has been submitted in ASCII format and is hereby incorporated by reference in its entirety. Said ASCII copy, created on Jan. 9, 2020, is named "DNWR-006_001WO_SeqList.txt" and is 17.7 KB in size.

FIELD OF THE DISCLOSURE

The present disclosure provides compositions and methods for template-free geometric enzymatic nucleic acid synthesis of arbitrarily programmed sequence.

BACKGROUND

Over the last decade there has been an increase in demand for synthetic DNA molecules, which are used in a range of molecular biology applications. This increase has, in part, been driven by advances in DNA sequencing technology. However, while there have been significant developments in DNA sequencing technology. DNA synthesis technology has not progressed at a comparable pace and consequently the state of the art technology does not satisfy the current market needs. The present disclosure provides compositions and methods for template-free geometric enzymatic DNA synthesis that provide a solution to the unmet need in the art for the production of long, error-free, inexpensive DNA sequences having the superior accuracy and speed of synthesis demonstrated by the compositions and methods of the present disclosure.

SUMMARY

The present disclosure provides a composition comprising a nucleic acid (NA) sequence capable of participating in geometric synthesis or parallel synthesis reactions, wherein the nucleic acid comprises an arbitrary length. In some aspects of the compositions of the disclosure, including those comprising a plurality of NA sequences, each NA sequence of the plurality of NA sequences comprises or consists of a 3-nucleotide oligonucleotide (a 3-mer), a 4-nucleotide oligonucleotide (a 4-mer), or a 5-nucleotide oligonucleotide (a 5-mer). In some aspects, each NA sequence of the plurality of NA sequences comprises or consists of a 3-mer and wherein the plurality of NA sequences comprises 64 unique NA sequences. In some aspects, each NA sequence of the plurality of NA sequences comprises or consists of a 4-mer and wherein the plurality of NA sequences comprises 256 unique NA sequences. In some aspects, each NA sequence of the plurality of NA sequences comprises or consists of a 5-mer and wherein the plurality of NA sequences comprises 1024 unique NA sequences. In some aspects, the plurality of NA sequences comprises or consists of each unique 3-mer sequence, each unique 4-mer NA sequence and each unique 5-mer NA sequence, and the plurality of NA sequences comprises 1344 unique NA sequences.

In some aspects of the compositions of the disclosure, each NA sequence of the plurality of NA sequences comprises a monophosphate at a 3' end or at a 5' end of the NA sequence. In some aspects, each NA sequence of the plurality of NA sequences comprises a monophosphate at a 3' end and at a 5' end of the NA sequence.

In some aspects of the compositions of the disclosure, each NA sequence of the plurality of NA sequences is 5' adenylated.

In some aspects of the compositions of the disclosure, each NA sequence of the plurality of NA sequences comprises a hydroxyl group at a 3' end or at a 5' end of the NA sequence. In some aspects, each NA sequence of the plurality of NA sequences comprises a hydroxyl group at a 3' end and at a 5' end of the NA sequence.

In some aspects of the compositions of the disclosure, each NA sequence of the plurality of NA sequences comprises a photo-convertible blocking group at a 3' end or at a 5' end of the NA sequence. In some aspects, each NA sequence of the plurality of NA sequences comprises a photo-convertible blocking group at a 3' end and at a 5' end of the NA sequence.

In some aspects of the compositions of the disclosure, each NA sequence of the plurality of NA sequences comprises an O-2-nitrobenzyl blocking at a 3' end or at a 5' end of the NA sequence. In some aspects, each NA sequence of the plurality of NA sequences comprises an O-2-nitrobenzyl blocking at a 3' end and at a 5' end of the NA sequence.

In some aspects of the compositions of the disclosure, each NA sequence of the plurality of NA sequences comprises a triphosphate at a 5' end of the NA sequence.

In some aspects of the compositions of the disclosure, at least one NA sequence of the plurality of NA sequences, a portion of the NA sequences of the plurality of NA sequences or each NA sequence of the plurality of NA sequences comprises a xenonucleic acid (XNA). In some aspects, at least one NA sequence of the plurality of NA sequences, a portion of the NA sequences of the plurality of NA sequences or each NA sequence of the plurality of NA sequences comprises a xenonucleic acid (XNA) and a deoxyribonucleic acid (DNA) or a ribonucleic acid (RNA).

In some aspects of the compositions of the disclosure, at least one NA sequence of the plurality of NA sequences, a portion of the NA sequences of the plurality of NA sequences or each NA sequence of the plurality of NA sequences consists of a xenonucleic acid (XNA).

In some aspects of the compositions of the disclosure, the XNA comprises a morpholino, a peptide nucleic acid (PNA), a 2'-O-methyl RNA, a 2'-fluoroarabino nucleic acid (FANA), a locked nucleic acid (LNA), a 1,5-dianhydrohexitol (HNA), a cyclohexene nucleic acid (CeNA), a threose nucleic acid (TNA), a glycol nucleic acid (GNA) or any combination thereof.

In some aspects of the compositions of the disclosure, including those in which at least one NA sequence of the plurality of NA sequences, a portion of the NA sequences of the plurality of NA sequences or each NA sequence of the plurality of NA sequences comprises or consists of an XNA, the XNA comprises a nucleic acid analog. In some aspects, the XNA comprises a modified nucleic acid. In some aspects, the XNA comprises a non-naturally occurring nucleic acid. In some aspects, the XNA comprises a synthetic nucleic acid. In some aspects, the XNA comprises a locked nucleic acid (LNA). In some aspects, the XNA comprises a detectable label. In some aspects, the label comprises a fluorophore, a chromaphore or a radioisotope. In some aspects, the label comprises a fluorophore. In some aspects, the fluorophore is Cy2, Cy3, Cy5, or an Alexa fluorophore; for example, 488, 568, 555, 647, 708. In some aspects, at least one NA sequence of the plurality of NA sequences, a portion of the NA sequences of the plurality of NA sequences or each NA sequence of the plurality of NA sequences comprises a chimeric sequence.

The disclosure provides a composition comprising a nucleic acid sequence comprising an anchor primer sequence, wherein the anchor primer sequence comprises a nucleic acid sequence comprising a spacer and a moiety and wherein the spacer and the moiety attach the anchor primer sequence to a solid support at a first end, and a release element, wherein the release element comprises at least one nucleic acid sequence that facilitates release of a distal sequence at a second end, wherein the distal sequence is located 3' of the release element. In some aspects, the moiety is positioned at a 5' end of the anchor primer sequence or at a 5' end of the nucleic acid sequence. In some aspects, the moiety is positioned at a 3' end of the anchor primer sequence or at a 3' end of the nucleic acid sequence. In some aspects, the moiety allows direct covalent attachment of the anchor primer sequence to the solid support. In some aspects, the moiety allows indirect or non-covalent attachment of the anchor primer sequence to the solid support. In some aspects, the moiety comprises an azide. In some aspects, the moiety comprises an alkyne. In some aspects, the moiety comprises a dibenzocyclooctyne (DBCO). In some aspects, the moiety comprises a biotin. In some aspects, the spacer comprises a polyethylene glycol (PEG). In some aspects, the release element or the distal sequence comprises a deoxyuridine. In some aspects, the release element or the distal sequence comprises a penultimate deoxyinosine at a 5' end of the release element, the distal sequence or the nucleic acid sequence. In some aspects, the release element or the distal sequence comprises an abasic deoxyribose. In some aspects, the release element or the distal sequence comprises a Type II S endonuclease site, an offset cutter endonuclease site, or a restriction endonuclease site. In some aspects, the release element or the distal sequence comprises a restriction endonuclease site. In some aspects, the release element or the distal sequence comprises a MlyI restriction endonuclease site. In some aspects, the release element or the distal sequence comprises a sequence capable be being cleaved by a single-stranded specific Cas9 endonuclease.

In some aspects of the compositions of the disclosure, the anchor primer sequence or the nucleic acid sequence comprising the anchor primer sequence has minimal secondary structure. In some aspects, the anchor primer sequence comprises a long homopolymeric tract or a simple bipolymeric tract. In some aspects, the e anchor primer sequence comprises a long bi-polymeric tract comprising a form $[CT]_N$. In some aspects, N can be about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 200, about 500, or about 1000.

In some aspects of the compositions of the disclosure, the composition comprises a plurality of nucleic acid sequences comprising an anchor primer sequence or a plurality of anchor primer sequences, wherein at least one nucleic acid sequence of the plurality of nucleic acid sequences or at least one anchor primer sequence of the plurality of anchor primer sequences comprises a NA sequence or an N-mer of the disclosure. In some aspects, each nucleic acid sequence of the plurality of nucleic acid sequences or each anchor primer sequence of the plurality of anchor primer sequences comprises a NA sequence or an N-mer of the composition. In some aspects, the anchor primer sequence of the at least one nucleotide sequence or of each nucleotide of the plurality of nucleic acid sequences comprising an anchor primer sequence has been extended to comprise the NA sequence or an N-mer of the disclosure. In some aspects, the at least one anchor primer sequence or each anchor primer sequence of the plurality of anchor primer sequences has been extended to comprise the NA sequence or an N-mer of the disclosure. In some aspects, the composition comprises a plurality of 64, 256, 1024 or 1344 unique nucleic acid sequences. In some aspects, the composition comprises a plurality of 64, 256, 1024 or 1344 unique nucleic acid sequences. In some aspects, each unique nucleic acid sequence comprises a monophosphate at a 3' end or at a 5' end. In some aspects, the each unique nucleic acid sequence comprises a hydroxyl group at a 3' end or at a 5' end.

The disclosure provides a composition comprising a solid support for the attachment of an anchor primer sequence or a plurality of anchor primer sequences. In some aspects, the solid support comprises a plurality of monodispersed beads. In some aspects, each of the plurality of monodispersed beads comprise polyacrylamide. In some aspects, each of the plurality of monodispersed beads comprise agarose. In some aspects, each of the plurality of monodispersed beads comprise polystyrene. In some aspects, each of the plurality of monodispersed beads comprise ferromagnetic particles. In some aspects, the solid support comprises a well or chamber. In some aspects, the solid support comprises a plurality of wells or chambers. In some aspects, the plurality of wells comprises a multi-well plate. In some aspects, the solid support comprises a glass. In some aspects, the solid support comprises a glass slide. In some aspects, the solid support comprises a quartz. In some aspects, the solid support comprises a quartz slide. In some aspects, the solid support comprises a polystyrene. In some aspects, the solid support comprises a polystyrene slide. In some aspects, the solid support comprises a coating and wherein the coating prevents non-specific binding of unwanted proteins, unwanted nucleic acids or other unwanted biomolecules. In some aspects, the coating comprises polyethylene glycol (PEG). In some aspects, the coating comprises triethylene glycol (TEG).

The disclosure provides a composition comprising an enzyme, one or more reaction components and specific N-mer substrates, wherein each N-mer substrate is capable of one and only one unit extension from either a 3' end or 5' end of an anchor primer in a geometric NA synthesis reaction. In some aspects, the one or more reaction components comprise potassium acetate, tris-acetate, magnesium acetate or bovine serum albumin. In some aspects, the one or more reaction components comprise polyethylene glycol 8000, hexamine cobalt chloride or adenosine triphosphate. In some aspects, the enzyme is selected from the group consisting of a ribozyme, a T4 RNA ligase, a T4 DNA ligase, a calf intestinal alkaline phosphatase, a shrimp alkaline phosphatase, a Klenow large fragment (3'-5' exonuclease), a lambda exonuclease (5"-3' exonuclease), a polynucleotide kinase, a terminal deoxynucleotidyl transferase (TdT), a DNA polymerase theta, an endonuclease V, an uracil DNA glycosylase, an endonuclease VIII, a 5' deadenylase or a transposase. In some aspects, the enzyme is a ribozyme. In some aspects, the transposase is a piggyBac transposase, a sleeping beauty transposase, or a Tn10 transposase. In some aspects, the enzyme comprises a mutation or a sequence variation having a desired new or a selectively eliminated activity.

In some aspects of the compositions of the disclosure, an anchor primer comprises an XNA. In some aspects, an anchor primer comprises an XNA and a DNA or an RNA.

In some aspects of the compositions of the disclosure, an anchor primer consists of XNAs.

The disclosure provides a composition comprising any nucleic acid sequence derived from 3' extension geometric synthesis, 5' extension geometric synthesis, 3' extension parallel synthesis or 5'3' co-synthesis.

The disclosure provides a composition, wherein each NA sequence of arbitrary length capable of participating in geometric synthesis or parallel synthesis reactions comprises DNA, RNA or a combination thereof. In some aspects, the NA sequence comprises a 5' terminal base that is a DNA base and a 3' terminal base that is an RNA base. In some aspects, either or both the 5' and 3' terminal nucleotides of each NA sequence possesses a reversible dimethoxytrityl-phosphate group. In some aspects, each NA sequence possesses an arbitrary number of DNA or RNA nucleotides in an arbitrary order.

The disclosure provides a vector comprising a composition of the disclosure. In some aspects, the vector further comprises a 5' inverted terminal repeat (ITR) and a 3' ITR. In some aspects, from 5' to 3', the vector comprises the 5' ITR, a least one N-mer sequence, and the 3' ITR. In some aspects, the vector further comprises a selectable marker. In some aspects, the selectable marker comprise a sequence encoding an antibiotic resistance gene. In some aspects, the sequence encoding an antibiotic resistance gene comprises a sequence encoding an ampicillin resistance gene.

The disclosure provides a composition comprising a vector of the disclosure.

The disclosure provides a method comprising: a) contacting at least one first plurality of solid supports and at least one first plurality of anchor primers, under conditions that allow for the attachment of a 3' terminus of at least one anchor primer of the at least one first plurality of anchor primers to at least one solid support of the at least one first plurality of solid supports to produce at least one first anchor primer-substrate complex; b) contacting the at least one first anchor primer-substrate complex and at least one first plurality of N-mers under conditions that append a 3' terminus of at least one N-mer of the at least one first plurality of N-mers to a 5' terminus of the at least one first anchor primer-substrate to produce at least one first extended anchor primer-substrate complex; c) contacting the at least one first extended anchor primer-substrate complex and at least one second plurality of N-mers under conditions that append a 3' terminus of at least one N-Mer of the at least one second plurality of N-mers to a 5' terminus of the at least one first extended anchor primer-substrate complex to produce at least one first donor complex; d) contacting at least one second plurality of solid supports and at least one second plurality of anchor primers, under conditions that allow for the attachment of a 3' terminus of at least one anchor primer of the at least one second plurality of anchor primers to at least one solid support of the at least one second plurality of solid supports to produce at least one second anchor primer-substrate complex; e) contacting the at least one second anchor primer-substrate complex and at least one third plurality of N-mers under conditions that append a 3' terminus of at least one N-mer of the at least one third plurality of N-mers to a 5' terminus of the at least one second anchor primer-substrate to produce at least one second extended anchor primer-substrate complex; f) contacting the at least one second extended anchor primer-substrate complex and at least one fourth plurality of N-mers under conditions that append a 3' terminus of at least one N-mer of the at least one fourth plurality of N-mers to a 5' terminus of the at least one second extended anchor primer-substrate complex to produce at least one first target complex; g) releasing at least one composition comprising the at least one N-mer of the at least one first plurality of N-mers and the at least one N-mer of the at least one second plurality of N-mers from the at least one first donor complex to produce at least one released intermediate complex; and h) contacting the at least one first target complex and the at least one released intermediate complex under conditions that append a 3' terminus of the at least one released intermediate complex to a 5' terminus of the at least one target complex to produce at least one first extended target complex.

In some aspects of the methods of the disclosure; appending comprises enzymatic ligation under conditions that allow for ligase activity. In some aspects, appending comprises ligation that is not enzymatic. In some aspects, the enzymatic ligation comprises T4 RNA ligase activity.

In some aspects of the methods of the disclosure, the method further comprises, after the production of the at least one first anchor primer-substrate complex, removing at least one unattached anchor primer.

In some aspects of the methods of the disclosure, the method further comprises, prior to removing the at least one unattached anchor primer, de-adenylating the at least one first anchor primer-substrate complex.

In some aspects of the methods of the disclosure, the method further comprises, after the production of the at least one second anchor primer-substrate complex, removing unattached anchor primers.

In some aspects of the methods of the disclosure, the method further comprises, prior to removing the at least one unattached anchor primer, de-adenylating the at least one second anchor primer-substrate complex.

In some aspects of the methods of the disclosure, removing the at least one unattached anchor primer comprises an exonuclease activity. In some aspects, the exonuclease comprises a 5' to 3' specific exonuclease. In some aspects, the 5' to 3' exonuclease cannot digest nucleic acid molecules comprising a 5' OH group.

In some aspects of the methods of the disclosure, the method further comprises, after production of the at least one first extended anchor primer-substrate complex, removing at least one un-appended N-mer.

In some aspects of the methods of the disclosure, the method further comprises, prior to removing the at least one un-appended N-mer, de-adenylating the at least one first extended anchor primer-substrate complex.

In some aspects of the methods of the disclosure, the method further comprises, after production of the at least one first donor complex, removing at least one un-appended N-mer.

In some aspects of the methods of the disclosure, the method further comprises, prior to removing the at least one un-appended N-mer, de-adenylating the at least one first donor complex.

In some aspects of the methods of the disclosure, the method further comprises, after production of the at least one second extended anchor primer-substrate complex, removing at least one un-appended N-mer.

In some aspects of the methods of the disclosure, the method further comprises, prior to removing the at least one un-appended N-mer, de-adenylating the at least one second extended anchor primer-substrate complex.

In some aspects of the methods of the disclosure, the method further comprises, after production of the at least one first target complex, removing at least one un-appended N-mer.

In some aspects of the methods of the disclosure, the method further comprises, prior to removing the at least one un-appended N-mer, de-adenylating the at least one first target complex.

In some aspects of the methods of the disclosure, the method further comprises, after production of the at least one first extended target complex, removing at least one un-appended N-mer.

In some aspects of the methods of the disclosure, the method further comprises, prior to removing the at least one un-appended N-mer, de-adenylating the at least one first extended target complex.

In some aspects of the methods of the disclosure, removing the at least one un-appended N-mer comprises an exonuclease activity. In some aspects, the exonuclease comprises a 5' to 3' specific exonuclease. In some aspects, the 5' to 3' exonuclease cannot digest nucleic acid molecules comprising a 5' OH group. In some aspects, the 5' to 3' exonuclease comprises a lambda exonuclease, a XRN-1 exonuclease or a combination thereof.

In some aspects of the methods of the disclosure, de-adenylating comprises an enzymatic activity. In some aspects, the enzymatic activity comprises a deadenylase activity. In some aspects, the deadenylase comprises a *S. cerevisiae* 5' deadenylase.

In some aspects of the methods of the disclosure, de-adenylating comprises a non-enzymatic activity.

In some aspects of the methods of the disclosure, the at least one first plurality of N-mers, the at least one second plurality of N-mers, the at least one third plurality of N-mers, the at least one fourth plurality of N-mers or any combination thereof comprise(s) at least one N-mer comprising an OH group at the 3' terminus and the 5' terminus of the N-mer.

In some aspects of the methods of the disclosure, the method further comprises, after production of the at least one first extended anchor primer-substrate complex and before contacting the at least one first extended anchor primer-substrate complex with at least one second plurality of N-mers, appending a $PO_4$ group to the 5' end of at least one N-mer of the at least one first plurality of N-mers.

In some aspects of the methods of the disclosure, the method further comprises, after producing the at least one second extended anchor primer-substrate complex and before contacting the at least one second extended anchor primer-substrate complex and at least one fourth plurality of N-mers, appending a $PO_4$ group to the 5' end of at least one N-mer of the at least one third plurality of N-mers.

In some aspects of the methods of the disclosure, the method further comprises, prior to contacting the at least one first target complex and the at least one released intermediate complex, appending a $PO_4$ group to the 5' end of at least one N-mer of the at least one fourth plurality of N-mers.

In some aspects of the methods of the disclosure, appending a $PO_4$ group comprises enzymatic phosphorylation. In some aspects, the enzymatic phosphorylation comprises T4 polynucleotide kinase activity.

In some aspects of the methods of the disclosure, appending a $PO_4$ group comprises non-enzymatic phosphorylation.

In some aspects of the methods of the disclosure, releasing the at least one composition occurs under conditions that preserve the OH group at the 3' terminus and the OH group at the 5' terminus of the at least one N-mer.

In some aspects of the methods of the disclosure, the at least one first plurality of N-mers, the at least one second plurality of N-mers, the at least one third plurality of N-mers, the at least one fourth plurality of N-mers or any combination thereof comprise(s) at least one N-mer comprising an OH group at the 3' terminus and a $PO_4$ group at the 5' terminus of the N-mer.

In some aspects of the methods of the disclosure, the $PO_4$ group is operably-linked to a protecting group. In some aspects, the protecting group comprises 4,4'-dimethoxytrityl phosphate.

In some aspects of the methods of the disclosure, the method further comprises, after production of the at least one first extended anchor primer-substrate complex and before the production of the at least one first donor complex, removing the protecting group from the at least one first extended anchor primer-substrate complex.

In some aspects of the methods of the disclosure, the method further comprises, after production of the at least one second extended anchor primer-substrate complex and before the production of the at least one first target complex, removing the protecting group from the at least one second extended anchor primer-substrate complex.

In some aspects of the methods of the disclosure, the method further comprises, before production of the at least one first extended target complex, removing the protecting group from the at least one first target complex.

In some aspects of the methods of the disclosure, releasing the at least one composition occurs under conditions that preserve the OH group at the 3' terminus and the $PO_4$ group at the 5' terminus of the N-mer.

In some aspects of the methods of the disclosure, the method further comprises, after production of the at least one first extended anchor primer-substrate complex and before the production of the at least one first donor complex, adenylating the 5' terminus of the at least one first extended anchor primer-substrate complex.

In some aspects of the methods of the disclosure, the method further comprises, after production of the at least one second extended anchor primer-substrate complex and before the production of the at least one first target complex, adenylating the 5' terminus of the at least one second extended anchor primer-substrate complex.

In some aspects of the methods of the disclosure, the method further comprises, before production of the at least one first extended target complex, adenylating the 5' terminus of the at least one first target complex.

In some aspects of the methods of the disclosure, adenylating comprises enzymatic activity. In some aspects, enzymatic activity comprises an 11th RNA ligase activity.

In some aspects of the methods of the disclosure, adenylation comprises non-enzymatic activity.

The disclosure provides a method comprising: a) contacting at least one first plurality of solid supports and at least one first plurality of anchor primers, under conditions that allow for the attachment of a 5' terminus of at least one anchor primer of the at least one first plurality of anchor primers to at least one solid support of the at least one first plurality of solid supports to produce at least one first anchor primer-substrate complex; b) contacting the at least one first anchor primer-substrate complex and at least one first plurality of N-mers under conditions that append a 5' terminus of at least one N-mer of the at least one first plurality of N-mers to a 3' terminus of the at least one first anchor primer-substrate to produce at least one first extended anchor primer-substrate complex; c) contacting the at least one first extended anchor primer-substrate complex and at least one second plurality of N-mers under conditions that append a 5' terminus of at least one N-mer of the at least one second plurality of N-mers to a 3' terminus of the at least one first extended anchor primer-substrate complex to produce at least one first donor complex; d) contacting at least one second plurality of solid supports and at least one second plurality of anchor primers, under conditions that allow for the attachment of a 5' terminus of at least one anchor primer of the at least one second plurality of anchor primers to at least one solid support of the at least one second plurality of solid supports to produce at least one second anchor primer-substrate complex; e) contacting the at least one second anchor primer-substrate complex and at least one third plurality of N-mers under conditions that append a 5' terminus of at least one N-mer of the at least one third plurality of N-mers to a 3' terminus of the at least one second anchor primer-substrate to produce at least one second extended anchor primer-substrate complex; f) contacting the at least one second extended anchor primer-substrate complex and at least one fourth plurality of N-mers under conditions that append a 5' terminus of at least one N-mer of the at least one fourth plurality of N-mers to a 3' terminus of the at least one second extended anchor primer-substrate complex to produce at least one first target complex; g) releasing at least one composition comprising the at least one N-mer of the at least one first plurality of N-mers and the at least one N-mer of the at least one second plurality of N-mers from the at least one first donor complex to produce at least one released intermediate complex h) contacting the at least one first target complex and the at least one released intermediate complex under conditions that append a 5' terminus of the at least one released intermediate complex to a 3' terminus of the at least one target complex to produce at least one first extended target complex. In some aspects of the preceding method; at least one N-mer and/or at least one anchor primer can comprise at least one XNA. In some aspects of the preceding method, at least one N-mer can be a chimeric N-mer.

In some aspects of the methods of the disclosure, appending comprises enzymatic ligation under conditions that allow for ligase activity. In some aspects, enzymatic ligation comprises a T4 RNA ligase activity.

In some aspects of the methods of the disclosure, appending comprises ligation that is not enzymatic.

In some aspects of the methods of the disclosure, the method comprises, after the production of the at least one first anchor primer-substrate complex, removing at least one unattached anchor primer.

In some aspects of the methods of the disclosure, the method further comprises, after the production of the at least one second anchor primer-substrate complex, removing at least one unattached anchor primer.

In some aspects of the methods of the disclosure, removing the at least one unattached anchor primer comprises an exonuclease activity. In some aspects, the exonuclease comprises a 3' to 5' specific exonuclease. In some aspects, the 3' to 5' exonuclease cannot digest nucleic acid molecules comprising a 3' $PO_4$ group.

In some aspects of the methods of the disclosure, the method further comprises, after production of the at least one first extended anchor primer-substrate complex, removing at least one un-appended N-mer.

In some aspects of the methods of the disclosure, the method further comprises, after production of the at least one donor complex, removing at least one un-appended N-mer.

In some aspects of the methods of the disclosure, the method further comprises, after production of the at least one second extended anchor primer-substrate complex, removing at least one un-appended N-mer.

In some aspects of the methods of the disclosure, the method further comprises, after production of the at least one target complex, removing at least one un-appended N-mer.

In some aspects of the methods of the disclosure, the method further comprises, after production of the at least one first extended target complex, removing at least one un-appended N-mer.

In some aspects of the methods of the disclosure, removing the at least one un-appended N-mer comprises an exonuclease activity. In some aspects, the exonuclease comprises a 3' to 5' specific exonuclease. In some aspects, the 3' to 5' exonuclease cannot digest nucleic acid molecules comprising a 3' $PO_4$ group. In some aspects, the 3' to 5' exonuclease comprises a Klenow polymerase.

In some aspects of the methods of the disclosure, the at least one first plurality of N-mers, the at least one second plurality of N-mers, the at least one third plurality of N-mers, the at least one fourth plurality of N-mers or any combination thereof comprise(s) at least one N-mer comprising a $PO_4$ group at the 3' terminus and the 5' terminus of the N-mer.

In some aspects of the methods of the disclosure, the method further comprises, after production of the at least one first extended anchor primer-substrate complex and before the production of the at least one first donor complex, removing the $PO_4$ group at the 3' terminus of the at least one first extended anchor primer-substrate complex.

In some aspects of the methods of the disclosure, the method further comprises, after production of the at least one second extended anchor primer-substrate complex and before the production of the at least one first target complex, removing the $PO_4$ group at the 3' terminus of the at least one first extended anchor primer-substrate complex.

In some aspects of the methods of the disclosure, the method further comprises, before production of the at least one first extended target complex, removing the $PO_4$ group at the 3' terminus of the at least one first target complex.

In some aspects of the methods of the disclosure, removing the $PO_4$ group comprises enzymatic phosphatase activity. In some aspects, the enzymatic phosphatase activity comprises calf intestinal alkaline phosphatase (CIP) activity, shrimp alkaline phosphatase (SAP) activity or any combination thereof.

In some aspects of the methods of the disclosure, removing the $PO_4$ group comprises non-enzymatic phosphatase activity.

The disclosure provides a method comprising, a) providing a first composition comprising a first plurality of anchor primers, wherein a 5' terminus of at least one anchor primer is operably-linked to at least one solid substrate and wherein the at least one anchor primer comprises a reversible blocking group at a 3' terminus to form a first blocked anchor primer-substrate complex and a second composition comprising at least a second plurality of anchor primers, wherein a 5' terminus of at least one anchor primer is operably-linked to at least one solid substrate and wherein the at least one anchor primer comprises a reversible blocking group at a 3' terminus to form a second blocked anchor primer-substrate complex, b) removing the reversible blocking group from either the first blocked anchor-primer substrate complex or the second anchor-primer substrate complex to produce at least one unblocked anchor primer-substrate complex; c) contacting the unblocked anchor primer-substrate complex and at least one first plurality of N-mers, each N-mer comprising a reversible blocking group at a 3' terminus of the N-mer, under conditions that append a 5' terminus of at least one N-mer of the at least one first plurality to a 3' terminus of the at least one unblocked anchor primer-substrate complex to form at least one blocked extended anchor primer-substrate complex; d) removing the reversible blocking group from the at least one blocked extended anchor primer-substrate complex to produce at least one unblocked extended anchor primer-substrate complexes; and e) contacting the unblocked extended anchor primer-substrate complex and at least one second plurality of N-mers, each N-mer comprising a reversible blocking group at a 3' terminus of the N-mer, under conditions that append a 5' terminus of at least one N-mer of the at least one first plurality to a 3' terminus of the at least one unblocked extended anchor primer-substrate complex to form at least one blocked donor complex. In some aspects of the preceding method, at least one N-mer and/or at least one anchor primer can comprise at least one XNA. In some aspects of the preceding method, at least one N-mer can be a chimeric N-mer.

In some aspects of the methods of the disclosure, a portion of the anchor primers of the first plurality of anchor primers are operably linked to at least one solid substrate.

In some aspects of the methods of the disclosure, a portion of the anchor primers of the second plurality of anchor primers are operably linked to at least one solid substrate.

In some aspects of the methods of the disclosure, each anchor primer of the first plurality of anchor primers is operably linked to at least one solid substrate.

In some aspects of the methods of the disclosure, each anchor primer of the second plurality of anchor primers is operably linked to at least one solid substrate.

In some aspects of the methods of the disclosure, each anchor primer of the first plurality of anchor primers is operably linked to a first solid substrate. In some aspects, each anchor primer of the second plurality of anchor primers is operably linked to a second solid substrate. In some aspects, the first substrate and the second substrate are the same. In some aspects, the first substrate and the second substrate are not the same.

In some aspects of the methods of the disclosure, the at least first plurality of anchor primers or the at least second plurality of anchor primers is arranged in an array. In some aspects, the at least first plurality of anchor primers is arranged in a first array and the at least second plurality of anchor primers is arranged in a second array. In some aspects, the first array and the second array are the same. In some aspects, the first array and the second array are not the same.

In some aspects of the methods of the disclosure, the reversible blocking group is a photo-liable blocking group. In some aspects, removing comprises exposing the photo-liable blocking group to light with a wavelength sufficient to induce removal of the photo-liable blocking group.

The disclosure provides a method comprising: a) contacting at least one first plurality of solid supports and at least one first plurality of anchor primers, under conditions that allow for the attachment of a terminus of at least one anchor primer of the at least one first plurality of anchor primers to at least one solid support of the at least one first plurality of solid supports to produce at least one first anchor primer-substrate complex; b) contacting the at least one first anchor primer-substrate complex and at least one first plurality of N-mers under conditions that append at least one N-mers of the at least one first plurality of N-mers to at least one first anchor primer-substrate, wherein at least one N-mer of the at least one first plurality of N-mers comprises a sequence encoding a 5' inverted terminal repeat (ITR) and a sequence encoding a 3' inverted terminal repeat (ITR) that are reverse oriented with respect to each other, to produce at least one first extended anchor primer-substrate complex; c) contacting the at least one first extended anchor primer-substrate complex and at least one second plurality of N-mers under conditions that append at least one N-mer of the at least one second plurality of N-mers to the at least one first extended anchor primer-substrate complex, wherein at least one N-mer of the at least one second plurality of N-mers comprises a sequence encoding a 5' inverted terminal repeat (ITR) and a sequence encoding a 3' inverted terminal repeat (ITR) that are reverse oriented with respect to each other, to produce at least one first elongated complex; d) excising from the at least one first elongated complex a nucleic acid sequence positioned between the 3' reverse-oriented ITR of the at least one N-mer of the at least one first plurality of N-mers and the 5' reverse-oriented ITR of the at least one N-mer of the at least one second plurality of N-mers to produce at least one first donor complex; e) contacting at least one second plurality of solid supports and at least one second plurality of anchor primers, under conditions that allow for the attachment of a terminus of at least one anchor primer of the at least one second plurality of anchor primers to at least one solid support of the at least one second plurality of solid supports to produce at least one second anchor primer-substrate complex; f) contacting the at least one second anchor primer-substrate complex and at least one third plurality of N-mers under conditions that append at least one N-mer of the at least one third plurality of N-mers to at least one second anchor primer-substrate, wherein at least one N-mer of the at least one third plurality of N-mers comprises a sequence encoding a 5' inverted terminal repeat (ITR) and a sequence encoding a 3' inverted terminal repeat (ITR) that are reverse oriented with respect to each other, to produce at least one second extended anchor primer-substrate complex; g) contacting the at least one second extended anchor primer-substrate complex and at least one fourth plurality of N-mers under conditions that append at least one N-mer of that at least one fourth plurality of N-mers to the at least one second extended anchor primer-substrate complex, wherein at least one N-mer of the at least one fourth plurality of N-mers comprises a sequence encoding a 5' inverted terminal repeat (ITR) and a sequence encoding a 3' inverted terminal repeat (ITR) that are reverse oriented with respect to each other, to produce at least one second elongated complex; h) releasing a composition comprising the 5' reverse oriented ITR, the at least one N-mer of the at least one first plurality of N-mers, the at least one second plurality of N-mers, and a 3' reverse oriented ITR of the at least one first donor complex to produce at least one released intermediate complex; i) contacting the at least one first target complex and the at least one released intermediate complex under conditions that append the at least one released intermediate complex to the at least one first target complex to produce at least one first extended target complex; and j) excising from the at least one first extended target complex a nucleic acid sequence between the at least one N-mer of the at least one fourth plurality of N-mers and the at least one N-mer of the at least one first plurality of N-mers located to produce at least one first excised extended target complex. In some aspects of the preceding method, at least one N-mer and/or at least one anchor primer can comprise at least one XNA. In some aspects of the preceding method, at least one N-mer can be a chimeric N-mer.

In some aspects of the methods of the disclosure, the sequence encoding the 5' ITR and sequence encoding the 3'ITR of the at least one N-mer are derived from a precisely excising transposable element.

In some aspects of the methods of the disclosure, the releasing comprises an enzymatic activity. In some aspects, the releasing comprises a break in a sequence of one or more of a 3' ITR, a 3' terminus, a 5' terminus, or a 5' ITR. In some aspects, the releasing produces a 5' or a 3' overhang.

In some aspects of the methods of the disclosure, the releasing comprises a non-enzymatic activity.

In some aspects of the methods of the disclosure, the appending comprises an enzymatic activity. In some aspects, the appending comprises a ligation.

In some aspects of the methods of the disclosure, the appending comprises a non-enzymatic activity.

In some aspects of the methods of the disclosure, at least one anchor primer comprises a composition of the disclosure.

The disclosure provides a method comprising: a) providing a template complex that comprises at least one template nucleic acid molecule, wherein a first terminus of the template nucleic acid molecule is operably-linked to a solid support, wherein the first terminus comprises a first primer binding region and, wherein a second terminus of the template nucleic acid molecule comprises a second primer binding region; b) contacting the template complex and at least one first amplification primer, wherein the at least one first amplification primer comprises a nucleic acid sequence that is complementary to the second primer binding region under conditions sufficient for the hybridization of the at least one first amplification primer to the second primer binding region; c) extending the at least one first amplification primer to produce at least one first replicated nucleic acid molecule; d) contacting the at least one first replicated nucleic acid molecule and at least one substrate bound primer complex, wherein the at least one substrate bound primer complex comprises at least one second amplification primer operably-linked to a solid support, wherein the at least one second amplification primer comprises a nucleic acid sequence complementary to the first primer binding region under conditions sufficient for the hybridization of that least one second amplification primer to the at least one first replicated nucleic acid molecule; and e) extending the at least one second amplification primer to produce at least one first replicated duplex.

In some aspects of the methods of the disclosure, at least one solid support comprises a composition of the disclosure.

The disclosure provides a method comprising: (a) contacting a plurality of nucleic acid sequences under conditions suitable for at least a first sequence to form first duplex with a second sequence and the first sequence to form a second duplex with a third sequence, wherein each sequence comprising a first region of complementarity and a second region of complementarity, wherein the first region of complementarily comprises a portion of the sequence that can form a first duplex in the presence of second sequence, wherein the second region of complementarity comprises a portion of sequence that can form a second duplex with a third sequence, wherein the second sequence and the third sequence are distinct; and (b) inducing synthesis from a 3' terminus of at least one sequence of the first duplex or the second duplex under conditions suitable for nucleic acid polymerization to form at least 1 extended sequence.

In some aspects of the methods of the disclosure, the plurality of nucleic acid sequences comprises sense sequences and antisense sequences. In some aspects, the plurality of nucleic acid sequences comprises at least 2 sense sequences or at least 2 antisense sequences. In some aspects, the plurality of nucleic acid sequences comprises at least 2 sense sequences or at least 2 antisense sequences. In some aspects, the method forms at least 2 extended sense sequences or at least 2 extended antisense sequences. In some aspects, the method further comprises appending the at least 2 extended sense sequences or at least 2 extended antisense sequences to form a unified sense strand or a unified antisense strand. In some aspects, the appending comprises an enzymatic activity. In some aspects, the appending comprises a ligation or a ligase activity. In some aspects, the appending comprises a non-enzymatic activity.

In some aspects of the methods of the disclosure, at least one sequence of the plurality of nucleic acid sequences comprises an N-mer. In some aspects, the N-mer is a 3-mer or a 5-mer. In some aspects, at least one sequence of the plurality of nucleic acid sequences is produced according to the method of the disclosure. In some aspects, a portion of the sequences of the plurality of nucleic acid sequences is produced according to the method of the disclosure. In some aspects, each sequences of the plurality of nucleic acid sequences is produced according to the method of the disclosure.

The disclosure provides a nucleic acid sequence produced according to the method of the disclosure.

The disclosure provides a vector comprising a nucleic acid sequence of the disclosure, including those produced according to the method of the disclosure.

The disclosure provides a composition comprising a nucleic acid sequence of the disclosure, including those produced according to the method of the disclosure.

The disclosure provides a composition comprising the vector of the disclosure.

The disclosure provides a cell comprising a nucleic acid sequence of the disclosure, including those produced according to the method of the disclosure.

The disclosure provides a cell comprising the vector of the disclosure.

The disclosure provides a cell comprising the composition of the disclosure.

The disclosure provides a composition comprising a cell of the disclosure.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

FIG. 2A shows an example of low-complexity sequences possessing Type II S restriction enzyme site, MlyI for 3' extension. FIG. 2B shows an example of low-complexity sequences possessing Type II S restriction enzyme site, MlyI for 5' extension. FIG. 2C shows a low-complexity sequence possessing a dexoyuridine (U) for release using a combination of Uracil DNA glycosylase and DNA glycosylase-lyase Endonuclease VIII for 3' extension. FIG. 2D shows the combination of deoxyadenosine (A) and deoxyinosine (I) at the 5' end of a low-complexity anchor primer sequence, is a target of Endonuclease V for release of synthetic NA product.

FIG. 3A-B highlights a fragment of GFP cDNA, used in the present disclosure to demonstrate the 3' geometric synthesis method. FIG. 3A shows a FASTA representation of the complete cDNA sequence for green fluorescent protein (GFP) (NCBI accession number L29345). The demonstration fragment comprises the first eight 21-mer sequences. These are highlighted in a range of colors. FIG. 3B shows the distribution of 21-mer sequences into two plate sets for assembly using the 3' geometric synthesis method. The first eight 21-mers are highlighted in the colors corresponding to the FASTA file representation.

FIG. 16 is a schematic overview of locked nucleic acids (LNAs) and Cy3-labeled internal linkers.

DETAILED DESCRIPTION

Figure 1:
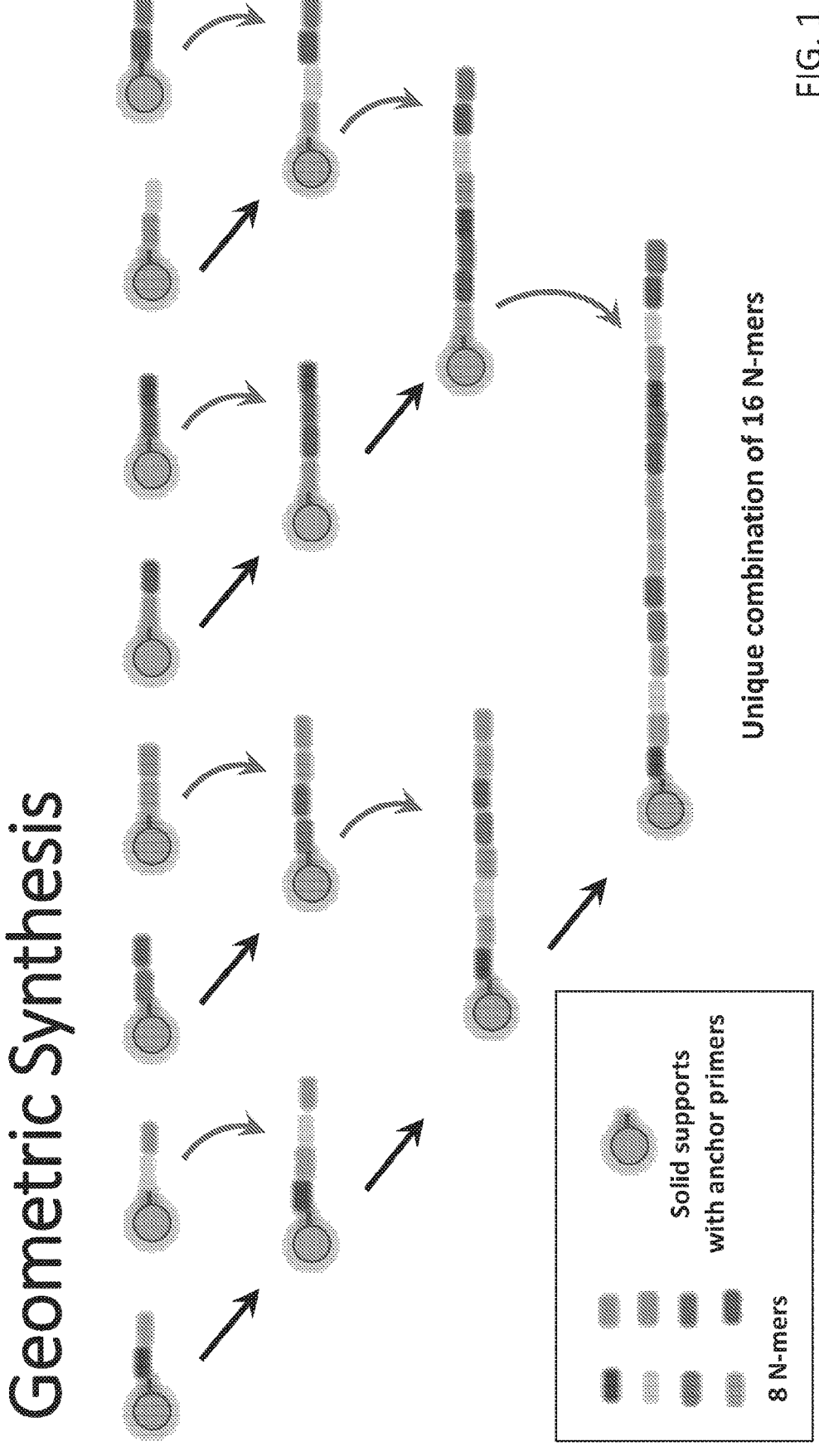
FIG. 1 is a schematic diagram depicting the central idea behind geometric synthesis. In this example eight different N-mers and the solid substrate bound anchor primer sequences are the starting materials. The first row depicts the situation after the first two rounds of ligation, wherein two N-mers have been added to anchor primers. In subsequent steps, such as row two, there are target samples, and donor samples. Target sample remain bound to solid supports and donor samples are released and used to extend corresponding target samples. After several rounds, a single target sample possesses the complete synthesized. Here the complete synthetic strand is comprised of 16 N-mer in a unique configuration.

The present disclosure provides compositions, kits and methods for template-free geometric enzymatic nucleic acid synthesis of an arbitrarily programmed sequence.

The present disclosure provides compositions and methods for the enzymatic, template-independent, synthesis of nucleic acid (NA) polymers using short, error free NA fragments, systematically assembled to form arbitrarily long NA chains. Unique NA sequences can be synthesized by the systematic joining of shorter NA sequences using comprehensive libraries of purified short oligonucleotides and constant primer sequences. Libraries of short, error free NA fragment sequence can vary in size, but comprehensive coverage of all possible sequences is most achievable with 3-mers, having 64 possible sequences, 4-mers, with 256 possible sequences and 5-mers with 1024 possible sequences. Any longer sequence can be assembled by a sequential combination of 3-mers, 4-mers or 5-mers, collectively referred to as N-mers. The present disclosure also provides compositions of plasmid libraries containing all possible 3-mer, 4-mer and 5-mers in the form of enzymatically excisable elements. The present disclosure provides compositions of modified N-mers, assembled sequences, plasmid constructs, reaction conditions, reaction substrates and proprietary short oligo sequences. Additionally, the present disclosure provides several different methods for fast, accurate generation of long arbitrary NA chains as well as surface to surface amplification of NA molecules.

The present disclosure provides compositions comprising N-mers for both 3' and 5' extension in non-templated NA synthesis. These N-mers include all possible 3-mers (64), 4-mers (256) and 5-mers (1024) comprising either RNA or DNA. For 5' non-templated extension, the N-mer oligonucleotides do not require a phosphate group at either the 3' or 5' end. For 3' non-templated extension N-mers may possess a phosphate group at both 3' and 5' ends of each oligonucleotide. Additionally, N-mers may include reversible extension blocking groups, such as photo-labile blocking groups or the 4,4'-dimethoxytrityl phosphate (DMT-PO$_4$) group, at either the 5' end the 3' end or both ends of the N-mer oligonucleotide. Additionally, 5' ends may be activated by 5' adenylation for subsequent ligation with appropriately selective enzymes. 5' adenylation can be performed; for example, by treatment of the N-mer with filth RNA ligase.

In some contexts, the term nucleic acid may refer to a nucleic acid monomer (nucleotide) and in some contexts the term nucleic acid may refer to a nucleic acid polymer (polynucleotide). In some contexts, the term xenonulceic acid (XNA) may refer to a monomeric xenonucleic acid (xenonucleotide) and in some contexts the term xenonulceic acid may refer to a xenonucleic acid polymer (polyxenonucleotide).

The present disclosure provides compositions comprising N-mers of any possible 3-mer (64), 4-mer (256) and 5-mer (1024) comprising RNA, DNA, xenonucleic acid (XNA) or any combination thereof. These N-mers may be chimeric NA molecules with a deoxyribose 5' (DNA) terminus and a ribose 3' (RNA) terminus. These N-mers may be wholly or partially comprised of DNA, RNA or XNA backbones.

Figure 16:
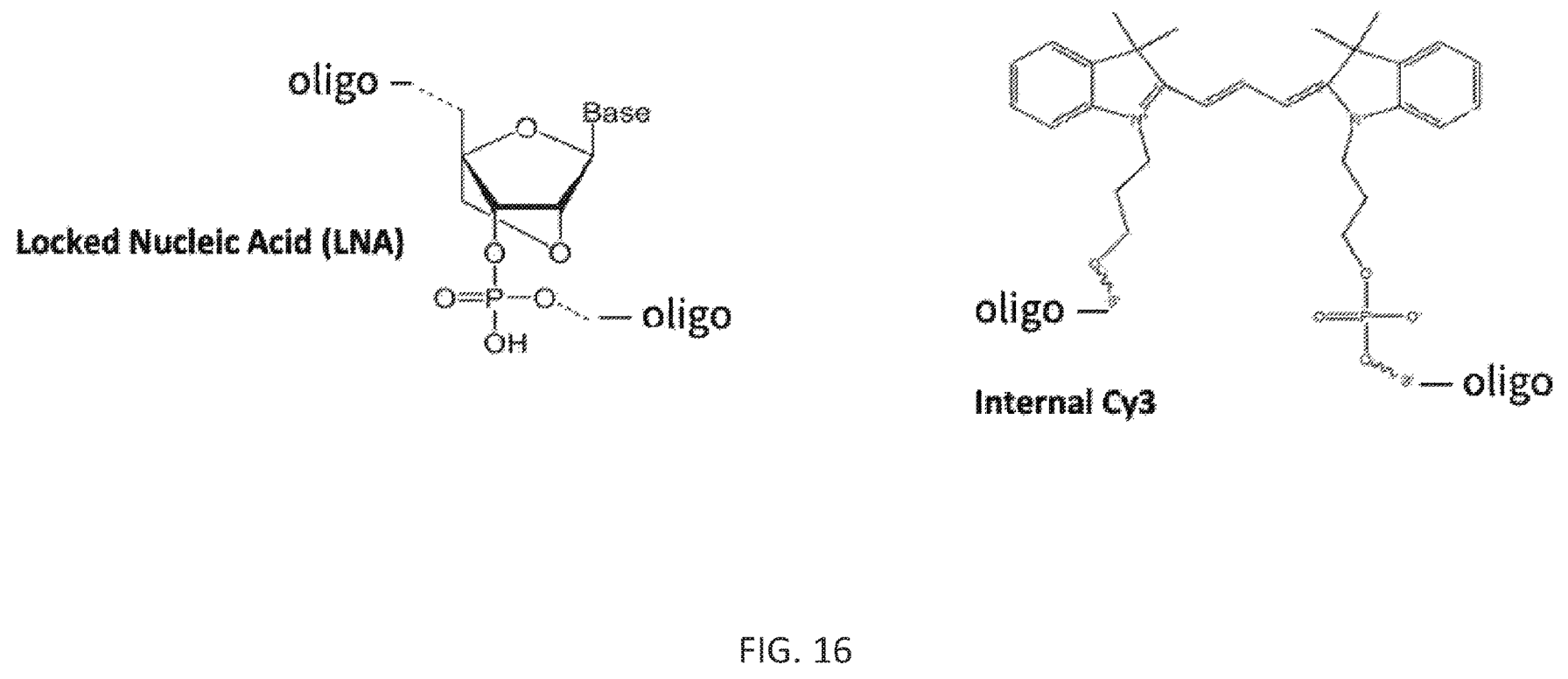
Figure 17:
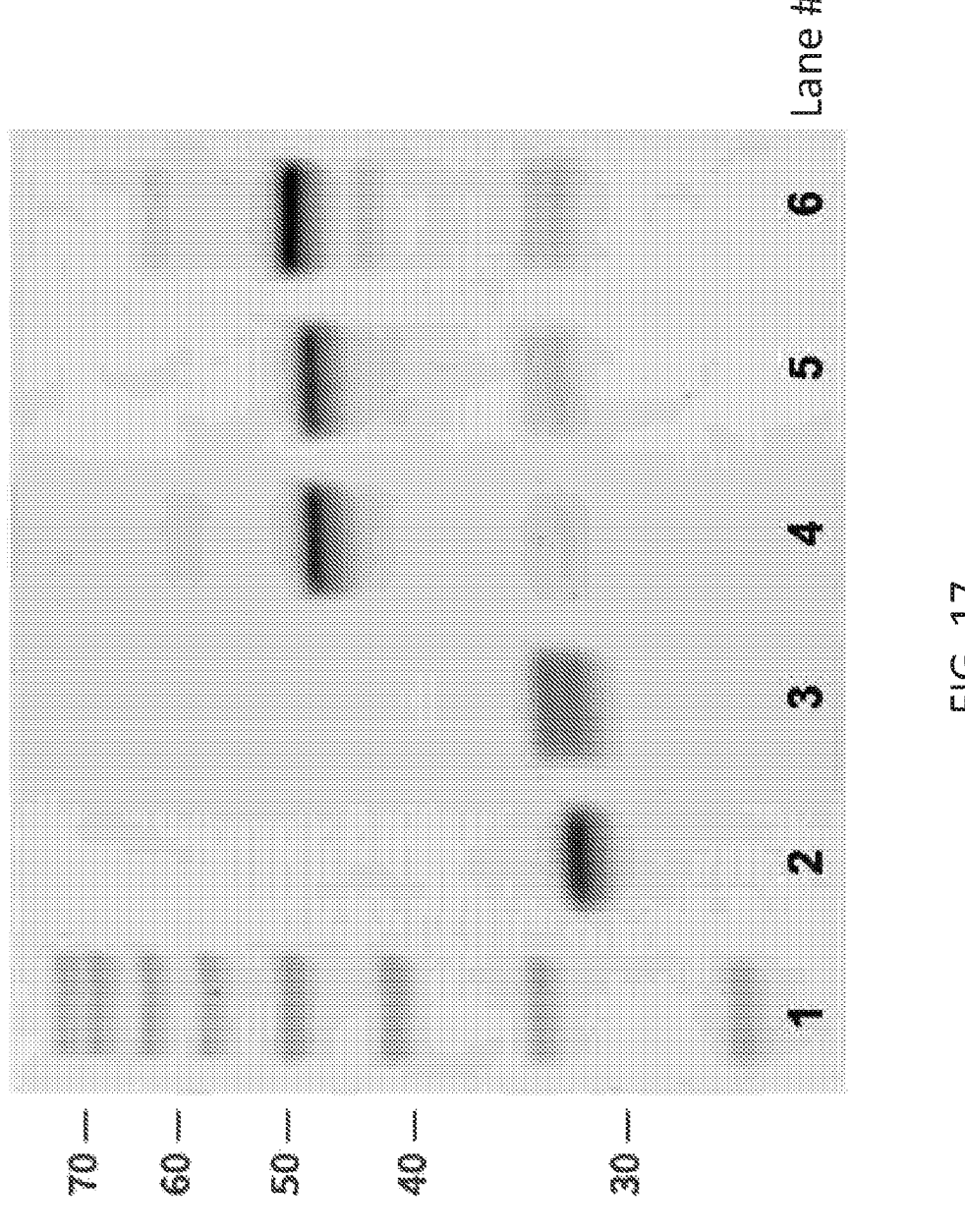
FIG. 17 is an image of a polyacrylamide gel used to analyze the products of various ligations of N-mers comprising XNA.

In some aspects, XNA can include, but is not limited to, morpholine, peptide nucleic acids (PNA), 2'-O-methyl RNA, 2'-fluoroarabino nucleic acids (FANAs), locked nucleic acids (LNAs; as shown in the left panel of FIG. 16), 1,5-dianhydrohexitol (HNAs), cyclohexene nucleic acid (CeNA), threose nucleic acid (TNA), glycol nucleic acid (GNA), internally-labeled nucleic acids (e.g. internal Cy3-labeled nucleic acids; as shown in the right panel of FIG. 17) or any combination thereof.

The present disclosure provides compositions comprising assembled modules of N-mers into NA oligonucleotides of arbitrary length and sequence. These oligonucleotides may wholly or partially comprise DNA, RNA or XNA.

The present disclosure provides compositions comprising N-mers for 3' extension in non-templated NA synthesis. These N-mers include all possible 3-mers (64), 4-mers (256) and 5-mers (1024) comprising either RNA, DNA or XNA. These N-mers possess 5' triphosphate groups which may be a substrate for terminal transferase activity.

The present disclosure provides compositions comprising anchor primer sequences, which are proprietary short oligonucleotide sequences generally attached to a solid support with either the 3' or 5' end distal to the solid support. These oligonucleotide sequences are designed to allow the specific removal of any additional sequence that has been extended from the end of the anchoring primer sequence. Specific removal from the distal end of the anchoring primer sequence may be accomplished in several ways.

The present disclosure provides compositions comprising attachments of anchor primers to solid supports. Attachments may be non-covalently mediated, such as by biotin and avidin interactions or may be covalent links, such as a range of 'click' chemistries. Attachments may include spacer molecules such as polyethylene glycol (PEG) or triethylene glycol (TEG).

In certain aspects of the compositions of the present disclosure, for precise release of synthetic NA, include anchoring primer NAs with appropriately positioned abasic sites, which may be cut with DNA glycosylase-lyase Endonuclease VIII. Additionally, appropriately positioned deoxyuridine (U) sites may be first made abasic through the activity of Uracil DNA glycosylase, then the resulting abasic site may be cut using DNA glycosylase-lyase Endonuclease VIII.

In certain aspects of the compositions of the present disclosure, for precise release of synthetic NA, include anchoring primer NAs with appropriately positioned deoxyinosine (I) sites, which may be cut with Endonuclease V.

In certain aspects of the compositions of the present disclosure, for precise release of synthetic NA, include anchoring primer NAs with appropriately positioned sites for cleavage by a variety of restriction endonucleases (RE). These restriction nuclease sites may be for offset cutting REs, called Type II S restriction endonucleases, such as the enzyme MlyI.

In certain aspects of the compositions of the present disclosure, for precise release of synthetic NA, include anchoring primer NAs with appropriately positioned sites for single stranded specific cutting by Cas9 and appropriate guide RNAs.

The present disclosure provides compositions comprising solid supports. There are several solid supports are effective in the context of geometric synthesis. Specifically, solid supports include microscopic beads, magnetic or non-magnetic, made of polyacrylamide, polystyrene, crosslinked agarose or other similar materials. Solid supports may also include plastic or glass surfaces, such as the surfaces of wells of multi-well plates. Solid supports may be treated to enhance the NA binding properties or permit specific enzymatic activities. Likewise, surfaces may be treated to prevent non-specific or un-wanted binding.

The present disclosure provides compositions comprising DNA or RNA ligases, either ribozyme or protein, such as T4 RNA ligase, including mutant or modified DNA or RNA ligases, which require 5' adenylated N-mer substrates. Ligase are mixed with solid surface bound anchor primers and/or extended NA and N-mers in appropriate reactions solutions to affect the extension of the NA chain by one and only one. N-mer unit.

In certain aspects of the compositions of the present disclosure, extension of the synthetic NA chain is mediated by terminal transferase enzymes such as terminal deoxynucleotidyl transferase (TdT), members of the X family of DNA polymerases or DNA polymerase Pol theta.

The present disclosure provides compositions comprising NA sequences derived de novo from a geometric synthesis process. In certain aspects of the present disclosure sequences of NA are generated by combinations of N-mers. These NA sequences can be generated by the geometric 3' method, by the geometric 5' method, by the geometric transposase method or by the geometric 3', 5' co-synthesis method.

The present disclosure provides compositions comprising NA sequences derived de novo from 3' extension parallel synthesis using N-mers. A multiplicity of NA sequences generated in parallel are made by one at a time extension from solid support bound anchor primers.

The present disclosure provides compositions of plasmid sequences that possess N-mer sequences for enzymatic addition of N-mers using transposase elements. Activity of transposases lead to the excision of transposable element specific sequences from the elongating synthetic NA chain, leaving only N-mer additions. The basic plasmid design includes 1) reverse oriented, transposable element derived right and left inverted terminal repeat (ITR) elements positioned on either side of an N-mer sequence, 2) a selectable marker, such as ampicillin resistance, 3) an origin of replication and 4) a multiple cloning site containing a n appropriate set of restriction endonuclease sites. The present disclosure provides compositions for a plurality of plasmid sequence each possessing a unique N-mer sequence as well as transposable element specific sequences and elements for the propagation of the plasmid in bacterial cells.

The present disclosure provides compositions comprising a system for the amplification of intermediate or final products of geometric NA synthesis. Solid supports, for example beads, micro-well plate surfaces or glass slide surfaces are coated with oligonucleotide primers, which are also anchor primers for ongoing synthesis reactions. A template bearing surface and an anchor primer bearing surface are brought together in a common reaction buffer along with free oligonucleotide primers, which are the reverse complementary sequence of the distal end of the template NA. Amplification is carried out by polymerase chain reaction, recombinase-polymerase reaction or a similar NA replication, amplification system.

The present disclosure provides a method of 5' extension geometric synthesis. Initially an appropriate number of samples is set up, for example in multi-well plates. Each sample first contains anchor primers, which bear —$PO_4$ at 5' ends and have been affixed to solid supports. 1) The process begins with ligation of an N-mer species onto anchor primers. The N-mers bear a —OH at each the 3' and 5' ends. 2) After the first ligation, a 5' to 3' specific exonuclease, such as Lambda exonuclease is used to remove un-ligated anchor primers from the solid supports. Lambda cannot digest NAs bearing a 5'-OH. 3) After exonuclease digestion samples are treated with Polynucleotide Kinase (PNK), to produce a —$PO_4$ at each 5' end. 4) A second round of ligation with another N-mer species is carried out as in the first ligation, this is followed by a similar 5' to 3' exonuclease digestion. 5) After first two rounds of ligation and exonuclease treatment samples become either 'targets' or 'donors'. 5a) Target samples receive PNK treatment. 5b) Donor samples are released from solid support, preserving —OH groups both 3' and 5' groups, using described methods such as a restriction enzyme to cut a partially double stranded anchor primer. On subsequent rounds 'donor' samples are ligated to 'target' samples according to 1), 2) and 5).

The present disclosure provides a method of 3' extension geometric synthesis. Initially an appropriate number of samples is set up, for example in multi-well plates. Each sample first contains anchor primers, which bear —OH at 3' ends and have been affixed to solid supports. I) The process begins with ligation of an N-mer species onto anchor primers. The N-mers bear a —PO$_4$ at each the 3' and 5' ends. 2) After the first ligation, a. 3' to 5' specific exotruclease, such as Klenow is used to remove un-ligated anchor primers from the solid supports. Klenow cannot digest NAs bearing a 3'-PO$_4$. 3) After exonuclease digestion samples are treated with phosphatase, such as Calf Intestinal Alkaline Phosphatase (CIP) or Shrimp Alkaline Phosphatase (SAP), to remove 3'-PO$_4$. 4) A second round of ligation with another N-mer species is carried out as in the first ligation, this is followed by a similar 3' to 5' exonuclease digestion. 5) After first two rounds of ligation and exonuclease treatment samples become either 'targets' or 'donors'. 5a.) Target samples receive phosphatase treatment. 5b) Donor samples are released from solid support, preserving both 3' and 5'-PO$_4$ groups using described methods such as a restriction enzyme cutting a partially double stranded anchor primer. On subsequent rounds 'donor' samples are ligated to 'target' samples according to 1), 2) and 5).

The present disclosure provides a method of 3' extension parallel synthesis using N-mers. The N-mers described in the present disclosure may also possess reversible blocks on the 3' hydroxyl group, which make the site unavailable for enzymatic incorporation of additional nucleotides. N-mers or longer oligonucleotides. The reversible block may be removed by a variety of methods, including exposure to light or chemical reagents. In parallel synthesis, many different reactions can be specifically controlled allowing arbitrary incorporation of specific N-mers. In a two-dimensional grid, regions are specifically addressed by light focused on grid elements. Exposed areas become activated and are then able to incorporate the available short oligonucleotide sequence. The two-dimensional grid may begin with general attachment of 3' reversibly blocked anchor primer sequences. If the incorporation of a specific N-mer, such as ACG, is required, then the region of the two-dimensional grid where ACG is required is exposed to light, which will reverse the block and allow the ACG N-mer to be incorporated only there. Such a process ensues for all 64 possible 3-mers suitably blocked at the 3' end. Any possible sequence combination can be manifest at any specific location on the grid. The grid may be a chamber with activated regions on a flat glass or similar surface. Additionally, the grid may be a chamber capable of holding an array of beads with attached anchor primers. In either case the reagents of the reactions are delivered by a microfluidic system.

The present disclosure provides a method of double stranded geometric synthesis mediated by transposases. This method relies on a collection of plasmids with reverse oriented left and right terminal repeats derived from a precisely excising transposable element, such as piggyBac. Each plasmid in the collection carries a different N-mer sequence (3-, 4-, and 5-mers). Prior to synthesis reactions each required N-mer sequence is excised from its plasmid backbone by appropriate restriction endonuclease (RE) or similar digestion. As with the 5' and 3' extension geometric synthesis methods, multiple parallel reactions are carried out. Each reaction possesses a solid support carrying a double-stranded anchor primer sequence with a distal RE site compatible with the RE used to excise the N-mer sequence from the plasmids. 1) The process begins with ligation of an N-mer carrying inverse transposable element onto anchor primers followed by reaction cleanup. By placing the normal left-side inverted terminal repeat sequence (ITR) on the right side and the right-side ITR on the left side of the N-mer sequence, the resulting inverse transposable element is not a target transposase activity. 2) A second N-mer carrying inverse transposable element is then ligated to the extending NA chain on the solid support followed by cleanup. 3) Treatment of the extending NA chain with transposase leads to the excision of the intervening sequence between the two N-mer sequences. 3) The ligated, excised NA chain can be released from the beads by a RE reaction and can then serve as a 'donor' for a subsequent ligation reaction. 4) Cycles of cleavage and transfer, ligation and cleanup, followed by excision using appropriate 'donors' and 'targets' will lead eventually to the desired. NA sequence.

The present disclosure provides a method of 5' extension and 3' extension geometric co-synthesis. This allows accelerated long, fast NA synthesis using a mixed 3', 5' co-synthesis with DNA polymerase filling and ligation. Initially a set of partially overlapping NA fragments is generated using another method. An annealing reaction is carried out with the partially overlapping complementary fragments. A polymerase reaction extends each of the overlapping 3' end is extended. The final product is generated by a ligase reaction that resolved the breaks between fragments.

The present disclosure provides a method of surface to surface transfer amplification. Amplification begins with template molecules, which are brought into the reaction on a solid support. The template NA molecules bear unique sequences at the proximal and distal ends. In the case of a geometric synthesis reaction, the distal unique sequence may be ligated onto the template sequence. These sequences are used as targets for primers: primers attached to the beads, which in the case of geometric synthesis would essentially be the anchor primers, and opposing primers that are free in solution. In the amplification reaction, which can be mediated by either PCR or RPA, a polymerase synthesizing from a template bound free primer will make a reverse complement copy of the template NA. The replicated strand is released, for example, during the melt phase of a PCR cycle, and can then hybridize to acceptor-surface bound primers. The copy strands then serve as templates for new generation of original NA molecules mediated by polymerase synthesizing from surface-bound primers (black). In surface to surface transfer amplification many surfaces will work. The donor surface could be a small bead and the acceptor a larger bead. If the smaller bead were 20 μm in diameter and the larger bead 150 μm in diameter the degree of amplification would be more than 50-fold. Alternatively, the template may be initially on the surface of a well of a multi-well plate and the acceptor surface could be a bead introduced into the well. Likewise, the donor surface may be a small bead introduced to a large surface well or onto a flat surface of a microscope slide. NAs are both amplified and transferred in the reaction.

Any of the above aspects can be combined with any other aspect.

Unless otherwise defined, all technical and scientific terms used herein have the same meaning as commonly understood by one of ordinary skill in the art to which the present disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

N-mers

In some aspects, the present disclosure provides a composition comprising an N-mer, as described in detail herein. An N-mer can comprise a polynucleotide. An N-mer can comprise at least about 1 nucleotide, or at least about 2 nucleotides, or at least about 3 nucleotides, or at least about 4 nucleotides, or at least about 5 nucleotides, or at least about 6 nucleotides, or at least about 7 nucleotides, or at least about 8 nucleotides, or at least about 9 nucleotides, or at least about 10 nucleotides, or at least about 11 nucleotides, or at least about 12 nucleotides, or at least about 13 nucleotides, or at least about 14 nucleotides, or at least about 15 nucleotides, or at least about 16 nucleotides, or at least about 17 nucleotides, or at least about 18 nucleotides, or at least about 19 nucleotides, or at least about 20 nucleotides, or at least about 21 nucleotides, or at least about 22 nucleotides, or at least about 23 nucleotides, or at least about 24 nucleotides, or at least about 25 nucleotides, or at least about 26 nucleotides, or at least about 27 nucleotides, or at least about 28 nucleotides, or at least about 29 nucleotides, or at least about 30 nucleotides, or at least about 31 nucleotides, or at least about 32 nucleotides, or at least about 33 nucleotides, or at least about 34 nucleotides, or at least about 35 nucleotides, or at least about 40 nucleotides, or at least about 45 nucleotides, or at least about 50 nucleotides, or at least about 60 nucleotides. An N-mer that comprises 1 nucleotides is herein referred to as a 1-mer, an N-mer that comprises 2 nucleotides is herein referred to as a 2-mer, and so on and so forth.

In some aspects, an N-mer can comprise a 3'-PO$_4$ group. In some aspects, an N-mer can comprise a 5'-PO$_4$ group. In some aspects, an N-mer can comprise a 3'-PO$_4$ group and a 5'-PO$_4$ group.

In some aspects, an N-mer can comprise a 3'-OH group. In some aspects, and N-mer can comprise a 5'-OH group. In some aspects, and N-mer can comprise a 3'-OH group and a 5'-OH group.

In some aspects, an N-mer can comprise a 3' triphosphate group. In some aspects, an N-mer can comprise a 5' triphosphate group. In some aspects, an N-mer can comprise a 3' triphosphate group and a 5' triphosphate group.

In some aspects, an N-mer can comprise RNA. In some aspects, an N-mer can comprise DNA. In some aspects, an N-mer can comprise XNA. In some aspects, an N-mer can comprise DNA and RNA, referred to herein as a chimeric N-mer. In some aspects, an N-mer can comprise DNA and XNA, also referred to herein as a chimeric N-mer. In some aspects, an N-mer can comprise RNA and XNA, also referred to herein as a chimeric N-mer. In some aspects, an N-mer can comprise DNA, RNA and XNA, also referred to herein as a chimeric N-mer.

An N-mer can be wholly or partially comprised of DNA, RNA or XNA. An N-mer can be about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95% RNA. An N-mer can be about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95% DNA. An N-mer can be about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95% XNA.

In some aspects, an N-mer can be a chimeric N-mer comprising a deoxyribose 5' (DNA) terminus and a ribose 3' (RNA) terminus. In some aspects, an N-mer can be a chimeric N-mer comprising a deoxyribose 3' (DNA) terminus and a ribose 5' (RNA) terminus. In some aspects, an N-mer can be a chimeric N-mer comprising a deoxyribose 5' (DNA) terminus and a 3' XNA terminus. In some aspects, an N-mer can be a chimeric N-mer comprising a deoxyribose 3' (DNA) terminus and a 5' XNA terminus. In some aspects, an N-mer can be a chimeric. N-mer comprising a ribose 5' (RNA) terminus and a 3' XNA terminus. In some aspects, an N-mer can be a chimeric N-mer comprising a ribose 3' (RNA) terminus and a 5' XNA terminus.

In some aspects, an N-mer can be a chimeric N-mer comprising a deoxyribose 5' (DNA) terminus and a deoxyribose 3' (DNA) terminus. In some aspects, an N-mer can be a chimeric N-finer comprising a ribose 5' (RNA) terminus and a ribose 3' (RNA) terminus. In some aspects, an N-mer can be a chimeric N-mer comprising a 5' XNA terminus and a 3' XNA terminus.

In some aspects, an N-mer can comprise a reversible extension blocking group. A reversible extension blocking group is a chemical group that prevents ligation and/or extension at the terminus of the nucleic acid molecule to which it is attached and that can be removed, for example by exposure to light of a specific wavelength or to a particular chemical. In some aspects, a reversible extension blocking group can be a photo-liable blocking group or a 4,4'-dimethoxytrityl phosphate (DMT-PO$_4$). An N-mer can have a reversible blocking group at the 5' terminus. An N-mer can have a reversible blocking group at the 3' terminus. An N-mer can have a reversible blocking group at both the 5' and the 3' terminus. As used herein, the terms "blocking group" and "protecting group" are used interchangeably. As used herein, the terms "removing the blocking group" and "deprotecting" are used interchangeably.

In some aspects, the 5' end of an N-mer can be activated by 5' adenylation for subsequent ligation with appropriately selective enzymes.

N-mers as described herein can be used in any method of the present disclosure, as described herein.

Libraries of N-mers

In some aspects, the present disclosure provides a composition comprising a library of N-mers. A library of N-mers comprises a plurality of N-mer species such that there is at least one N-mer comprising every possible nucleic acid sequence for the given length of N-mers in the library. For example, in a library of N-mers, wherein the N-mers comprise 3 nucleotides (3-mer), there are 64 possible sequences of 3 nucleotides. Thus a 3-mer library of the present disclosure comprises at least 64 species of 3-criers. In another example, in a library of N-mers, wherein the N-mers comprise 4 nucleotides (4-mer), there are 256 possible sequences of 4 nucleotides. Thus, a 4-mer library of the present disclosure comprises at least 256 species of N-mers. In another example, in a library of N-mers, wherein the N-mers comprise 5 nucleotides (5-mer), there are 1024 possible sequences of 5 nucleotides. Thus, a 5-mer library of the present disclosure comprises at least 1024 species of N-mers. This can be extrapolated to libraries of N-mers with any number of nucleotides in each N-mer: a library of N-mers that comprise x nucleotides (x-mer) comprise at least $4^x$ different species of x-mers.

In some aspects, the present disclosure provides libraries of N-mers comprising all possible 3-mers (64), or 4-mers (256), or 5-mers (1024), or 6-mers (4096), or 7-mers (16, 384), or 8-mers (65,536), or 9-mers (262,144), or 10-mers (1,048,576), and so on and so forth, wherein the N-mers in the library comprise DNA, RNA, XNA or any combination thereof.

In some aspects, in libraries of the present disclosure, each species of N-mer can be present in the same amount. In some aspects, in libraries of the present disclosure, each species of N-mer can be present in different amounts. In some aspects, in libraries of the present disclosure, some species of N-mer are present in the same amount and other species of N-mer are present in different amounts.

Each N-mer in a library of N-mers can comprise any attribute or feature as described herein.

Libraries of N-mers as described herein can be used in any method of the present disclosure, as described herein.

Anchor Primers

In some aspects, the present disclosure provides compositions comprising anchor primer sequences. The terms "anchor primer sequences" and "anchor primers" are used interchangeably herein.

Anchor primer sequences can comprise a polynucleotide. Anchor primer sequences can comprise at least about 1 nucleotide, or at least about 2 nucleotides, or at least about 3 nucleotides, or at least about 4 nucleotides, or at least about 5 nucleotides, or at least about 6 nucleotides, or at least about 7 nucleotides, or at least about 8 nucleotides, or at least about 9 nucleotides, or at least about 10 nucleotides, or at least about 11 nucleotides, or at least about 12 nucleotides, or at least about 13 nucleotides, or at least about 14 nucleotides, or at least about 15 nucleotides, or at least about 16 nucleotides, or at least about 17 nucleotides, or at least about 18 nucleotides, or at least about 19 nucleotides, or at least about 20 nucleotides, or at least about 21 nucleotides, or at least about 22 nucleotides, or at least about 23 nucleotides, or at least about 24 nucleotides, or at least about 25 nucleotides, or at least about 26 nucleotides, or at least about 27 nucleotides, or at least about 28 nucleotides, or at least about 29 nucleotides, or at least about 30 nucleotides, or at least about 31 nucleotides, or at least about 32 nucleotides, or at least about 33 nucleotides, or at least about 34 nucleotides, or at least about 35 nucleotides, or at least about 40 nucleotides, or at least about 45 nucleotides, or at least about 50 nucleotides, or at least about 60 nucleotides, or about 70 nucleotides, or about 80 nucleotides, or about 90 nucleotides, or about 100 nucleotides.

In some aspects, an anchor primer sequence can comprise RNA. In some aspects, an anchor primer sequence can comprise DNA. In some aspects, an anchor primer sequence can comprise or consist of XNA. In some aspects, an anchor primer sequence can comprise DNA, RNA, XNA or any combination thereof. An anchor primer sequence can be wholly or partially comprised of DNA, RNA or XNA. An anchor primer sequence can be about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95% RNA. An anchor primer sequence can be about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95% DNA. An N-mer can be about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95% XNA.

In some aspects, an anchor primer sequence can be double-stranded. An anchor primer sequence can be single-stranded. An anchor primer sequence can be partially double-stranded. An anchor primer sequence can be partially single-stranded.

In some aspects, an anchor primer sequence can comprise a restriction endonuclease site. The terms "restriction endonuclease site" and "restriction site" are used interchangeably herein. In some aspects, an anchor primer sequence can comprise at least about 1 restriction site, or at least about 2 restriction sites, or at least about 3 restriction sites, or at least about 4 restriction sites, or at least about 5 restriction sites, or at least about 6 restriction sites, or at least about 7 restriction sites, or at least about 8 restriction sites, or at least about 9 restriction sites, or at least about 10 restriction sites.

In some aspects, an anchor primer sequence can comprise an EcoRI restriction site. In some aspects, an anchor primer sequence can comprise a MlyI restriction site. In some aspects, an anchor primer sequence can comprise an EcoRV restriction site. In some aspects, an anchor primer sequence can comprise a SbfI restriction site. Endonuclease restriction sites include, but are not limited to, AclI, HindIII, SspI, MluCI, PciI, AgeI, BspMI, BfuAI, SexAI, MluI, BceAI, HpyCH4IV, HpyCH4III, BaeI, BsaXI, AflIII, SpeI, BsrI, BmrI, BglII, AfeI, AluI, StuI, BspDI, ClaI, PI-SceI, NsiI, AseI, SwaI, CspCI, MfeI, Nb.BssSI, BssSaI, BmgBI, PmlI, AleI, EcoP15I, PvuII, AlwNI, BtsIMutI, NdeI, CviAII, FatI, NlaIII, MslI, FspEI, XcmI, BstXI, PflMI, BccI, NcoI, BseYI, FauI, TspMI, XmaI, SmaI, Nt.CviPII, LpnPI, AciI, SacII, BsrBI, HpaII, MspI, ScrFI, StyD41, BsaJI, BslI, BtgI, NciI, AvrII, MnlI, Nt.BbvCI, Nb.BbvCI, BbvCI, SbfI, Bpu10I, Bsu36I, EcoNI, HpyAV, BstNI, PspGI, StyI, BcgI, PvuI, BstBI, EagI, RsrII, BsiEI, BsiWI, BsmBI, Esp3I, Hpy99I, MspA 1I, AbaSI, MspJI, SgrAI, BfaI, BspCNI, XhoI, PaeR7I, EarI, AcuI, PstI, BpmI, DdeI, SfcI, AfI, BpuEI, SmiI, AvaI, BsoBI, MboII, BbsI, XmnI, BsmI, Nb.BsmI, EcoRI, HgaI, ZraI, AatII, Tth111I, PflFI, PshAI, Ahdi, DrdI, Eco53kI, SacI, BseRI, MlyI, PleI, Nt.BstNBI, HinfI, EcoRV, Sau3AI, MboI, DpnII, DpnI, BsaBI, TfiI, BsrDI, Nb.BsrDI, BbvI, Nb.BtsI, Btsαl, BstAPI, SfaNI, SphI, SrfI, NmeAIII, NaeI, NgoMIV, BglI, AsiS1, BtgZI, HhaI, HinP1I, BssHII, NotI, Fnu4HI, Cac8I, MwoI, BmtI, NheI, Nt.BspQI, BspQI, SapI, BlpI, TseI, ApeKI, Bsp1286I, AlwI, Nt.AlwI, BamHI, BtsCI, FokI, HacIII, FseI, SfiI, NarI, PluTI, SfoI, KasI, AscI, EciI, BsmFI, ApaI, PspOMI, Sau96I, NlaIV, KpnI, Acc65I, BsaI, HphI, BstEII, AvaII, BanI, BaeGI, BsaHI, BanII, CviQI, RsaI, BciVI, SalI, Nt.BsmAI, BcoDI, BsmAI, ApaLI, BsgI, AccI, Hpy166II, Tsp45I, HpaI, PmeI, HincII, BsiHKAI, TspRI, ApoI, ApoI-HF, NspI, BsrFαI, BstYI, HaeII, CviKI-1, EcoO109I, PpuMI, I-CeuI, SnaBI, I-SceI, BspHI, BspEI, MmeI, TaqαI, NruI, Hpy188I, Hpy188III, XbaI, BclI, BclI-HF, HpyCH4V, FspI, PI-PspI, MscI, BsrGI, MseI, PacI, PsiI, BstBI, DraI, PspXI, BsaWI, BsaAI or EacI sites. A restriction site can be a restriction site for offset cutting restriction enzymes, also called Type II S restriction endonuclease. A non-limiting example of a Type II S restriction endonuclease is the enzyme Mly1.

An anchor primer sequence can be directly or indirectly attached to a solid support. Attachments may be non-covalently mediated, such as by biotin and avidin interactions or may be covalent links, such as a range of 'click' chemistries. Attachments may include spacer molecules such as polyethylene glycol (PEG) or triethylene glycol (TEG).

An anchor primer sequence can comprise at least about 1, or at least about 2, or at least about 3, or at least about 4, or at least about 5, or at least about 6, or at least about 7, or at least about 8, or at least about 9, or at least about 10 abasic nucleic acid molecules. The terms "abasic nucleic acid molecule" and "abasic site" are used interchangeably herein. An abasic nucleic acid molecule is a nucleic acid molecule that has neither a purine nor a pyrimidine base. A polynucleotide comprising a basic nucleic acid molecule can be cleaved with DNA glycosylate-lyase endonuclease VIII.

An anchor primer sequence can comprise at least about 1, or at least about 2, or at least about 3, or at least about 4, or at least about 5, or at least about 6, or at least about 7, or at least about 8, or at least about 9, or at least about 10 deoxyuridine nucleic acid molecules. The terms "deoxyuridine nucleic acid molecules" and "deoxyuridine sites" are used interchangeably herein. A deoyuridine site can be transformed into an abasic by treatment with Uracil DNA glycosylase, then the resulting abasic site may be cleaved using DNA glycosylate-lyase endonuclease VIII.

An anchor primer sequence can comprise at least about 1, or at least about 2, or at least about 3, or at least about 4, or at least about 5, or at least about 6, or at least about 7, or at least about 8, or at least about 9, or at least about 10 deoxyinosine nucleic acid molecules. The terms "deoxyinosine nucleic acid molecule" and "deoxyinosine site" are used interchangeably herein. A deoxyinosine site can be cleaved with endonuclease V.

An anchor primer sequence can comprise a targeting nucleic acid sequence that is complementary to a guide RNA. The targeting nucleic acid sequence can then be cleaved by Cas9 and the complementary guide RNA.

In some aspects, anchor primers are designed to allow the specific removal of any additional sequence and/or nucleic acid fragment that has been extended from the end of the anchoring primer sequence. Specific removal of the additional sequence and/or nucleic acid fragment may be accomplished in several ways. In a non-limiting example, a restriction site located between the additional sequence/nucleic acid fragment and the anchor primer sequence can be cleaved with the appropriate restriction endonuclease. In some aspects, the restriction site located between the additional sequence/nucleic acid fragment and the anchor primer sequence can be formed by hybridizing a short reverse complementary oligonucleotide to the anchor primer sequence. In another non-limiting example, an abasic site located between the additional sequence/nucleic acid fragment and the anchor primer sequence can be cleaved using DNA glycosylate-lyase endonuclease VIII. In another non-limiting example, a deoxyuridine site located between the additional sequence/nucleic acid fragment and the anchor primer sequence can be first converted into an abasic site using Uracil DNA glycosylase, and the abasic site then cleaved using DNA glycosylate-lyase endonuclease VIII. In another non-limiting example, a deoxyinsone site between the additional sequence/nucleic acid fragment and the anchor primer sequence can be cleaved using endonuclease V.

Figures 2, 2A, 2B, 2C, 2D:
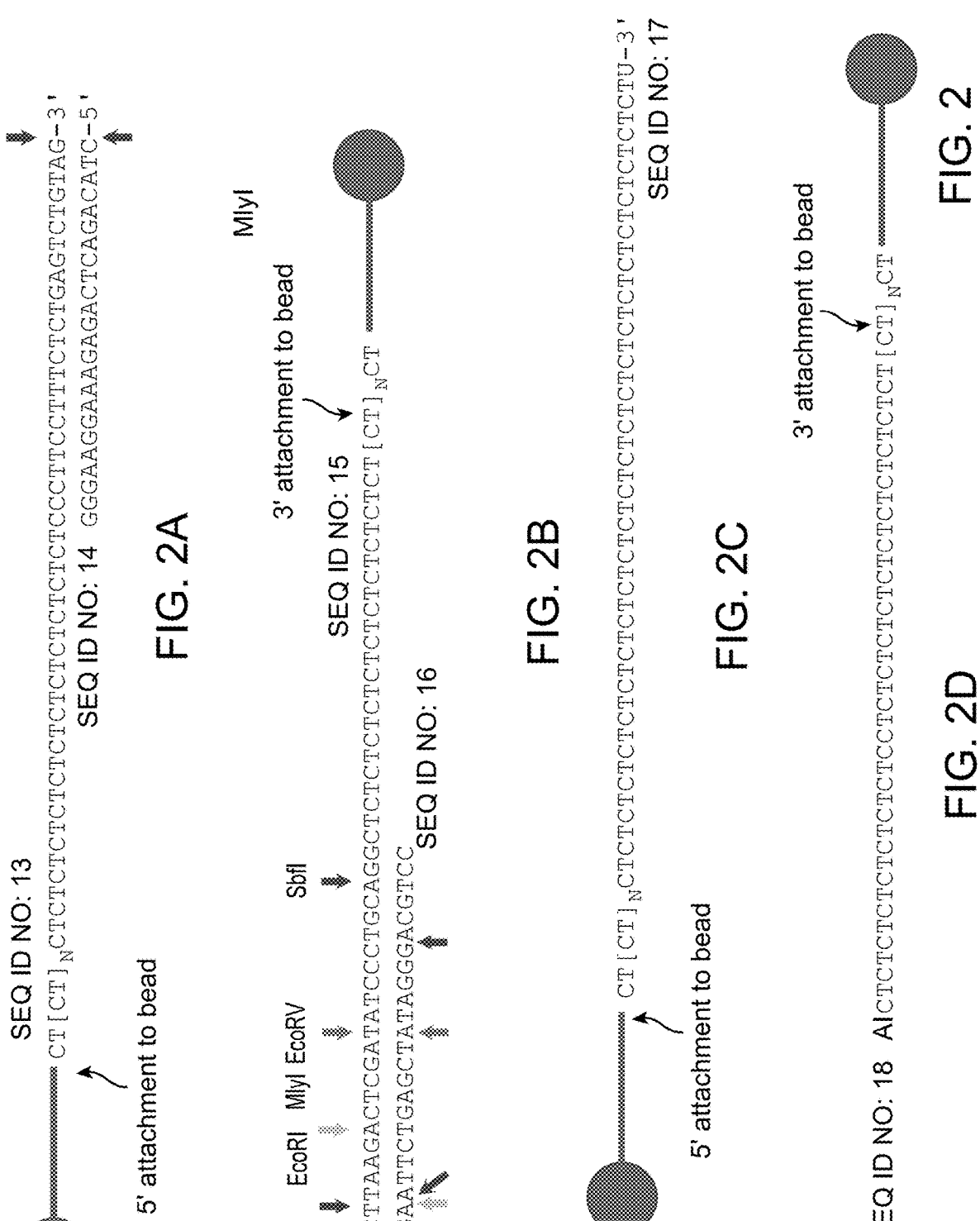
FIGS. 2A-D are a series of diagrams showing four different possible anchor primer sequences.

FIG. 2 shows four exemplary anchor primer sequences of the present disclosure attached to solid supports. In these non-limiting examples, the solid supports are beads.

FIG. 2A shows an anchor primer sequence for use in a 3' extension geometric synthesis method of the present disclosure. The anchor primer sequence comprises a low-complexity polynucleotide that is attached to the solid support bead at its 5' terminus. The 3' terminus is therefore exposed for ligation and extension of nucleic acid fragments. Hybridized to the anchor primer sequence is a short reverse complementary oligonucleotide. The short reverse complementary oligonucleotide is hybridized such that the resulting double-stranded structure comprises a MlyI restriction site, shown in red font.

FIG. 2B shows an anchor primer sequence for use in a 5' extension geometric synthesis method of the present disclosure. The anchor primer sequence comprises a low-complexity polynucleotide that is attached to the solid support bead at its 3' terminus. The 5' terminus is therefore exposed for ligation and extension of nucleic acid fragments. Hybridized to the anchor primer sequence is a short reverse complementary oligonucleotide. The short reverse complementary oligonucleotide is hybridized such that the resulting double-stranded structure comprises a MlyI restriction site (shown in red font), an EcoRI restriction site (shown in green font), an EcoRV (shown in blue font) and a SbfI site (shown in purple font).

FIG. 2C shows an anchor primer sequence for use in a 3' extension geometric synthesis method of the present disclosure. The anchor primer sequence comprises a low-complexity polynucleotide that is attached to the solid support bead at its 5' terminus. The 3' terminus is therefore exposed for ligation and extension of nucleic acid fragments. The anchor primer sequence comprises a deoxyuridine site (U) at the 3' terminus (shown in red) that can be transformed into an abasic site through the activity of Uracil DNA glycosylase. The resulting abasic site may then be cut using DNA glycosylate-lyase endonuclease VIII.

FIG. 2D shows an anchor primer sequence for use in a 5' extension geometric synthesis method of the present disclosure. The anchor primer sequence comprises a low-complexity polynucleotide that is attached to the solid support bead at its 3' terminus. The 5' terminus is therefore exposed for ligation and extension of nucleic acid fragments. The anchor primer sequence comprises a combination of deoxyadenosine (A) and deoxyinosine (I) at the 5' terminus (shown in red font) that can be cleaved by Endonuclease V.

Anchor primers as described herein can be used in any method of the present disclosure, as described herein.

Solid Supports

In some aspects, the present disclosure provides compositions comprising solid supports. Solid supports can include, but are not limited to, magnetic microscopic beads or non-magnetic microscopic beads. The beads can comprise polyacrylamide, polystyrene, crosslinked agarose, or other similar materials. Solid supports can include, but are not limited to, plastic or glass surfaces, such as the surfaces of wells of multi-well plates. In some aspects, solid supports may be treated to enhance the nucleic acid binding properties or permit specific enzymatic activities. In some aspects, solid supports may be treated to prevent non-specific or un-wanted binding.

In some aspects, a solid support of the present disclosure can comprise a plurality of chambers. The chambers can be arranged in a grid. For example, a solid support of the present disclosure can be a 6, 12, 24, 48, 96, 384 or 1536 well microplate. Chambers can be hold an array of beads with attached anchor primers.

In some aspects, a solid support of the present disclosure can be connected to a microfluidic system for the delivery of reagents.

Solid supports as described herein can be used in any method of the present disclosure, as described herein.

Overlapping Sets of Nucleic Acid Fragments

The present disclosure provides a composition comprising a set of overlapping nucleic acid fragments. A set of overlapping nucleic acid fragments can comprise a plurality of nucleic acid fragments. Each nucleic acid fragment in the plurality of nucleic acid fragments can comprise at least about 2, or at least about 5, or at least about 10, or at least about 20, or at least about 25, or at least about 30, or at least about 35, or at least about 40, or at least about 45, or at least about 50, or at least about 55, or at least about 60, or at least about 65, or at least about 70, or at least about 75, or at least about 80, or at least about 85, or at least about 90, or at least about 95, or at least about 100, or at least about 105, or at least about 110, or at least about 115, or at least about 120, or at least about 125, or at least about 130, or at least about 135, or at least about 140, or at least about 145, or at least about 150 nucleotides. In some aspects, each nucleic acid fragment in the plurality of nucleic acid fragments can comprise at least about 96 nucleotides.

In a set of overlapping nucleic acid fragments, a first nucleic acid fragment can comprise a first region that is complementary to a second nucleic acid fragment, the second nucleic acid fragment can comprise a first region that is complementary to the first nucleic acid fragment and a second region that is complementary to a third nucleic acid fragment, the third nucleic acid fragment can comprise a first region that is complementary to the second nucleic acid fragment and a second region that is complementary to a fourth nucleic acid fragment, and so on and so forth. The regions of a nucleic acid fragment that are complementary to another nucleic acid fragment in a set can be referred to as the overlap regions. The overlap regions can comprise at least about 1 nucleotide, or at least about 2 nucleotides, or at least about 3 nucleotides, or at least about 4 nucleotides, or at least about 5 nucleotides, or at least about 6 nucleotides, or at least about 7 nucleotides, or at least about 8 nucleotides, or at least about 9 nucleotides, or at least about 10 nucleotides, or at least about 11 nucleotides, or at least about 12 nucleotides, or at least about 13 nucleotides, or at least about 14 nucleotides, or at least about 15 nucleotides, or at least about 16 nucleotides, or at least about 17 nucleotides, or at least about 18 nucleotides, or at least about 19 nucleotides, or at least about 20 nucleotides, or at least about 21 nucleotides, or at least about 22 nucleotides, or at least about 23 nucleotides, or at least about 24 nucleotides, or at least about 25 nucleotides, or at least about 26 nucleotides, or at least about 27 nucleotides, or at least about 28 nucleotides, or at least about 29 nucleotides, or at least about 30 nucleotides, or at least about 31 nucleotides, or at least about 32 nucleotides, or at least about 33 nucleotides, or at least about 34 nucleotides, or at least about 35 nucleotides, or at least about 40 nucleotides, or at least about 45 nucleotides, or at least about 50 nucleotides, or at least about 60 nucleotides. In some aspects, the overlap regions can comprise 24 nucleotides.

The regions of a nucleic acid fragment that are not complementary to another nucleic acid fragment can comprise at least about 30 nucleotides, or at least about 31 nucleotide, or at least about 32 nucleotides, or at least about 33 nucleotides, or at least about 34 nucleotides, or at least about 35 nucleotides, or at least about 36 nucleotides, or at least about 37 nucleotides, or at least about 38 nucleotides, or at least about 39 nucleotides, or at least about 40 nucleotides, or at least about 41 nucleotides, or at least about 42 nucleotides, or at least about 43 nucleotides, or at least about 44 nucleotides, or at least about 45 nucleotides, or at least about 46 nucleotides, or at least about 47 nucleotides, or at least about 48 nucleotides, or at least about 49 nucleotides, or at least about 50 nucleotides, or at least about 51 nucleotides, or at least about 52 nucleotides, or at least about 53 nucleotides, or at least about 54 nucleotides, or at least about 55 nucleotides, or at least about 56 nucleotides, or at least about 57 nucleotides, or at least about 58 nucleotides, or at least about 59 nucleotides, or at least about 60 nucleotides, or at least about 61 nucleotides, or at least about 62 nucleotides, or at least about 63 nucleotides, or at least about 64 nucleotides, or at least about 65 nucleotides, or at least about 70 nucleotides, or at least about 75 nucleotides, or at least about 80 nucleotides, or at least about 85 nucleotides.

Overlapping sets of nucleic acid fragments as described herein can be used in any method of the present disclosure, as described herein.

In some aspects, in a set of overlapping nucleic acid fragments, at least one of the nucleic acid fragments can be a chimeric nucleic acid fragment comprising a deoxyribose 5' (DNA) terminus and a ribose 3' (RNA) terminus. In some aspects, at least one of the nucleic acid fragments can be a chimeric nucleic acid fragment comprising a deoxyribose 3' (DNA) terminus and a ribose 5' (RNA) terminus. In some aspects, at least one of the nucleic acid fragments can be a chimeric nucleic acid fragment comprising a deoxyribose 5' (DNA) terminus and a deoxyribose 3' (DNA) terminus. In some aspects, at least one of the nucleic acid fragments can be a chimeric nucleic acid fragment comprising a ribose 5' (RNA) terminus and a ribose 3' (RNA) terminus.

In some aspects, the nucleic acid fragments in a set of overlapping nucleic acid fragments can be an N-mer of the present disclosure.

Methods of the Present Disclosure

Geometric Synthesis

The present disclosure provides methods of geometric synthesis of nucleic acid sequences. Methods of geometric synthesis include a geometric 3' method (also referred to as the 3' extension geometric synthesis method), a geometric 5' (also referred to as the 5' extension geometric synthesis method) method, a geometric transposase method, a geometric 3',5' co-synthesis method (also referred to as the 5' extension and 3' extension geometric co-synthesis), a 3' extension parallel synthesis method and a 5' extension parallel synthesis method.

Figure 15:
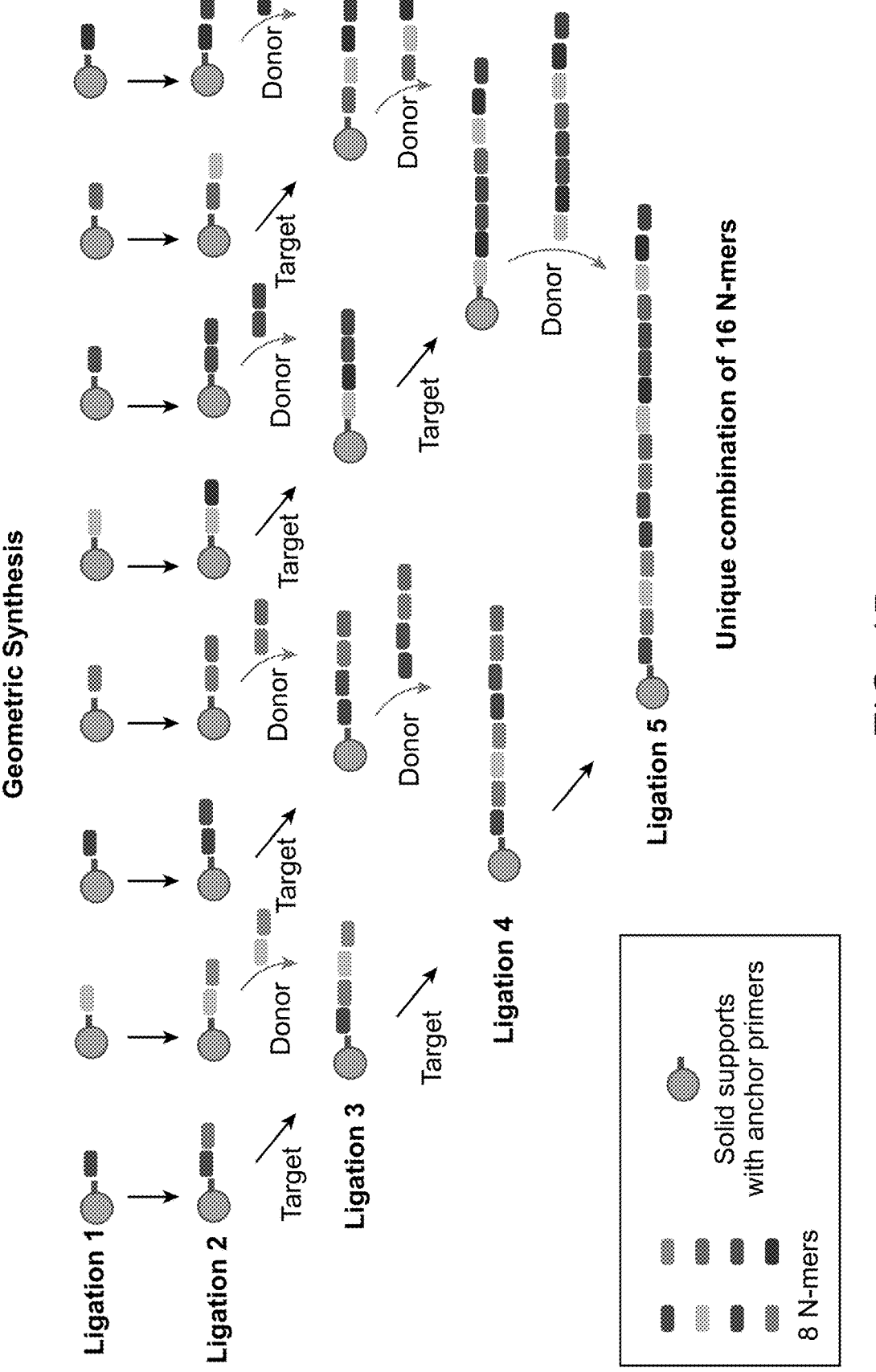
FIG. 15 is a schematic overview of geometric synthesis. In this example, eight different N-mers and the solid substrate bound anchor primer sequences are the starting materials.

FIGS. 1 and 15 depict a schematic overview of the geometric synthesis methods of the present disclosure. First a plurality of N-mers as described above is provided. In FIGS. 1 and 15, there are 8 different N-mer species provided. Also provided are anchor primers that are attached to solid supports. In Ligation 1, a single N-mer is ligated onto the anchor primers that are attached to the solid support to create a N-men-anchor primer complex. In Ligation 2, a second N-mer is ligated to the exposed end of the first N-mer to extend the first N-mer and create a N-mer₂-anchor primer complex. After ligation, a subset of the N-mer₂-anchor primer complexes are designated to be donor samples and the other subset of the N-mer₂-anchor primer complexes are designated to be target samples. The ligated N-mers are cleaved from the anchor primers in the donor samples, releasing a nucleic acid fragment that comprises two ligated N-mers. In ligation 3, the released nucleic acid fragments are then ligated onto the exposed end of an N-mer in a target sample to extend the target sample N-mer₂-anchor primer complex, thereby forming a N-mer₄-anchor primer complex. After ligation, a subset of the N-mer₄-anchor primer complexes are designated to be donor samples and the other subset of the N-mer₄-anchor primer complexes are designated to be target samples. The ligated N-mers are cleaved from the anchor primers in the donor samples, releasing a nucleic acid fragment that comprises four ligated N-mers. In ligation 4, the released nucleic acid fragments are then ligated onto the exposed end of an N-mer in a target sample to extend the target sample N-mers-anchor primer complex, thereby forming a N-mers-anchor primer complex. After ligation, a subset of the N-mers-anchor primer complexes are designated to be donor samples and the other subset of the N-mers-anchor primer complexes are designated to be target samples. The ligated N-mers are cleaved from the anchor primers in the donor samples, releasing a nucleic acid fragment that comprises eight ligated N-mers. In ligation 5, the released nucleic acid fragments are then ligated onto the exposed end of an N-mer in a target sample to extend the target sample N-men-anchor primer complex, thereby forming a N-mer₁₆-anchor primer complex.

3' Extension Geometric Synthesis

The present disclosure provides a 3' extension geometric synthesis method. A 3' extension geometric synthesis method is a geometric synthesis as described in FIGS. 1 and 15, wherein the anchor primers are attached to the solid support via their 5' termini, thereby leaving their 3' termini exposed for ligation and extension.

In a 3' extension geometric synthesis method, a plurality of N-mers as described above is provided, wherein the N-mers comprise a —PO₄ group at the 3' terminus and the 5' terminus. Also provided are anchor primers that are attached to a solid support via their 5' terminus. Thus, the 3' termini of the anchor primers, which comprise an —OH group, are exposed for ligation and extension.

A 3' extension geometric synthesis method can comprise the steps:

1) ligating an N-mer species onto the exposed 3' terminus of the anchor primers:

2) optionally incubating the ligation products from step (1) with a 3' to 5' specific exonuclease, such as Klenow polymerase, to remove un-ligated anchor primers from the solid supports. A polymerase such as a Klenow polymerase cannot digest nucleic acid molecules comprising a 3'-PO₄ group;

3) incubating the samples from step (2) with a phosphatase, such as calf intestinal alkaline phosphatase (CIP) or shrimp alkaline phosphatase (SAP) to remove the 3'-PO₄ from the ligated N-mers;

4) ligating a second N-mer to the 3' terminus of an N-mer ligated in step 1:

5) optionally incubating the ligation products from step (4) with a 3' to 5' specific exonuclease, such as Klenow polymerase, to remove un-ligated anchor primers from the solid supports;

6) designating a subset of the samples from step (5) as donor samples and a subset of samples from step (5) as target samples;

7) incubating the target samples from step (6) with a phosphatase such as calf intestinal alkaline phosphatase (CIP) or shrimp alkaline phosphatase (SAP) to remove 3'-PO₄ groups:

8) releasing the ligated N-mers in the donor samples from the anchor primer to which they are ligated, wherein releasing preserves both 3' and 5'-PO₄ groups;

9) ligating the released ligated N-mers from step (8) to the target samples from step (7);

10) repeating steps 5-9 with the ligation products from step (9).

In a 3' extension geometric synthesis method, step (10) can be repeated until the desired nucleic acid fragment has been synthesized. The desired nucleic acid fragment can then be released from the anchor primer to which it is ligated.

FIGS. 3-8 show a schematic overview of an exemplary synthesis of a nucleic acid molecule using a 3' extension geometric synthesis method of the present disclosure. The nucleic acid to be synthesized comprises a fragment of the *Aequorea victoria* green-fluorescent protein (GFP). FIG. 3A shows the entire coding region of the *A. victoria* GFP. The fragment to be synthesized is depicted in colored font and comprises a portion of the sequence:

```
                                              (SEQ ID NO: 1)
TACACACGAATAAAAGATAACAAAGATGAGTAAAGGAGAAGAACTTTTC

ACTGGAGTTGTCCCAATTCTTGTTGAATTAGATGGCGATGTTAATGGGC

AAAAATTCTCTGTCAGTGGAGAGGGTGAAGGTGATGCAACATACGGAAA

ACTTACCCTTAAATTTATTTGCACTACTGGGAAGCTACCTGTTCCATGG

CCAACACTTGTCAC.
```

The fragment to be synthesized is subdivided into eight N-mers, wherein each N-mer comprises 21 nucleotides. The N-mers are depicted in different colored font in FIG. 3A. The rest of the *A. victoria* GFP sequence can also be subdivided into N-mers comprising 21 nucleotides.

For the purposes of explaining this example, each N-mer is assigned an identifier code as shown in Table 1.

TABLE 1

| N-mer sequences and identifier codes | | |
|---|---|---|
| Identifier code | Sequence | SEQ ID NO |
| 1aA1 | TACACACGAATAAAAGATAAC | 2 |
| 1aA2 | ACTTTTCACTGGAGTTGTCCC | 3 |
| 1aA3 | CGATGTTAATGGGCAAAAATT | 4 |
| 1aA4 | AGGTGATGCAACATACGGAAA | 5 |
| 1bA1 | AAAGATGAGTAAAGGAGAAGA | 6 |
| 1bA2 | AATTCTTGTTGAATTAGATGG | 7 |
| 1bA3 | CTCTGTCAGTGGAGAGGGTGA | 8 |
| 1bA4 | ACTTACCCTTAAATTTATTTG | 9 |

Figure 4:
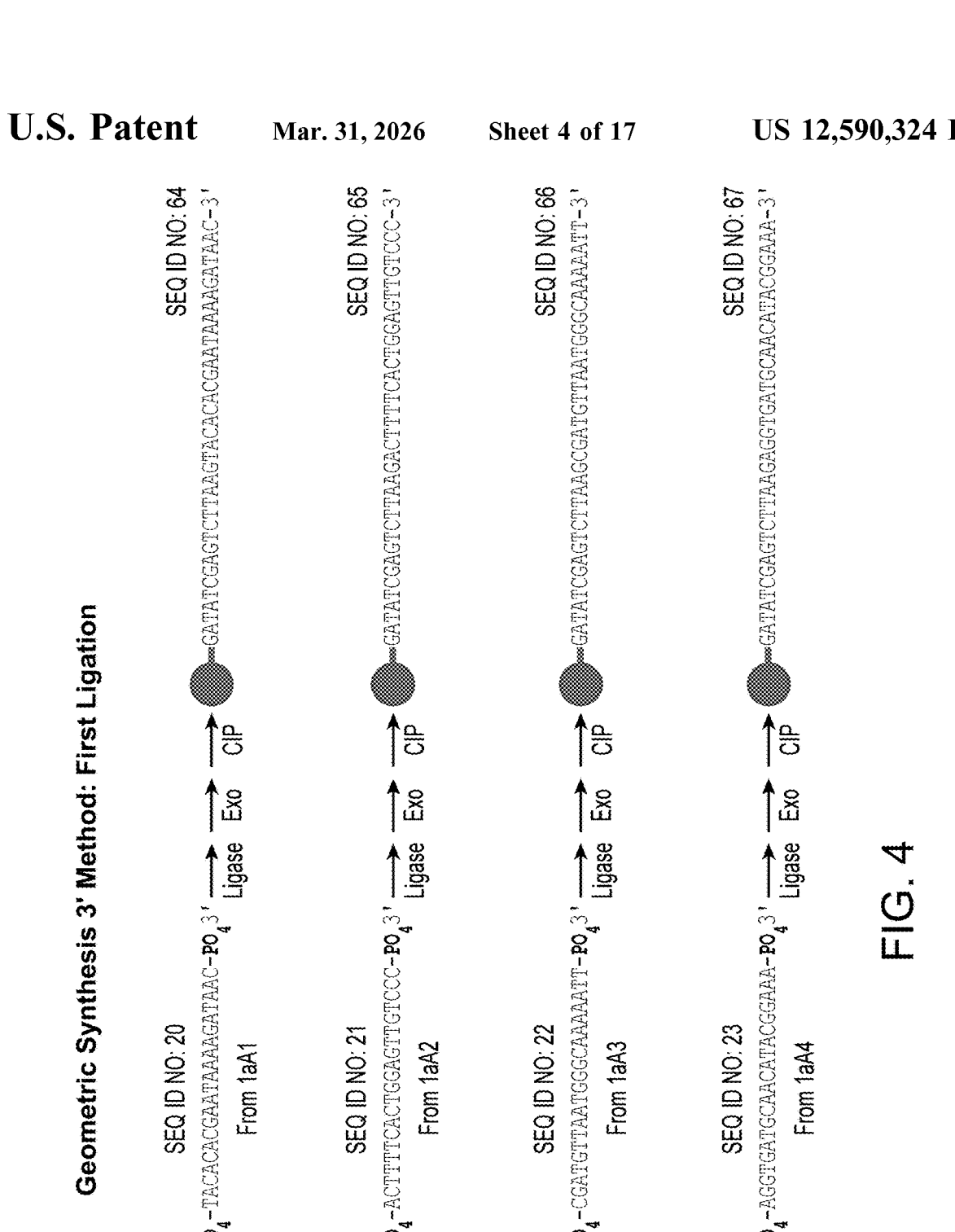
FIG. 4 is a schematic representation of the first ligation step. In this example the wells 1A1, 1A2, 1A3 and 1A4 receive a 21-mer fragment with 3' and 5'-PO$_4$, ligase is added to the reactions. After ligation Kienow polymerase with 3'-5' exonuclease activity is added to remove un-ligated anchor primers. Finally, calf intestinal alkaline phosphatase (CIP) is added to remove 3'-PO$_4$ groups to prepare the NA for the second round of ligation.

The synthesis method continues by providing a plurality of anchor primers attached to solid supports, as shown in FIG. 4. In this example, the solid supports are beads and the anchor primers comprise the sequence GATATCGAGTCT-TAAG (SEQ ID NO: 10).

N-mers 1aA1, 1aA2, 1aA3, and 1aA4 are then provided with a 3' and a 5'-PO$_4$ group. N-mers 1aA1, 1aA2, 1aA3, and 1aA4 are then ligated onto the exposed 3' end of the anchor primers as shown in FIG. 4. Following ligation, a polymerase with 3'-5' exonuclease activity, such as klenow polymerase, is added to remove any un-ligated anchor primers. Calf intestinal alkaline phosphatase (CIP) is then added to remove the 3'-PO$_4$ group on each of the ligated fragments. This step of synthesis results in nucleic acid fragments comprising the anchor primer and one of N-mers 1aA1, 1aA2, 1aA3, and 1aA4 attached to a solid bead, as shown in the right panel of FIG. 4.

Figure 5:
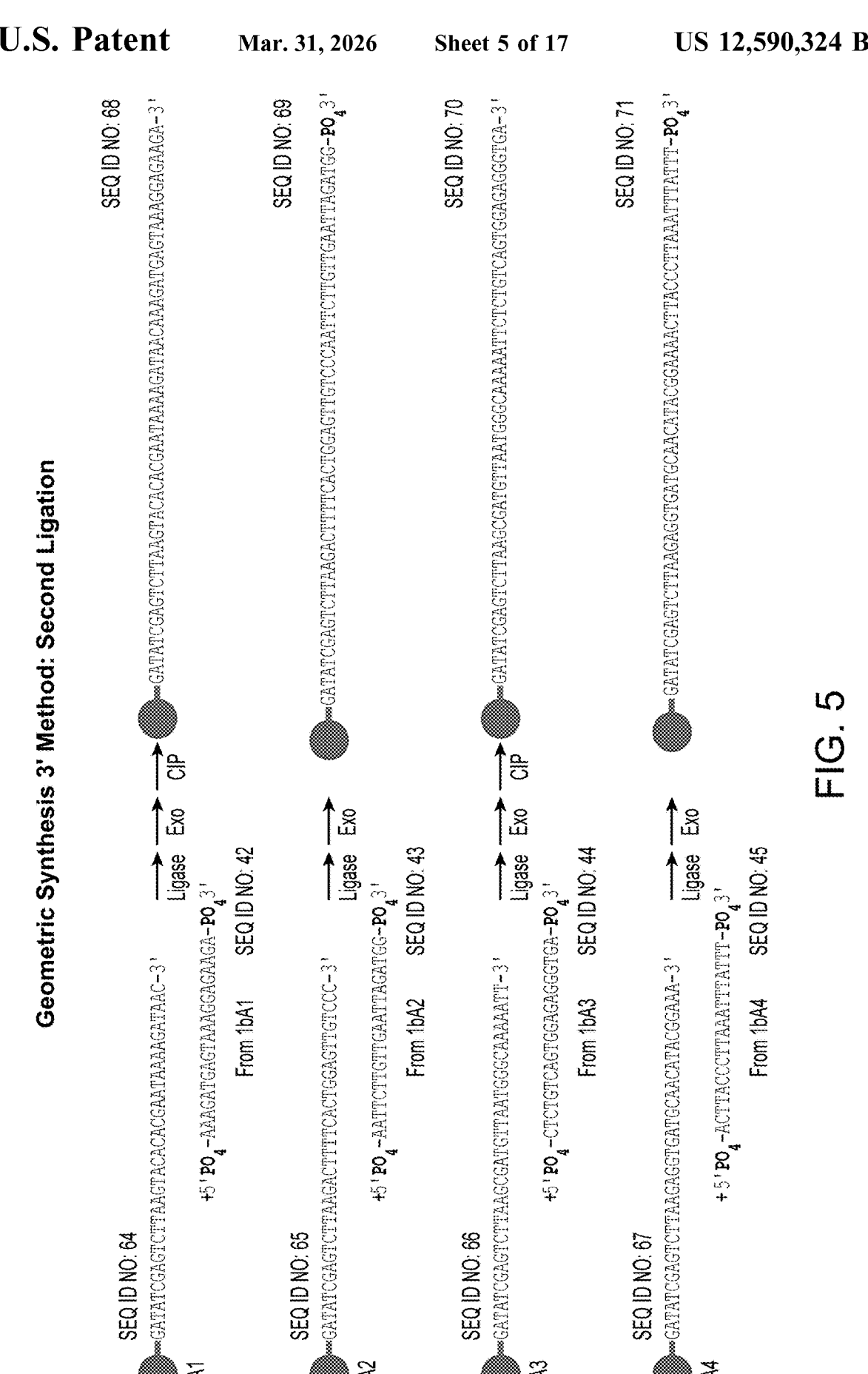
FIG. 5 is a schematic representation of the second ligation step. As with the first ligation step, the wells 1A1, 1A2, 1A3 and 1A4 each receive a 21-mer fragment bearing 3' and 5'-PO$_4$ groups, ligase is added to the reactions. After elongation by ligation, Kienow polymerase with exonuclease activity is added to remove un-ligated anchor primers. Finally, calf intestinal alkaline phosphatase (CIP) is added to 1A1 and 1A3 remove 3'-PO$_4$ groups to prepare the NA in those wells as targets for the next ligation. Wells 1A2 and 1A4 are left bearing 3'-PO$_4$ groups.

The synthesis method continues in FIG. 5. N-mer 1bA1, 1bA2, 1bA3 and 1bA4 are then provided with a 3' and a 5'-PO$_4$ group. The 5' end of N-mer 1bA1 is ligated onto the 3' end of N-mer 1aA1, the 5' end of N-mer 1bA2 is ligated onto the 3' end of N-mer 1aA2, the 5' end of N-mer 1bA3 is ligated onto the 3' end of N-mer 1aA3, the 5' end of N-mer 1bA4 is ligated onto the 3' end of N-mer 1aA4, as shown in the left panel of FIG. 5. Following ligation, a polymerase with 3'-5' exonuclease activity, such as klenow polymerase, is added to remove any un-ligated anchor primers. For the ligated 1aA1-1bA1 fragment and the ligated 1aA3-1bA3 fragment, Calf intestinal alkaline phosphatase (CIP) is then added to remove the 3'-PO$_4$ group on each of the ligated fragments. This step of synthesis results in the following nucleic acid fragments ligated to an anchor primer which is attached to a solid bead: a 1aA1-1bA1 fragment (1A1 fragment), a 1aA2-1bA2 fragment (1A2 fragment), a 1aA3-1bA3 fragment (1A3 fragment) and a 1aA4-1bA4 fragment (1A4 fragment). The anchor primer-1aA1-1bA1 fragment and the anchor primer-1aA3-1bA3 fragment do not have a 3'-PO$_4$ group. The anchor primer-1aA2-1bA2 fragment and the anchor primer-1aA4-1bA4 fragment do have a 3'-PO$_4$ group. The products of this synthesis step are shown in the right panel of FIG. 5.

Figure 6:
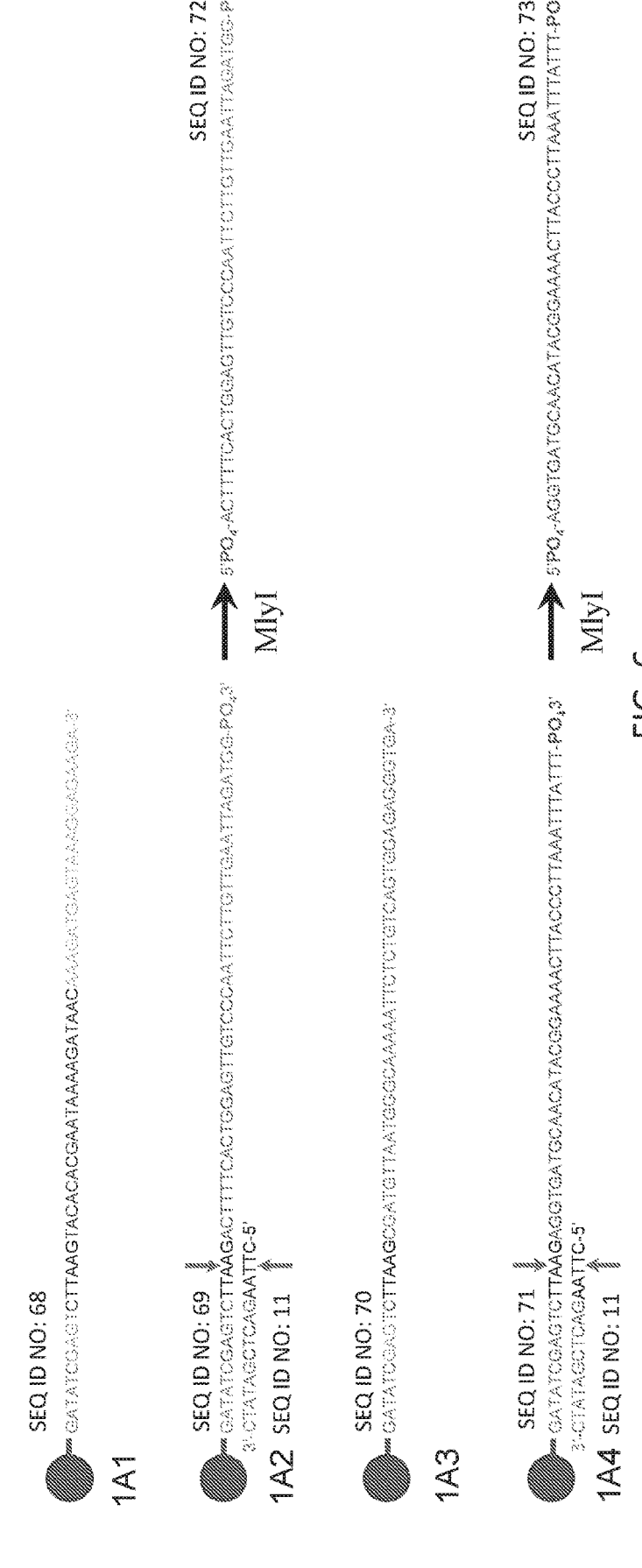
FIG. 6 is a schematic representation of the first release reaction. Donor samples 1A2 and 1A4 are first mixed with short reverse complementing oligo nucleotides, which generate double stranded MlyI sites on partially double stranded DNA. These samples are then digested with MlyI restriction endonuclease, at which point the released single stranded newly synthesized fragment is ready for ligation to the appropriate target sample. In this instance, the released fragment from 1A2 will be ligated to target sample 1A1 and the fragment from 1A4 will be ligated to target sample 1A3.

The synthesis method continues in FIG. 6. The 1A2 sample and the 1A4 samples are to be donor samples in the next synthesis round. Thus, a short reverse complementary oligonucleotide is mixed with the 1A2 sample and the 1A4 sample. The short reverse complementary oligonucleotide comprises the sequence CTATAGCTCAGAATfC (SEQ ID NO: 11) and is complementary to the anchor primer. The short reverse complementary oligonucleotide hybridizes to the anchor primer such that a double-stranded restriction endonuclease site is formed. In this example, the restriction endonuclease site is a MlyI restriction endonuclease site. After hybridization of the short reverse complementary oligonucleotide, the 1A2 sample and the 1A4 sample are incubated with MlyI restriction endonuclease, which cleaves at the MlyI restriction site, resulting in the release of the 1A2 fragment and 1A4 fragment.

Figure 7:
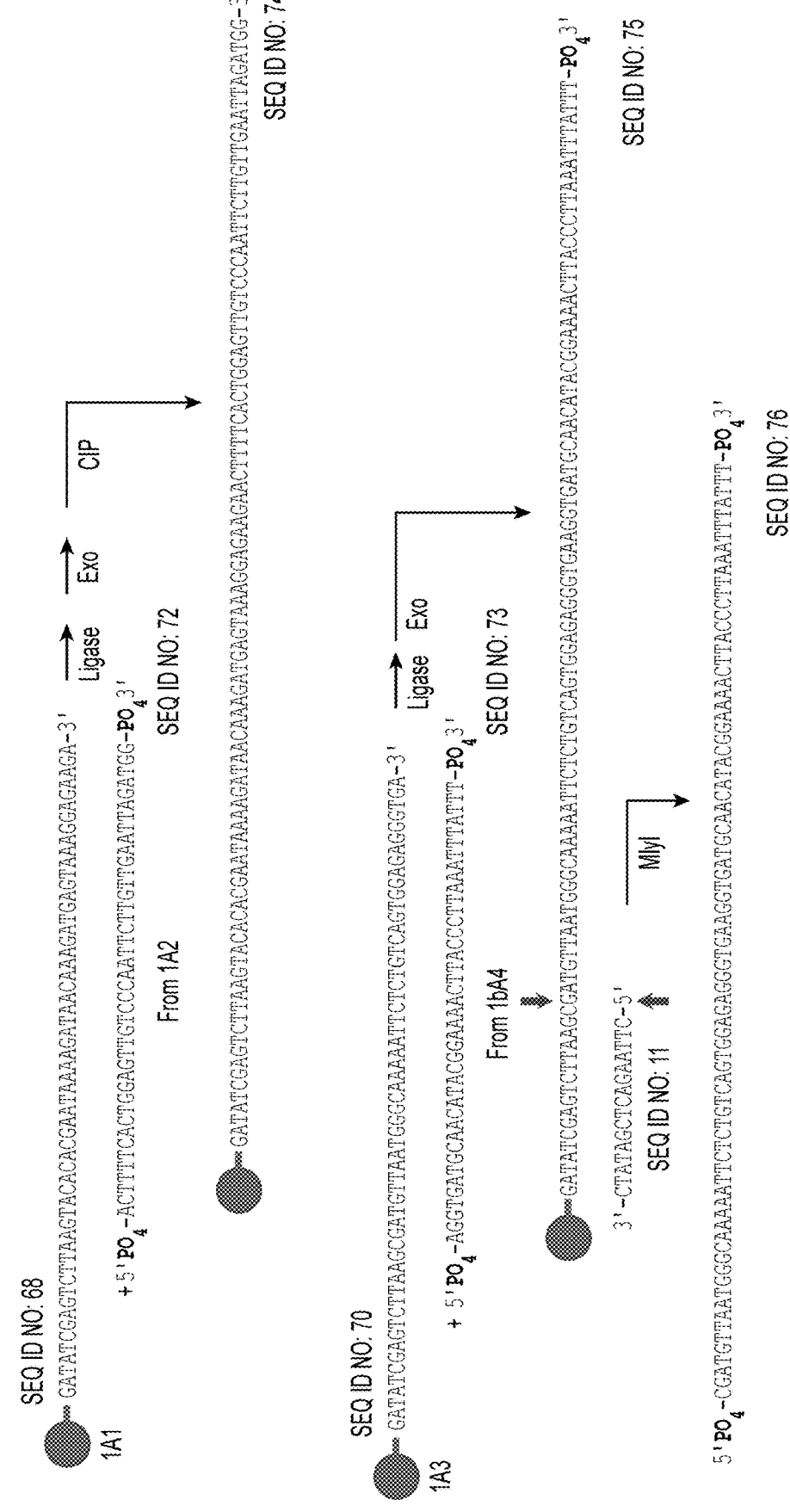
FIG. 7 is a schematic representation of the third ligation, which will combine extend the NA in 1A1 by ligation of the synthesized NA from 1A2, well as extend the NA of 1A3 by with the NA from 1A4. Finally, the product NA from 1A3 is released by cleavage with MlyI.

The synthesis method continues in FIG. 7. The 5' end of the 1A2 fragment is ligated onto the 3' end of the 1A1 fragment that is attached to the solid support to form a 1A1-1A2 fragment and the 5' end of the 1A4 fragment is ligated onto the 3' end of the 1A3 fragment that is attached to the solid support to form a 1A3-1A4 fragment. Following ligation, a polymerase with 3'-5' exonuclease activity, such as klenow polymerase, is added to remove any un-ligated anchor primers. For the ligated 1A1-1A2 fragment, Calf intestinal alkaline phosphatase (CIP) is then added to remove the 3'-PO$_4$ group on the fragment. The 1A3-1A4 fragment is then incubated with the short reverse complementary oligonucleotide, which hybridizes to the anchor primer to form a double-stranded restriction endonuclease site. In this example, the site is a MlyI site. After hybridization of the short reverse complementary oligonucleotide, the sample is incubated with MlyI restriction endonuclease, which cleaves the MlyI restriction site to release the 1A3-1A4 fragment, as shown in the bottom panel of FIG. 7.

Figure 8:
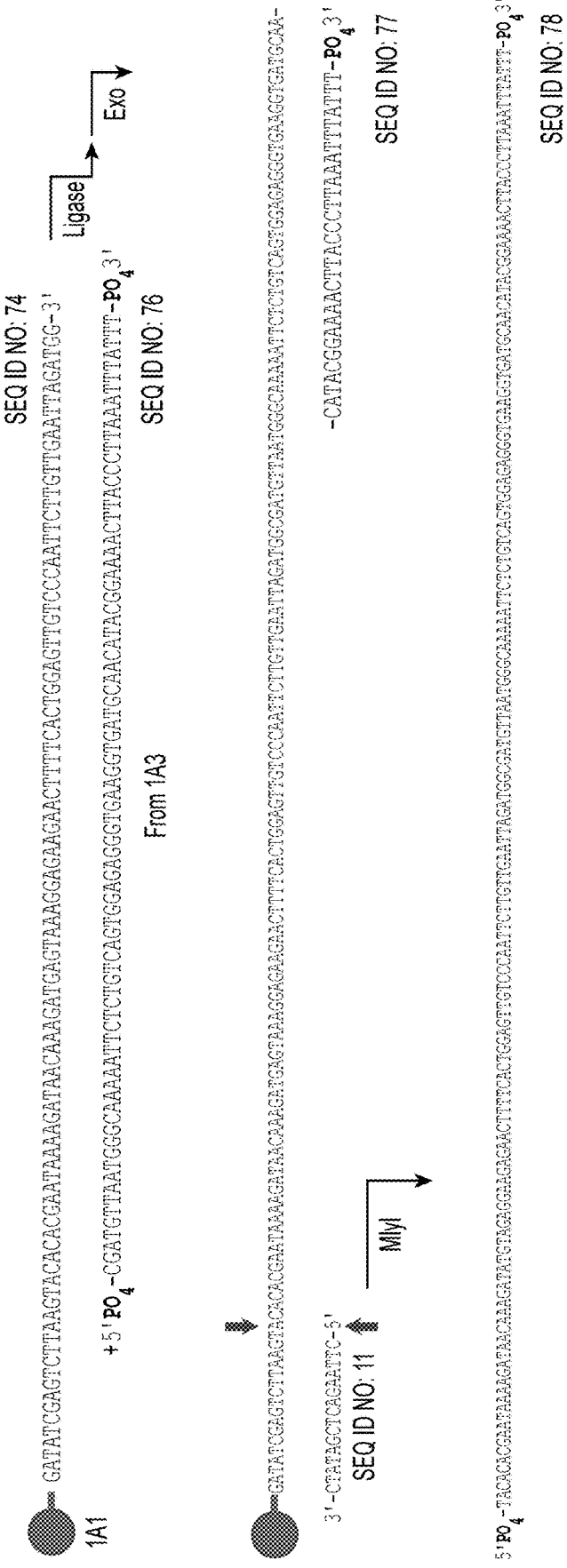
FIG. 8 is a schematic representation of the fourth and final ligation for this example. The NA product of sample 1A3 is ligated to the extended NA of well 1A1. After cleanup, the final product NA is released from solid supports by digestion with MlyI.
Figure 9:
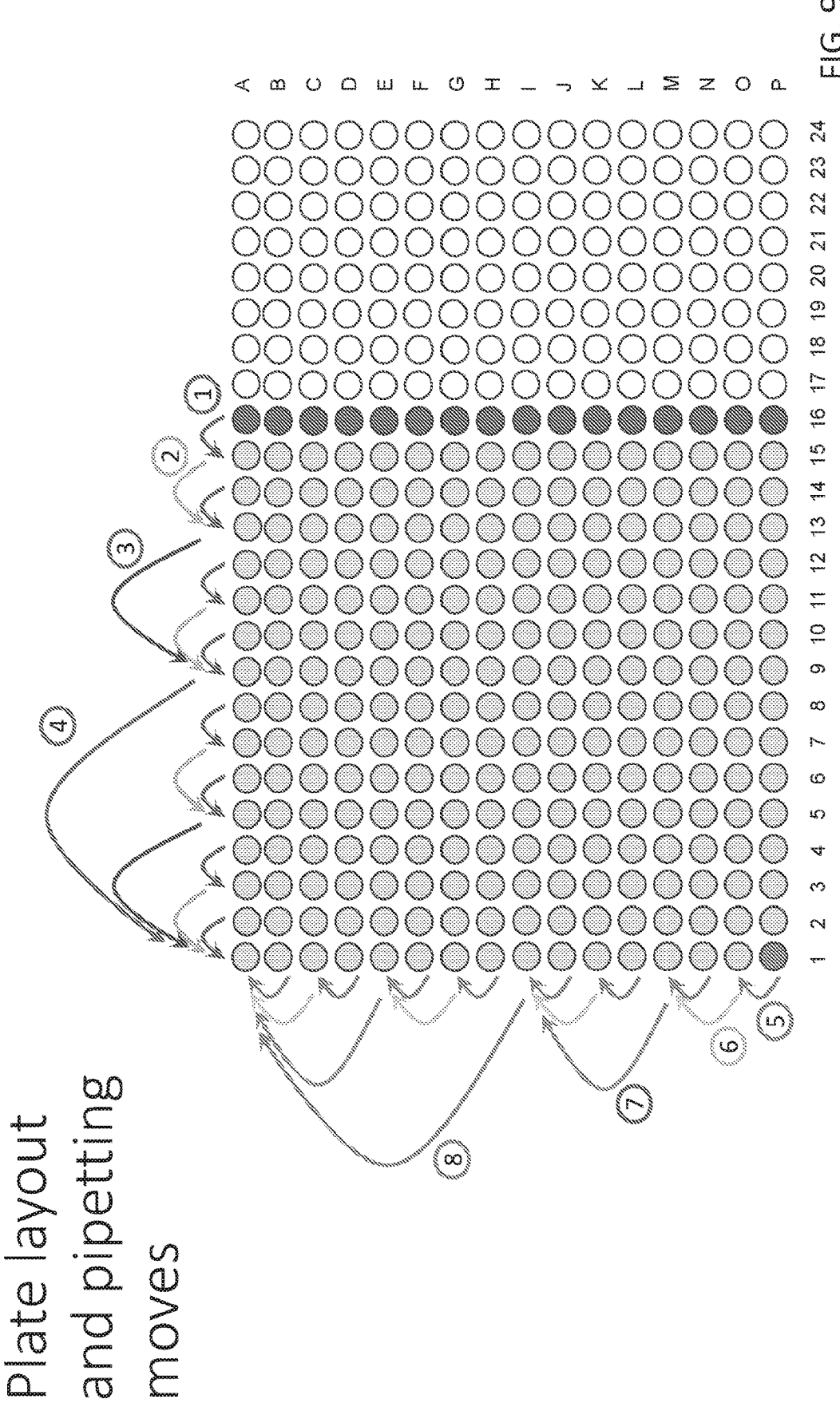
FIG. 9 shows a plate layout and pipetting moves. In this example, a 384 well plate is depicted with 16×16 wells (A1-P16) being used. There are two phases to the transfers. Firstly, column transfers (the initial column highlighted in red) take place over 4 cycles (after the initial addition of two N-mers to each well). In the first cycle column 16 well contents serve as donors for column 15, column 14 for column 13 and so on. In the second cycle, wells of column 15 serve as donors for column, etc. On cycle 4, column 9 wells serve as donors for column 1. In the second phase, all of the transfers occur within column 1. Firstly, for Cycle 5, well P1 (highlighted in green) serves as donor for well 01, well N1 for well M1 and so on. Ultimately well I1 is the donor for well A1 to yield a final product. If the starting N-mers were all 3-mers the final product would be 1536 bases long. Likewise with 5-mers the final product would be 2560 bases long.

The synthesis method continues in FIG. 8. The 5' end of the 1A3-1A4 fragment is ligated to the 3' end of the 1A1-1A2 fragment that is attached to the solid support to form a 1A1-1A2-1A3-1A4 fragment. Following ligation, a polymerase with 3'-5' exonuclease activity, such as klenow polymerase, is added to remove any un-ligated anchor primers. The 1A1-1A2-1A3-1A4 fragment is then incubated with short reverse complementary oligonucleotide, which hybridizes to the anchor primer to form a double-stranded restriction endonuclease site. In this example, the site is a MlyI site. After hybridization of the short reverse complementary oligonucleotide, the sample is incubated with MlyI restriction endonuclease, which cleaves the MlyI restriction site to release the 1A1-1A2-1A3-1A4 fragment (the fragment that was to be synthesized), as shown in the bottom panel of FIG. 8.

3' Extension Parallel Synthesis Method

The present disclosure provides a 3' extension parallel synthesis method. In a 3' extension parallel synthesis method, a plurality of 3' extension geometric synthesis reactions, as described above, are performed using N-mers and/or anchor primers that comprise a reversible block on the 3'-OH group. The plurality of reactions can be performed on a solid support comprising chambers that are arranged in a two-dimensional grid. At different stages of synthesis, certain reactions are allowed to proceed by removing the reversible block on the 3'-OH group in a particular chamber within the grid, thereby allowing the user to control what N-mer is incorporated in each step.

In a non-liming example, a two-dimensional grid of reactions may begin with general attachment of 3' reversibly blocked anchor primers. If the incorporation of a specific N-mer, such as ACG, is required, then the region of the two-dimensional grid where the N-mer with the sequence ACG is required is unblocked, allowing the ACG N-mer to be incorporated only there. Such a process ensues for all 64 possible 3-mers suitably blocked at the 3' end. Any possible sequence combination can be manifest at any specific location on the grid.

In a non-limiting example, the reversible block may be removed by exposure to light. Thus, a two-dimensional grid of reactions may begin with general attachment of 3' reversibly blocked anchor primers. If the incorporation of a specific N-mer, such as ACG, is required, then the region of the two-dimensional grid where the N-mer with the sequence ACG is required is exposed to light, removing the reversible block in that region, allowing the ACG N-mer to be incorporated only there.

5' Extension Geometric Synthesis Method

The present disclosure provides a 5' extension geometric synthesis method. A 5' extension geometric synthesis method is a geometric synthesis as described in FIGS. 1 and 15, wherein the anchor primers are attached to the solid support via their 3' termini, thereby leaving their 5' termini exposed for ligation and extension. In some aspects of the 5' extension geometric synthesis method, a plurality of N-mers as described above is provided, wherein the N-mers comprise a —OH group at the 3' terminus and the 5' terminus. Also provided are anchor primers that are attached to a solid support via their 3' terminus. Thus, the 5' termini of the anchor primers, which comprise an —PO$_4$ group, are exposed for ligation and extension.

A 5' extension geometric synthesis method can comprise the steps:

1) ligating an N-mer species onto the exposed 5' terminus of the anchor primers:

2) optionally, incubating the ligation products from step (1) with a 5' to 3' specific exonuclease, such as lambda exonuclease, to remove un-ligated anchor primers from the solid supports. Lambda exonuclease cannot digest nucleic acid molecules comprising a 5'-OH group.

3) optionally incubating the samples from step (2) with polynucleotide kinase (PNK), to produce a —PO$_4$ group at each 5' terminus;

4) ligating a second N-mer to the 5' terminus of an N-mer ligated in step 1;

5) optionally, incubating the ligation products from step (4) with a 5' to 3' specific exonuclease, such as lambda exonuclease, to remove un-ligated anchor primers from the solid supports:

6) designating a subset of the samples from step (5) as donor samples and a subset of samples from step (5) as target samples;

7) optionally incubating the target samples from step (6) with polynucleotide kinase (PNK), to produce a —PO$_4$ group at each 5' terminus;

8) releasing the ligated N-mers in the donor samples from the anchor primer to which they are ligated, wherein releasing preserves both 3' and 5'-OH groups;

9) ligating the released ligated N-mers from step (8) to the target samples from step (7):

10) repeating steps 5-9 with the ligation products from step (9).

In a 5' extension geometric synthesis method, step (10) can be repeated until the desired nucleic acid fragment has been synthesized. The desired nucleic acid fragment can then be released from the anchor primer to which it is ligated.

In some aspects of the 5' extension geometric synthesis method of the present disclosure, a plurality of N-mers as described above is provided, wherein the N-mers comprise an —OH group at the 3' terminus and a —PO$_4$ at the 5' terminus. The —PO$_4$ group can be attached a protecting group.

5' Extension Parallel Synthesis Method

The present disclosure provides a 5' extension parallel synthesis method. In a 5' extension parallel synthesis method, a plurality of 5' extension geometric synthesis reactions, as described above, are performed using N-mers and/or anchor primers that comprise a reversible block on the 5'-PO$_4$ group. The plurality of reactions can be performed on a solid support comprising chambers that are arranged in a two-dimensional grid. At different stages of synthesis, certain reactions are allowed to proceed by removing the reversible block on the 5'-PO$_4$ group in a particular chamber within the grid, thereby allowing the user to control what N-mer is incorporated in each step.

In a non-liming example, a two-dimensional grid of reactions may begin with general attachment of 5' reversibly blocked anchor primers. If the incorporation of a specific N-mer, such as ACG, is required, then the region of the two-dimensional grid where the N-mer with the sequence ACG is required is unblocked, allowing the ACG N-mer to be incorporated only there. Such a process ensues for all 64 possible 3-mers suitably blocked at the 5' end. Any possible sequence combination can be manifest at any specific location on the grid.

In a non-limiting example, the reversible block may be removed by exposure to light. Thus, a two-dimensional grid of reactions may begin with general attachment of 5' reversibly blocked anchor primers. If the incorporation of a specific N-mer, such as ACG, is required, then the region of the two-dimensional grid where the N-mer with the sequence ACG is required is exposed to light, removing the reversible block in that region, allowing the ACG N-mer to be incorporated only there.

Geomantic Transposase Method

The present disclosure provides a geometric transposase method. A geometric transposase method comprises the use of a collection of plasmids with reverse oriented left and right terminal repeats derived from a precisely excising transposable element, such as piggyBac, as shown in the bottom panel FIG. 12. Each plasmid in the collection carries a different N-mer (e.g. a 3-, 4-, and 5-mers) that is flanked by reverse oriented left and right terminal repeats. An N-mer flanked by reverse oriented left and right terminal repeats is herein referred to as a transposable N-mer.

Figure 12:
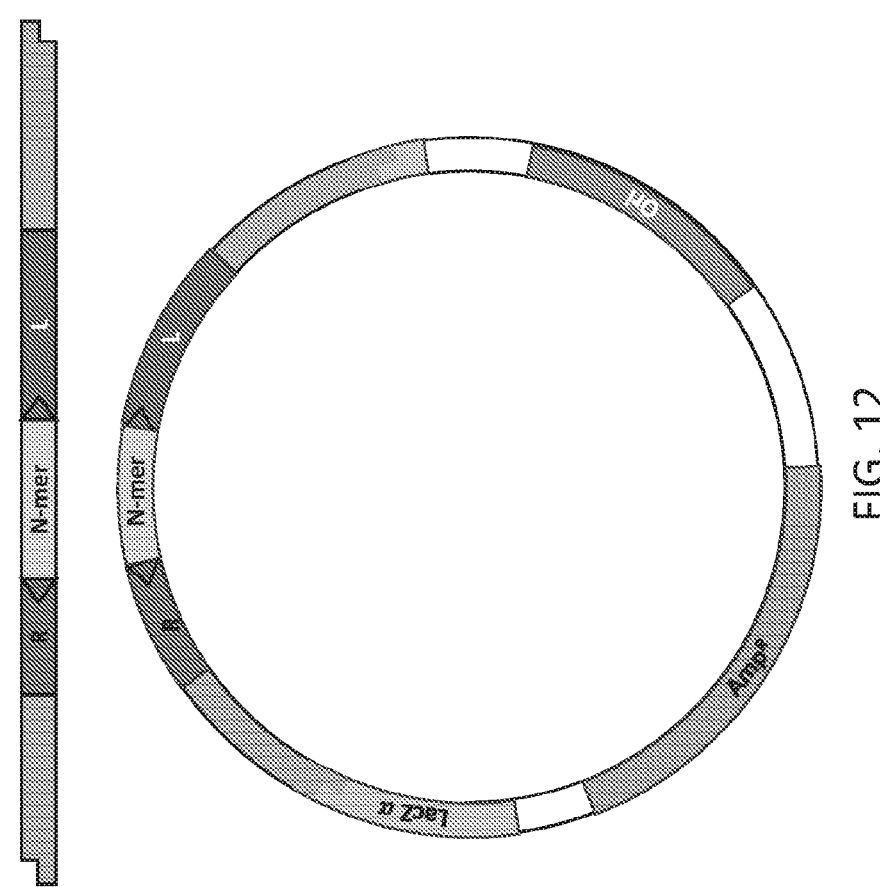
FIG. 12 is a generic plasmid map for transposase mediated geometric synthesis. The plasmid carries a modified transposable element. Instead of the normal orientation of the left (green with purple triangle) and right (red with purple triangle) inverted terminal repeat (ITR) sequences, here the ITRs are reverse oriented with the N-mer sequence between them. Sequence to the left and to the right of the ITRs (grey) is present to fulfill a requirement for a minimal transposable element size plus an appropriate restriction endonuclease site. In addition to the transposable element and N-mer sequences the construct also has a backbone plasmid, such as pUC19 carrying a LacZ alpha gene with a multiple cloning site, an origin of replication and a selectable marker such as an ampicillin resistance gene.

In a geometric transposase method, each required transposable N-mer is excised from its plasmid backbone by an appropriate restriction endonuclease (RE) or similar digestion along with the flanking reverse oriented left and right terminal repeats, as shown in the top panel of FIG. 12. A plurality of anchor primers attached to a solid support are then provided.

In some aspects, a geometric transposase method can comprise:

1) ligating a transposable N-mer to an anchor primer attached to a solid support:

2) optionally, cleaning up the reaction from step (1);

3) ligating a second transposable N-mer to a transposable N-mer ligated in step (1);

4) optionally, cleaning up the reaction from step (3);

5) incubating the products of step (4) with a transposase to excise the intervening sequence between the two ligated N-mer sequences;

6) designating a subset of the samples from step (5) as donor samples and a subset of samples from step (5) as target samples;

7) releasing the N-mers in the donor samples from the anchor primer to which they are ligated;

8) ligating the released ligated N-mers from step (8) to target samples from step (7);

9) cleaning up the reaction from step (8);

10) repeating steps 5-9 with the products of step (9).

Figure 13:
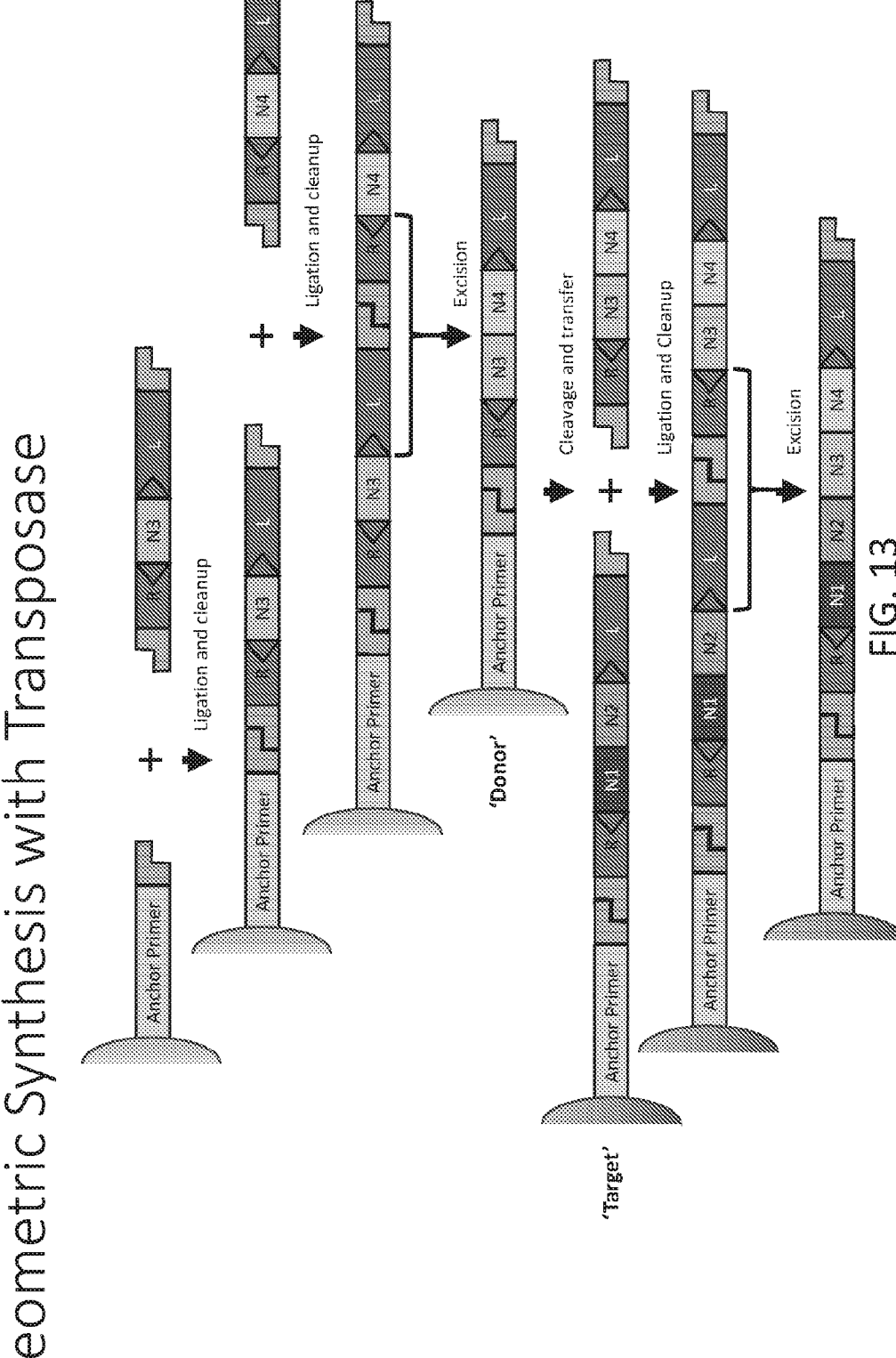
FIG. 13 depicts double stranded DNA geometric synthesis mediated by ligation and the activity of precisely excising transposases. 1) Ligation of an N-mer carrying inverse transposable element onto anchor primers is followed by reaction cleanup. 2) A second N-mer carrying inverse transposable element is then ligated to the extending NA chain on the solid support followed by cleanup. 3) Treatment of the extending NA chain with transposase leads to the excision of the intervening sequence between the two N-mer sequences. 3) The ligated, excised NA chain can be released from the beads by a RE reaction and can then serve as a 'donor' for a subsequent ligation reaction. 4) Cycles of cleavage and transfer, ligation and cleanup, followed by excision using appropriate 'donors' and 'targets' will lead eventually to the desired NA sequence.
Figure 14:
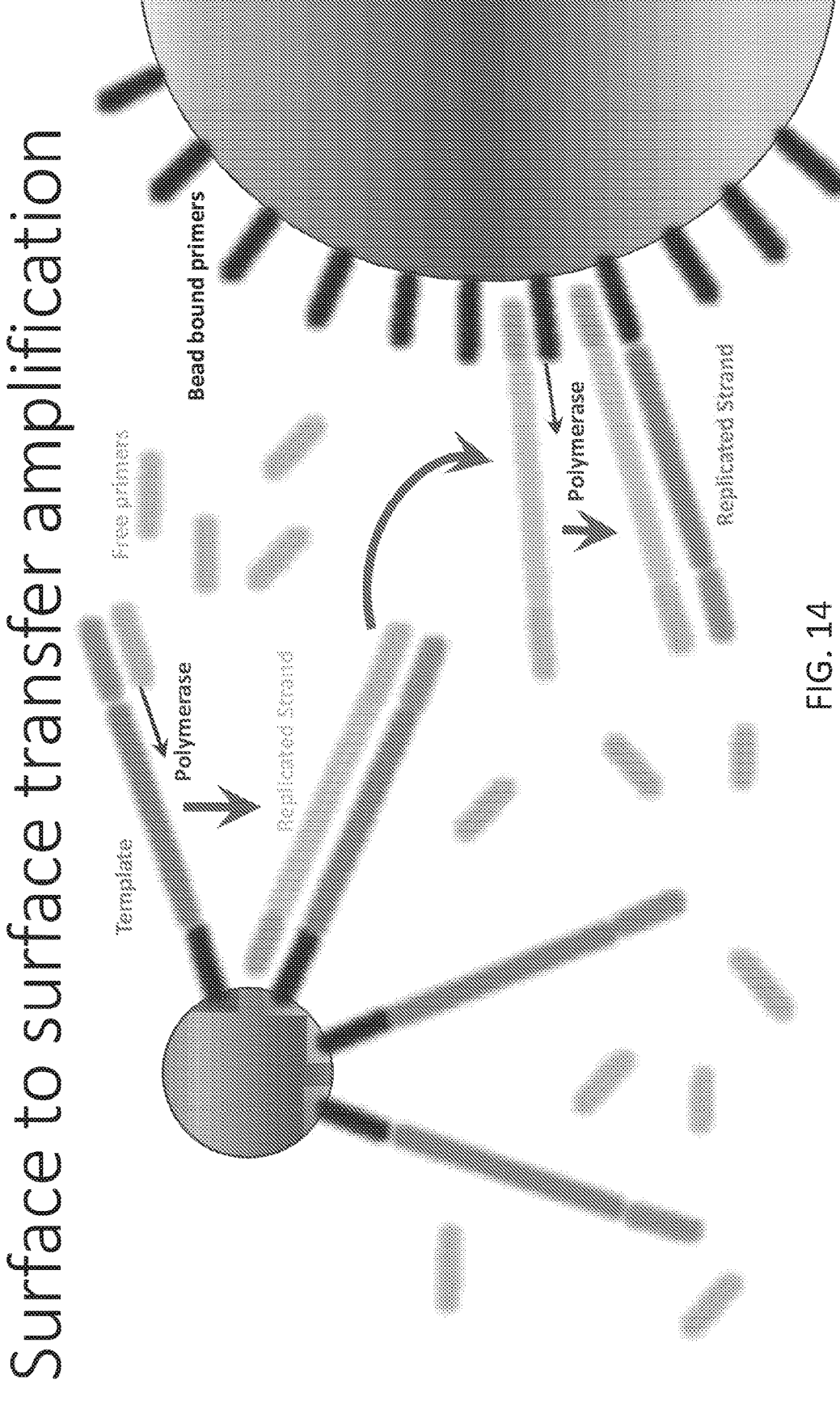
FIG. 14 depicts compositions and methods for the amplification of NAs by surface to surface transfer amplification. In this example, the template (dark pink with a dark green end and a black end) is brought into the reaction on a bead (small blue circle) (donor surface). The template NA molecules (dark pink) bear unique sequences at the proximal end (near the bead, depicted in black) and distal end (away from the bead, depicted in dark green). In the case of a geometric synthesis reaction, the distal unique sequence (dark green) may be ligated onto the template sequence. These sequences are used as targets for primers: black primers attached to the beads (small blue circle and large blue semi-circle), which in the case of geometric synthesis would essentially be the anchor primers, and light green primers that are free in solution. In the amplification reaction, which can be mediated by either PCR or RPA, a polymerase (purple arrow) synthesizing from a template bound free primer (light green) will make a reverse complement copy (light pink with a light green end and a grey end) of the template NA. The replicated strand (copy) released, for example, during the melt phase of a PCR cycle, can then hybridize to acceptor-surface (large blue semi-circle) (acceptor surface) bound primers. The copy strands then serve as templates for new generation of original NA molecules mediated by polymerase synthesizing from surface-bound primers (black).

FIG. 13 shows a schematic overview of a geometric transposase method of the present disclosure.

In a geometric transposase method, step (10) can be repeated until the desired nucleic acid fragment has been synthesized. The desired nucleic acid fragment can then be released from the anchor primer to which it is ligated.

Geometric 3',5' Co-Synthesis Method

Figure 10:
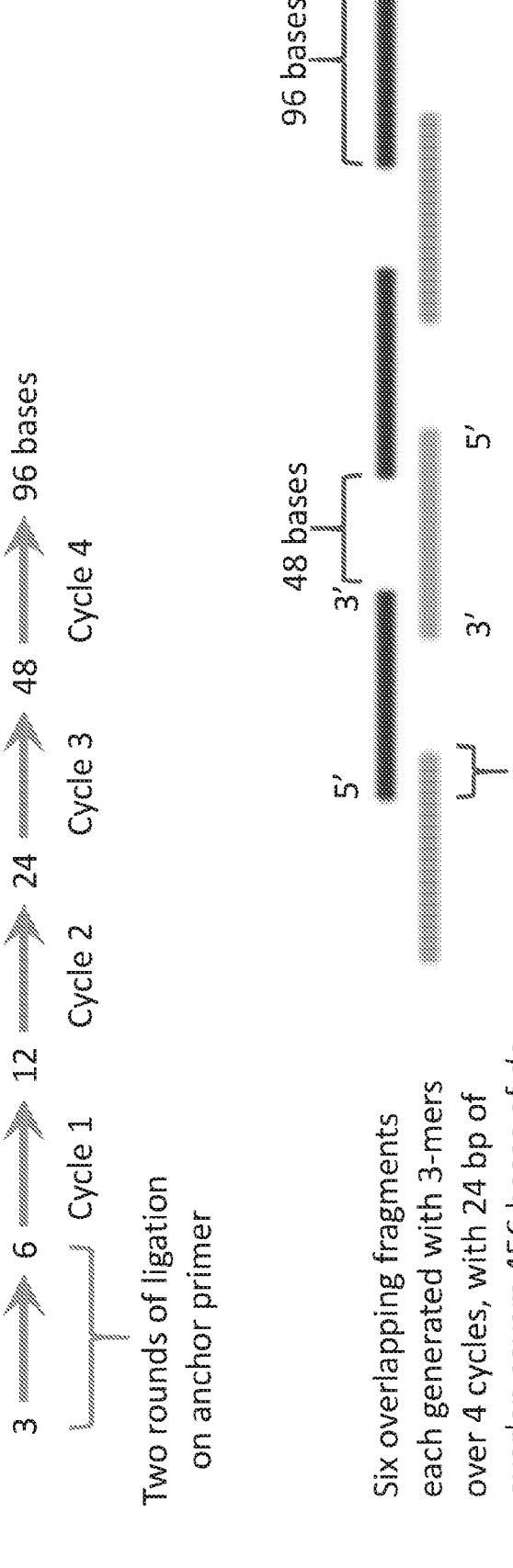
FIG. 10. Size of N-mer can be varied. In 4 cycles 3-mers will generate 96 bases, 4-mers->128 bases and 5-mers->160 bases. Number and length of fragments as well as the size of overlap can be varied. In this example with 6 fragments, 96 bases each and 24 bp overlap, the resulting product would be 456 by long, 160 base fragments and 24 bp overlap would yield an 840 bp product.

The present disclosure provides a geometric 3',5' co-synthesis method. A geometric 3',5' co-synthesis method comprises the use of a set of overlapping nucleic acid fragments, as described above. The bottom panel of FIG. 10 shows a set of six overlapping nucleic acid fragments.

Figure 11:
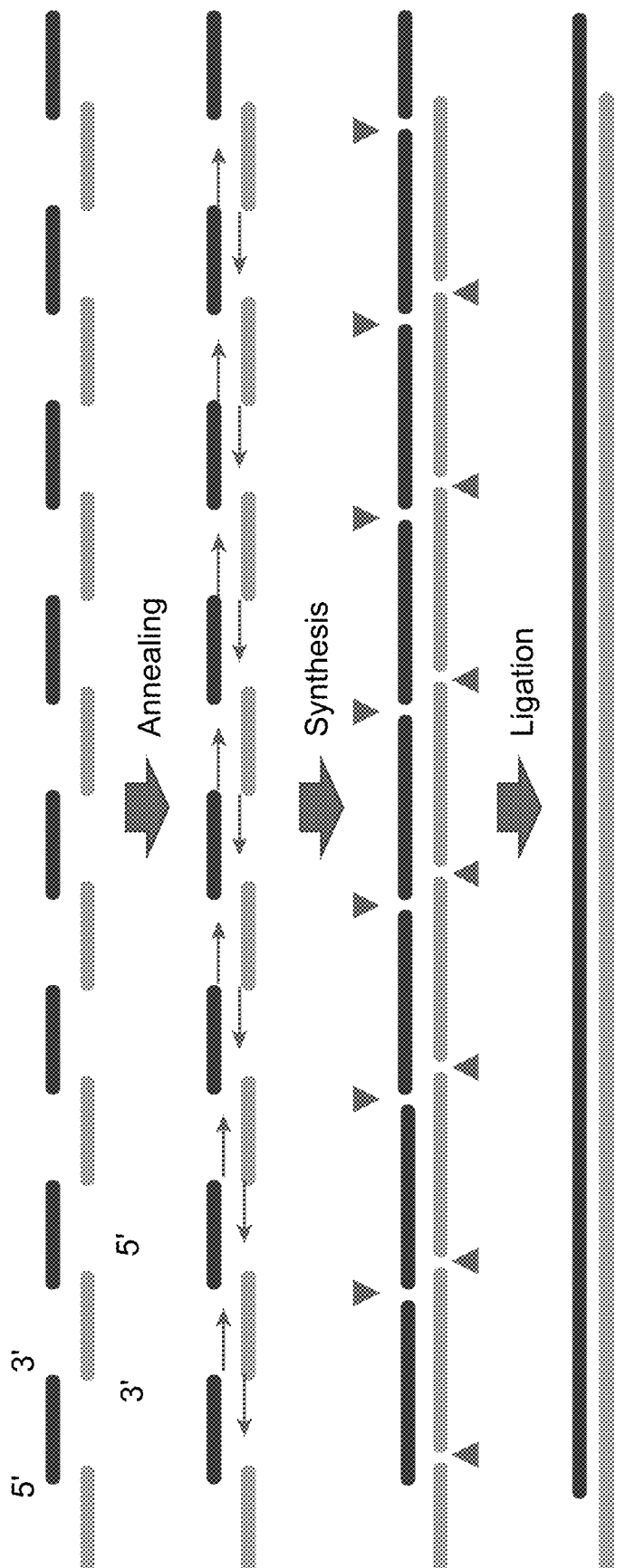
FIG. 11 depicts accelerated long, fast NA synthesis using a mixed 3', 5' co-synthesis with DNA polymerase filling and ligation. In this example, an annealing reaction is carried out with 16 partially overlapping complementary fragments. In a subsequent polymerase reaction, each overlapping 3' end is extended. Finally, in a ligase reaction the breaks between fragments are resolved.

The top panel of FIG. 11 shows a set of 16 overlapping nucleic acid fragments. A geometric 3',5' co-synthesis method can comprise:

1) annealing the overlapping set of nucleic acid fragments together;

2) performing polymerase extension reactions to extend the 3' end of each of the annealed nucleic acid fragments;

3) ligating the extended fragments from step (2) together.

FIG. 11 shows a schematic overview of a geometric 3',5' co-synthesis method.

In a geometric 3',5' co-synthesis method, the set of overlapping nucleic acid fragments can be generated using any method of the present disclosure, including but not limited to, a geometric transposase method of the present disclosure, a 3' extension geometric synthesis method of the present disclosure, a 5' extension geometric synthesis method or any combination thereof.

5' Modular Linear Synthesis Method

The present disclosure also provides a 5' modular linear synthesis method. FIG. 18 depicts a schematic overview of the 5' modular linear synthesis method of the present disclosure. In a 5' modular linear synthesis method, an anchor primer is first attached to a solid support, either directly or indirectly, via the 3' terminus of the anchor primer. After the anchor primer is attached, the next step of the 5' modular synthesis method is to ligate the 3' terminus of an N-mer of the present disclosure to the 5' terminus of the anchor primer attached to the solid support. This step is shown in panel A of FIG. 18, where an N-mer labeled "A" is ligated onto an anchor primer referred to as a "T7 Anchor". Following the first ligation step, any optional protecting groups on the 5' terminus of the ligated N-mer can be removed prior to the next ligation step.

The method continues with the ligation of the 3' terminus of a second N-mer to the 5' end of the ligated first N-mer. This step is shown in panel B of FIG. 18, where an N-mer labeled "B" is ligated onto the "A" N-mer. Following this second ligation step, any optional protecting groups on the 5' terminus of the newly ligated N-mer can be removed prior to the next ligation step.

The method continues with the ligation of the 3' terminus of a third N-mer to the 5' end of the ligated second N-mer. This step is shown in panel C of FIG. 18, where an N-mer labeled "C" is ligated onto the "B" N-mer. Following this third ligation step, any optional protecting groups on the 5' terminus of the newly ligated N-mer can be removed prior to the next ligation step.

The method continues with the ligation of the 3' terminus of a fourth N-mer to the 5' end of the ligated third N-mer. This step is shown in panel D of FIG. 18, where an N-mer labeled "D" is ligated onto the "C" N-mer.

In some aspects, the ligation steps in the 5' modular linear synthesis method can be repeated as many times as necessary using the appropriate N-mers to generate any full length nucleotide sequence.

3' Modular Linear Synthesis Method

The present disclosure also provides a 3' modular linear synthesis method. In a 3' modular linear synthesis method, an anchor primer is first attached to a solid support, either directly or indirectly, via the 5' terminus of the anchor primer. After the anchor primer is attached, the next step of the 3' modular synthesis method is to ligate the 5' terminus of an N-mer of the present disclosure to the 3' terminus of the anchor primer attached to the solid support. Following the first ligation step, any optional protecting groups on the 3' terminus of the ligated N-mer can be removed prior to the next ligation step.

The method continues with the ligation of the 5' terminus of a second N-mer to the 3' end of the ligated first N-mer. Following this second ligation step, any optional protecting groups on the 3' terminus of the newly ligated N-mer can be removed prior to the next ligation step.

The method continues with the ligation of the 5' terminus of a third N-mer to the 3' end of the ligated second N-mer.

Following this third ligation step, any optional protecting groups on the 3' terminus of the newly ligated N-mer can be removed prior to the next ligation step.

The method continues with the ligation of the 5' terminus of a fourth N-mer to the 3' end of the ligated third N-mer.

In some aspects, the ligation steps in the 3' modular linear synthesis method can be repeated as many times as necessary using the appropriate N-mers to generate any full length nucleotide sequence.

General Methods

In all methods of the present disclosure, N-mers and/or anchor primers can comprise a deoxyribose 5' (DNA) terminus and a ribose 3' (RNA) terminus. N-mers and/or anchor primers that comprise deoxyribose 5' (DNA) termini and a ribose 3' (RNA) termini exhibit increased ligation efficiencies as compared to the ligation of two fragments both 5' and 3' deoxyribose (DNA) termini or both 5' and 3' ribose (RNA) termini.

In all methods of the present disclosure, following any ligation reaction, any ligated N-mers can be adenylated at the 5' terminus. The N-mers can be adenylated using methods known in the art, including, but not limited to, treating the N-mers with Mth RNA ligase.

In all methods of the present disclosure, following any ligation reaction, any ligated N-mers can be phosphorylated at the 5' terminus. The N-mers can be phosphorylated using methods known in the art, including, but not limited to, treating the N-mers with T4 polynucleotide kinase.

In all methods of the present disclosure, un-ligated N-mers and unattached anchor primers can be digested and removed using an exonuclease. In some aspects of 5' extension methods of the present disclosure, a 5' to 3' exonuclease can be used to digest and remove un-ligated N-mers and unattached anchor primers. In some aspects of 3' extension methods of the present disclosure, a 3' to 5' exonuclease can be used to digest and remove un-ligated N-mers In all methods of the present disclosure, prior to any exonuclease digestion reaction, the N-mers and/or ligated N-mers to be digested can be de-adenylated. De-adenylation can be accomplished using methods known in the art, including, but not limited to, treating the N-mers with *S. cerevisiae* 5' deadenylase.

In all methods of the present disclosure, protecting groups located on the 5' or 3' end of an N-mer can be removed using methods known in the art. These methods can include, but are not limited to, acid and base washing steps.

EXAMPLES

Example 1: Ligation of N-Mers Comprising XNA

The following is an example that demonstrates that N-mers comprising XNA can be ligated in the methods of the present disclosure.

First, a biotinylated anchor primer comprising a 5' $PO_4$ group, followed by a DNA spacer sequence, followed by a TEG spacer linked to a biotin moiety, was attached to streptavidin-coated, magnetic beads. The DNA spacer comprised an internal fluorescein labeled dT and the sequence TAGTAGCGAACTACTGGACCCG-Fluor-T-CCTTCACC (SEQ ID NO: 12). The biotinylated anchor primer was operably linked to the streptavidin-coated, magnetic beads (MyOne Dynal, Invitrogen) by incubating 500 pmols of the anchor primer for each 1 mg of beads used, such that the concentration of anchor primer in the reaction was 1 µM and the concentration of beads was 2 mg/ml. The incubation buffer comprised phosphate-buffered saline (PBS) with 0.01% TWEEN20. The reactions were incubated for 30 minutes at room temperature and vortexed. After incubation, the beads were washed three times with 0.7 ml of wash buffer comprising (20 mM HEPES, 0.01% TWEEN20, pH 8.0). The beads were then suspended in the wash buffer at a concentration of 10 mg/ml and stored at 4° C. until further use.

In this experiment, 3 different N-mers were tested. The sequence of the N-mers is shown in Table 2. The Chimera N-mer comprised a terminal 3' ribonucleotide (rC). The LNA chimera N-mer comprised an LNA (+T) and a terminal 3' ribonucleotide (rC). The Internal Cy3 N-mer comprised an internal Cy3 label.

TABLE 2

Sequences of N-mers

| N-mer Name | Sequence | SEQ ID NO: |
|---|---|---|
| Chimera N-mer | GGAGACTCCTGGGACGArC | 79 |
| LNA chimera N-mer | GGAGAC + TCCTGGGACGArC | SO |
| Internal Cy-3 N-mer | GGAGACiCy3TCCTGGGACGArC | 81 |

+ = denotes Locked Nucleic Acid (LNA); iCy3 = denotes internal Cy3 fluoro-phore.

In a first ligation reaction, the 3' terminus of the Chimera N-mer was ligated to the 5' terminus of the bead-bound anchor primer. In a second ligation reaction, the 3' terminus of the LNA chimera N-mer was ligated to the 5' terminus of the bead-bound anchor primer. In a third ligation reaction, the 3' terminus of the Internal Cy3 N-mer was ligated to the 5' terminus of the bead-bound anchor primer.

For the ligation reactions, 2.5 µM of anchor primer/beads were incubated with 0.5 µM of the respective fragment (A or C) in the presence of 1.5 units/µl of T4 RNA ligase 1 in a buffer comprising 20 mM HEPES pH 8.0, 50 mM Potassium Acetate. 10 mM Magnesium Acetate, 0.1 mg/ml BSA and 0.01% TWEEN 20. The ligation reactions were incubated at 21° C. for 30 minutes. After the ligation reaction, the beads were washed using a magnetic separator by washing three times with 0.7 ml of a buffer comprising 20 mM HEPES pH 8.0 and 0.01% TWEEN 20, followed by a wash with 0.7 ml of 0.01% TWEEN 20.

FIG. 17 shows polyacrylamide gel analysis of these ligation reactions. The contents of each lane of the gel are described in Table 3. FIG. 17 shows that N-mers comprising XNA can be ligated using the methods of the present disclosure.

TABLE 3

Lane descriptions

| Lane # | Description |
|---|---|
| 1 | 100 bp marker |
| 2 | Anchor primer |
| 3 | Anchor primer + Ligase |
| 4 | Anchor primer + Chimera N-mer ligation reaction |
| 5 | Anchor primer + LNA Chimera N-mer ligation reaction |
| 6 | Anchor primer + Internal Cy3 chimera ligation reaction |

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

OTHER ASPECTS

While particular aspects of the present disclosure have been illustrated and described, various other changes and modifications can be made without departing from the spirit and scope of the present disclosure. The scope of the appended claims includes all such changes and modifications that are within the scope of the present disclosure.

Any of the above aspects can be combined with any other aspect.

What is claimed is:

1. A method comprising:

a) contacting at least one first plurality of solid supports and at least one first plurality of anchor primers, under conditions that allow for the attachment of a 3' terminus of at least one anchor primer of the at least one first plurality of anchor primers to at least one solid support of the at least one first plurality of solid supports to produce at least one first anchor primer-substrate complex;

b) contacting the at least one first anchor primer-substrate complex and at least one first plurality of N-mers under conditions that append a 3' terminus of at least one N-mer of the at least one first plurality of N-mers to a 5' terminus of the at least one first anchor primer-substrate to produce at least one first extended anchor primer-substrate complex;

c) contacting the at least one first extended anchor primer-substrate complex and at least one second plurality of N-mers under conditions that append a 3' terminus of at least one N-Mer of the at least one second plurality of N-mers to a 5' terminus of the at least one first extended anchor primer-substrate complex to produce at least one first donor complex;

d) contacting at least one second plurality of solid supports and at least one second plurality of anchor primers, under conditions that allow for the attachment of a 3' terminus of at least one anchor primer of the at least one second plurality of anchor primers to at least one solid support of the at least one second plurality of solid supports to produce at least one second anchor primer-substrate complex;

e) contacting the at least one second anchor primer-substrate complex and at least one third plurality of N-mers under conditions that append a 3' terminus of at least one N-mer of the at least one third plurality of N-mers to a 5' terminus of the at least one second anchor primer-substrate to produce at least one second extended anchor primer-substrate complex;

f) contacting the at least one second extended anchor primer-substrate complex and at least one fourth plurality of N-mers under conditions that append a 3' terminus of at least one N-mer of the at least one fourth plurality of N-mers to a 5' terminus of the at least one second extended anchor primer-substrate complex to produce at least one first target complex;

g) releasing at least one composition comprising the at least one N-mer of the at least one first plurality of N-mers and the at least one N-mer of the at least one second plurality of N-mers from the at least one first donor complex to produce at least one released intermediate complex; and h) contacting the at least one first target complex and the at least one released intermediate complex under conditions that append a 3' terminus of the at least one released intermediate complex to a 5' terminus of the at least one target complex to produce at least one first extended target complex, wherein at least one N-mer comprises at least one XNA, wherein the anchor primers of the first and second pluralities of anchor primers comprise deoxyribose 5' (DNA) terminus, and wherein at least one of the N-mers comprise a length of 3 to 5 nucleotides and the first, second, third and fourth pluralities of N-mers are chimeric N-mers comprising a deoxyribose 5' (DNA) terminus and a ribose 3' (RNA) terminus.

2. The method of claim 1, wherein appending comprises an enzymatic ligation under conditions that allow for ligase activity.

3. The method of claim 2, wherein the enzymatic ligation comprises T4 RNA ligase activity.

4. The method of claim 1, further comprising, after production of the at least one first anchor primer-substrate complex, or the at least one second anchor primer-substrate complex, removing at least one unattached anchor primer.

5. The method of claim 4, wherein removing the at least one unattached anchor primer comprises the use of an exonuclease, wherein the exonuclease comprises a 5' to 3' specific exonuclease, wherein the 5' to 3' specific exonuclease cannot digest nucleic acid molecules comprising a 5'—OH group.

6. The method of claim 1, further comprising, after production of the at least one first extended anchor primer-substrate complex, the at least one first donor complex, the at least one second extended anchor primer-substrate complex, the at least one first target complex or the at least one first extended target complex, removing at least one un-appended N-mer.

7. The method of claim 6, wherein removing the at least one un-appended N-mer comprises the use of an exonuclease, wherein the exonuclease comprises a 5' to 3' specific exonuclease, wherein the 5' to 3' specific exonuclease cannot digest nucleic acid molecules comprising a 5'—OH group.

8. The method of claim 1, wherein the at least one first plurality of N-mers, the at least one second plurality of N-mers, the at least one third plurality of N-mers, the at least one fourth plurality of N-mers or any combination thereof comprise(s) at least one N-mer comprising an OH group at the 3' terminus and the 5' terminus of the N-mer.

9. The method of claim 8, further comprising, after production of the at least one first extended anchor primer-substrate complex and before contacting the at least one first extended anchor primer-substrate complex with at least one second plurality of N-mers, appending a $PO_4$ group to the 5' end of at least one N-mer of the at least one first plurality of N-mers.

10. The method of claim 8, further comprising, after producing the at least one second extended anchor primer-substrate complex and before contacting the at least one second extended anchor primer-substrate complex and at least one fourth plurality of N-mers, appending a $PO_4$ group to the 5' end of at least one N-mer of the at least one third plurality of N-mers.

11. The method of claim 8, further comprising, prior to contacting the at least one first target complex and the at least one released intermediate complex, appending a $PO_4$ group to the 5' end of at least one N-mer of the at least one fourth plurality of N-mers.

12. The method of claim 1, wherein the at least one first plurality of N-mers, the at least one second plurality of N-mers, the at least one third plurality of N-mers, the at least one fourth plurality of N-mers or any combination thereof comprises at least one N-mer comprising an OH group at the 3' terminus and a $PO_4$ group at the 5' terminus of the N-mer.

13. The method of claim 12, wherein the $PO_4$ group is operably-linked to a protecting group.

14. The method of claim 13, further comprising, after production of the at least one first extended anchor primer-substrate complex and before the production of the at least one first donor complex, removing the protecting group from the at least one first extended anchor primer-substrate complex.

15. The method of claim 13, further comprising, after production of the at least one second extended anchor primer-substrate complex and before the production of the at least one first target complex, removing the protecting group from the at least one second extended anchor primer-substrate complex.

16. The method of claim 13, further comprising, before production of the at least one first extended target complex, removing the protecting group from the at least one first target complex.

17. The method of claim 12, further comprising, after production of the at least one first extended anchor primer-substrate complex and before the production of the at least one first donor complex, adenylating the 5' terminus of the at least one first extended anchor primer-substrate complex.

18. The method of claim 12, further comprising, after production of the at least one second extended anchor primer-substrate complex and before the production of the at least one first target complex, adenylating the 5' terminus of the at least one second extended anchor primer-substrate complex.

19. A nucleic acid sequence produced according to the method of claim 1.

20. The method of claim 1, further comprising selecting a library of N-mers comprising one or more of the first, second, third, and fourth pluralities of N-mers.

* * * * *

SEQUENCE LISTING

<160> NUMBER OF SEQ ID NOS: 81

<210> SEQ ID NO 1
<211> LENGTH: 168
<212> TYPE: DNA
<213> ORGANISM: Aequorea victoria

<400> SEQUENCE: 1
tacacacgaa taaaagataa caaagatgag taaaggagaa gaacttttca ctggagttgt        60
cccaattctt gttgaattag atggcgatgt taatgggcaa aaattctctg tcagtggaga       120
gggtgaaggt gatgcaacat acggaaaact tacccttaaa tttatttg                    168

<210> SEQ ID NO 2
<211> LENGTH: 21
<212> TYPE: DNA
<213> ORGANISM: Artificial Sequence
<220> FEATURE:
<223> OTHER INFORMATION: N-mer

<400> SEQUENCE: 2
tacacacgaa taaaagataa c                                                   21

<210> SEQ ID NO 3
<211> LENGTH: 21
<212> TYPE: DNA
<213> ORGANISM: Artificial Sequence
<220> FEATURE:
<223> OTHER INFORMATION: N-mer

<400> SEQUENCE: 3
acttttcact ggagttgtcc c                                                   21

<210> SEQ ID NO 4
<211> LENGTH: 21
<212> TYPE: DNA
<213> ORGANISM: Artificial Sequence
<220> FEATURE:
<223> OTHER INFORMATION: N-mer

<400> SEQUENCE: 4
cgatgttaat gggcaaaaat t                                                   21

<210> SEQ ID NO 5
<211> LENGTH: 21
<212> TYPE: DNA
<213> ORGANISM: Artificial Sequence
<220> FEATURE:
<223> OTHER INFORMATION: N-mer

<400> SEQUENCE: 5
aggtgatgca acatacggaa a                                                   21

<210> SEQ ID NO 6
<211> LENGTH: 21
<212> TYPE: DNA
<213> ORGANISM: Artificial Sequence
<220> FEATURE:
<223> OTHER INFORMATION: N-mer

<400> SEQUENCE: 6
aaagatgagt aaaggagaag a                                                   21

<210> SEQ ID NO 7
<211> LENGTH: 21

-continued

```
<212> TYPE: DNA
<213> ORGANISM: Artificial Sequence
<220> FEATURE:
<223> OTHER INFORMATION: N-mer

<400> SEQUENCE: 7
aattcttgtt gaattagatg g                                           21

<210> SEQ ID NO 8
<211> LENGTH: 21
<212> TYPE: DNA
<213> ORGANISM: Artificial Sequence
<220> FEATURE:
<223> OTHER INFORMATION: N-mer

<400> SEQUENCE: 8
ctctgtcagt ggagagggtg a                                           21

<210> SEQ ID NO 9
<211> LENGTH: 21
<212> TYPE: DNA
<213> ORGANISM: Artificial Sequence
<220> FEATURE:
<223> OTHER INFORMATION: N-mer

<400> SEQUENCE: 9
acttaccctt aaatttattt g                                           21

<210> SEQ ID NO 10
<211> LENGTH: 16
<212> TYPE: DNA
<213> ORGANISM: Artificial Sequence
<220> FEATURE:
<223> OTHER INFORMATION: Anchor primer

<400> SEQUENCE: 10
gatatcgagt cttaag                                                 16

<210> SEQ ID NO 11
<211> LENGTH: 16
<212> TYPE: DNA
<213> ORGANISM: Artificial Sequence
<220> FEATURE:
<223> OTHER INFORMATION: Short reverse complementary oligonucleotide

<400> SEQUENCE: 11
ctatagctca gaattc                                                 16

<210> SEQ ID NO 12
<211> LENGTH: 31
<212> TYPE: DNA
<213> ORGANISM: Artificial Sequence
<220> FEATURE:
<223> OTHER INFORMATION: Anchor primers
<220> FEATURE:
<221> NAME/KEY: misc_feature
<222> LOCATION: (23)..(23)
<223> OTHER INFORMATION: fluorescein-labeled nucleotide

<400> SEQUENCE: 12
tagtagcgaa ctactggacc cgtccttcac c                                31

<210> SEQ ID NO 13
<211> LENGTH: 54
<212> TYPE: DNA
<213> ORGANISM: Artificial Sequence
<220> FEATURE:
```

<223> OTHER INFORMATION: Anchor primer

<400> SEQUENCE: 13
ctctctctct ctctctctct ctctctctct cccttccttt ctctgagtct gtag      54

<210> SEQ ID NO 14
<211> LENGTH: 24
<212> TYPE: DNA
<213> ORGANISM: Artificial Sequence
<220> FEATURE:
<223> OTHER INFORMATION: Short reverse complementary oligonucleotide

<400> SEQUENCE: 14
gggaaggaaa gagactcaga catc      24

<210> SEQ ID NO 15
<211> LENGTH: 52
<212> TYPE: DNA
<213> ORGANISM: Artificial Sequence
<220> FEATURE:
<223> OTHER INFORMATION: Anchor primer

<400> SEQUENCE: 15
cttaagactc gatatccctg caggctctct ctctctctct ctctctctct ct      52

<210> SEQ ID NO 16
<211> LENGTH: 24
<212> TYPE: DNA
<213> ORGANISM: Artificial Sequence
<220> FEATURE:
<223> OTHER INFORMATION: Short reverse complementary oligonucleotide

<400> SEQUENCE: 16
gaattctgag ctatagggac gtcc      24

<210> SEQ ID NO 17
<211> LENGTH: 55
<212> TYPE: DNA
<213> ORGANISM: Artificial Sequence
<220> FEATURE:
<223> OTHER INFORMATION: Anchor primer
<220> FEATURE:
<221> NAME/KEY: misc_feature
<222> LOCATION: (1)..(54)
<223> OTHER INFORMATION: deoxyribonucleotide
<220> FEATURE:
<221> NAME/KEY: misc_feature
<222> LOCATION: (55)..(55)
<223> OTHER INFORMATION: ribonucleotide

<400> SEQUENCE: 17
ctctctctct ctctctctct ctctctctct ctctctctct ctctctctct ctctu      55

<210> SEQ ID NO 18
<211> LENGTH: 47
<212> TYPE: DNA
<213> ORGANISM: Artificial Sequence
<220> FEATURE:
<223> OTHER INFORMATION: Anchor primer
<220> FEATURE:
<221> NAME/KEY: modified_base
<222> LOCATION: (2)..(2)
<223> OTHER INFORMATION: I
<220> FEATURE:
<221> NAME/KEY: misc_feature
<222> LOCATION: (2)..(2)
<223> OTHER INFORMATION: n is a, c, g, or t

<400> SEQUENCE: 18

-continued

```
anctctctct ctctctctcc tctctctctc tctctctctc tctctct                47

<210> SEQ ID NO 19
<211> LENGTH: 922
<212> TYPE: DNA
<213> ORGANISM: Aequorea victoria

<400> SEQUENCE: 19
tacacacgaa taaaagataa caaagatgag taaaggagaa gaactttttca ctggagttgt     60 cccaattctt gttgaattag atggcgatgt taatgggcaa aaattctctg tcagtggaga     120
gggtgaaggt gatgcaacat acggaaaact taccccttaaa tttatttgca ctactgggaa     180
gctacctgtt ccatggccaa cacttgtcac tactttctct tatggtgttc aatgctttttc     240 aagatacccca gatcatatga aacagcatga cttttttcaag agtgccatgc ccgaaggtta     300
tgtacaggaa agaactatat tttacaaaga tgacgggaac tacaagacac gtgctgaagt     360
caagtttgaa ggtgataccc ttgttaatag aatcgagtta aaaggtattg atttttaaaga     420 agatggaaac attcttggac acaaaatgga atacaactat aactcacata atgtatacat     480
catggcagac aaaccaaaga atggaatcaa agttaacttc aaaattagac acaacattaa     540
agatggaagc gttcaattag cagaccatta tcaacaaaat actccaattg gcgatggccc     600
tgtcctttta ccagacaacc attacctgtc cacacaatct gccctttcca aagatcccaa     660
cgaaaagaga gatcacatga tccttcttga gtttgtaaca gctgctggga ttacacatgg     720
catggatgaa ctatacaaat aaatgtccag acttccaatt gacactaaag tgtccgaaca     780
attactaaat tctcagggtt cctggttaaa ttcaggctga gactttattt atatatttat     840
agattcatta aaattttatg aataatttat tgatgttatt aatagggggct attttcttat     900 taaataggct actggagtgt at                                              922

<210> SEQ ID NO 20
<211> LENGTH: 21
<212> TYPE: DNA
<213> ORGANISM: Artificial Sequence
<220> FEATURE:
<223> OTHER INFORMATION: N-mer

<400> SEQUENCE: 20
tacacacgaa taaaagataa c                                                21

<210> SEQ ID NO 21
<211> LENGTH: 21
<212> TYPE: DNA
<213> ORGANISM: Artificial Sequence
<220> FEATURE:
<223> OTHER INFORMATION: N-mer

<400> SEQUENCE: 21 actttttcact ggagttgtcc c                                               21

<210> SEQ ID NO 22
<211> LENGTH: 21
<212> TYPE: DNA
<213> ORGANISM: Artificial Sequence
<220> FEATURE:
<223> OTHER INFORMATION: N-mer

<400> SEQUENCE: 22
cgatgttaat gggcaaaaat t                                                21
```

-continued

```
<210> SEQ ID NO 23
<211> LENGTH: 21
<212> TYPE: DNA
<213> ORGANISM: Artificial Sequence
<220> FEATURE:
<223> OTHER INFORMATION: N-mer

<400> SEQUENCE: 23
aggtgatgca acatacggaa a                                                  21

<210> SEQ ID NO 24
<211> LENGTH: 21
<212> TYPE: DNA
<213> ORGANISM: Artificial Sequence
<220> FEATURE:
<223> OTHER INFORMATION: N-mer

<400> SEQUENCE: 24
cactactggg aagctacctg t                                                  21

<210> SEQ ID NO 25
<211> LENGTH: 21
<212> TYPE: DNA
<213> ORGANISM: Artificial Sequence
<220> FEATURE:
<223> OTHER INFORMATION: N-mer

<400> SEQUENCE: 25
tactttctct tatggtgttc a                                                  21

<210> SEQ ID NO 26
<211> LENGTH: 21
<212> TYPE: DNA
<213> ORGANISM: Artificial Sequence
<220> FEATURE:
<223> OTHER INFORMATION: N-mer

<400> SEQUENCE: 26
tcatatgaaa cagcatgact t                                                  21

<210> SEQ ID NO 27
<211> LENGTH: 21
<212> TYPE: DNA
<213> ORGANISM: Artificial Sequence
<220> FEATURE:
<223> OTHER INFORMATION: N-mer

<400> SEQUENCE: 27
aggttatgta caggaaagaa c                                                  21

<210> SEQ ID NO 28
<211> LENGTH: 21
<212> TYPE: DNA
<213> ORGANISM: Artificial Sequence
<220> FEATURE:
<223> OTHER INFORMATION: N-mer

<400> SEQUENCE: 28
gaactacaag acacgtgctg a                                                  21

<210> SEQ ID NO 29
<211> LENGTH: 21
<212> TYPE: DNA
<213> ORGANISM: Artificial Sequence
<220> FEATURE:
<223> OTHER INFORMATION: N-mer
```

-continued

```
<400> SEQUENCE: 29
ccttgttaat agaatcgagt t                                                21

<210> SEQ ID NO 30
<211> LENGTH: 21
<212> TYPE: DNA
<213> ORGANISM: Artificial Sequence
<220> FEATURE:
<223> OTHER INFORMATION: N-mer

<400> SEQUENCE: 30
agatggaaac attcttggac a                                                21

<210> SEQ ID NO 31
<211> LENGTH: 21
<212> TYPE: DNA
<213> ORGANISM: Artificial Sequence
<220> FEATURE:
<223> OTHER INFORMATION: N-mer

<400> SEQUENCE: 31
ctcacataat gtatacatca t                                                21

<210> SEQ ID NO 32
<211> LENGTH: 21
<212> TYPE: DNA
<213> ORGANISM: Artificial Sequence
<220> FEATURE:
<223> OTHER INFORMATION: N-mer

<400> SEQUENCE: 32
aatcaaagtt aacttcaaaa t                                                21

<210> SEQ ID NO 33
<211> LENGTH: 21
<212> TYPE: DNA
<213> ORGANISM: Artificial Sequence
<220> FEATURE:
<223> OTHER INFORMATION: N-mer

<400> SEQUENCE: 33
aagcgttcaa ttagcagacc a                                                21

<210> SEQ ID NO 34
<211> LENGTH: 21
<212> TYPE: DNA
<213> ORGANISM: Artificial Sequence
<220> FEATURE:
<223> OTHER INFORMATION: N-mer

<400> SEQUENCE: 34
tggcgatggc cctgtccttt t                                                21

<210> SEQ ID NO 35
<211> LENGTH: 21
<212> TYPE: DNA
<213> ORGANISM: Artificial Sequence
<220> FEATURE:
<223> OTHER INFORMATION: N-mer

<400> SEQUENCE: 35
cacacaatct gccctttcca a                                                21

<210> SEQ ID NO 36
```

```
<211> LENGTH: 21
<212> TYPE: DNA
<213> ORGANISM: Artificial Sequence
<220> FEATURE:
<223> OTHER INFORMATION: N-mer

<400> SEQUENCE: 36
tcacatgatc cttcttgagt t                                              21

<210> SEQ ID NO 37
<211> LENGTH: 21
<212> TYPE: DNA
<213> ORGANISM: Artificial Sequence
<220> FEATURE:
<223> OTHER INFORMATION: N-mer

<400> SEQUENCE: 37
acatggcatg gatgaactat a                                              21

<210> SEQ ID NO 38
<211> LENGTH: 21
<212> TYPE: DNA
<213> ORGANISM: Artificial Sequence
<220> FEATURE:
<223> OTHER INFORMATION: N-mer

<400> SEQUENCE: 38
aattgacact aaagtgtccg a                                              21

<210> SEQ ID NO 39
<211> LENGTH: 21
<212> TYPE: DNA
<213> ORGANISM: Artificial Sequence
<220> FEATURE:
<223> OTHER INFORMATION: N-mer

<400> SEQUENCE: 39
ttcctggtta aattcaggct g                                              21

<210> SEQ ID NO 40
<211> LENGTH: 21
<212> TYPE: DNA
<213> ORGANISM: Artificial Sequence
<220> FEATURE:
<223> OTHER INFORMATION: N-mer

<400> SEQUENCE: 40
agattcatta aaattttatg a                                              21

<210> SEQ ID NO 41
<211> LENGTH: 21
<212> TYPE: DNA
<213> ORGANISM: Artificial Sequence
<220> FEATURE:
<223> OTHER INFORMATION: N-mer

<400> SEQUENCE: 41
taggggctat tttcttatta a                                              21

<210> SEQ ID NO 42
<211> LENGTH: 21
<212> TYPE: DNA
<213> ORGANISM: Artificial Sequence
<220> FEATURE:
<223> OTHER INFORMATION: N-mer

<400> SEQUENCE: 42
```
aaagatgagt aaaggagaag a                                                  21

<210> SEQ ID NO 43
<211> LENGTH: 21
<212> TYPE: DNA
<213> ORGANISM: Artificial Sequence
<220> FEATURE:
<223> OTHER INFORMATION: N-mer

<400> SEQUENCE: 43
aattcttgtt gaattagatg g                                                  21

<210> SEQ ID NO 44
<211> LENGTH: 21
<212> TYPE: DNA
<213> ORGANISM: Artificial Sequence
<220> FEATURE:
<223> OTHER INFORMATION: N-mer

<400> SEQUENCE: 44
ctctgtcagt ggagagggtg a                                                  21

<210> SEQ ID NO 45
<211> LENGTH: 21
<212> TYPE: DNA
<213> ORGANISM: Artificial Sequence
<220> FEATURE:
<223> OTHER INFORMATION: N-mer

<400> SEQUENCE: 45
acttaccctt aaatttattt g                                                  21

<210> SEQ ID NO 46
<211> LENGTH: 21
<212> TYPE: DNA
<213> ORGANISM: Artificial Sequence
<220> FEATURE:
<223> OTHER INFORMATION: N-mer

<400> SEQUENCE: 46
tccatggcca acacttgtca c                                                  21

<210> SEQ ID NO 47
<211> LENGTH: 21
<212> TYPE: DNA
<213> ORGANISM: Artificial Sequence
<220> FEATURE:
<223> OTHER INFORMATION: N-mer

<400> SEQUENCE: 47
atgcttttca agatacccag a                                                  21

<210> SEQ ID NO 48
<211> LENGTH: 21
<212> TYPE: DNA
<213> ORGANISM: Artificial Sequence
<220> FEATURE:
<223> OTHER INFORMATION: N-mer

<400> SEQUENCE: 48
tttcaagagt gccatgcccg a                                                  21

<210> SEQ ID NO 49
<211> LENGTH: 21
<212> TYPE: DNA

<213> ORGANISM: Artificial Sequence
<220> FEATURE:
<223> OTHER INFORMATION: N-mer

<400> SEQUENCE: 49
tatattttac aaagatgacg g                                                                              21

<210> SEQ ID NO 50
<211> LENGTH: 21
<212> TYPE: DNA
<213> ORGANISM: Artificial Sequence
<220> FEATURE:
<223> OTHER INFORMATION: N-mer

<400> SEQUENCE: 50
agtcaagttt gaaggtgata c                                                                              21

<210> SEQ ID NO 51
<211> LENGTH: 21
<212> TYPE: DNA
<213> ORGANISM: Artificial Sequence
<220> FEATURE:
<223> OTHER INFORMATION: N-mer

<400> SEQUENCE: 51
aaaaggtatt gattttaaag a                                                                              21

<210> SEQ ID NO 52
<211> LENGTH: 21
<212> TYPE: DNA
<213> ORGANISM: Artificial Sequence
<220> FEATURE:
<223> OTHER INFORMATION: N-mer

<400> SEQUENCE: 52
caaaatggaa tacaactata a                                                                              21

<210> SEQ ID NO 53
<211> LENGTH: 21
<212> TYPE: DNA
<213> ORGANISM: Artificial Sequence
<220> FEATURE:
<223> OTHER INFORMATION: N-mer

<400> SEQUENCE: 53
ggcagacaaa ccaaagaatg g                                                                              21

<210> SEQ ID NO 54
<211> LENGTH: 21
<212> TYPE: DNA
<213> ORGANISM: Artificial Sequence
<220> FEATURE:
<223> OTHER INFORMATION: N-mer

<400> SEQUENCE: 54
tagacacaac attaaagatg g                                                                              21

<210> SEQ ID NO 55
<211> LENGTH: 21
<212> TYPE: DNA
<213> ORGANISM: Artificial Sequence
<220> FEATURE:
<223> OTHER INFORMATION: N-mer

<400> SEQUENCE: 55
ttatcaacaa aatactccaa t                                                                              21

```
<210> SEQ ID NO 56
<211> LENGTH: 21
<212> TYPE: DNA
<213> ORGANISM: Artificial Sequence
<220> FEATURE:
<223> OTHER INFORMATION: N-mer

<400> SEQUENCE: 56
accagacaac cattacctgt c                                              21

<210> SEQ ID NO 57
<211> LENGTH: 21
<212> TYPE: DNA
<213> ORGANISM: Artificial Sequence
<220> FEATURE:
<223> OTHER INFORMATION: N-mer

<400> SEQUENCE: 57
agatcccaac gaaaagagag a                                              21

<210> SEQ ID NO 58
<211> LENGTH: 21
<212> TYPE: DNA
<213> ORGANISM: Artificial Sequence
<220> FEATURE:
<223> OTHER INFORMATION: N-mer

<400> SEQUENCE: 58
tgtaacagct gctgggatta c                                              21

<210> SEQ ID NO 59
<211> LENGTH: 21
<212> TYPE: DNA
<213> ORGANISM: Artificial Sequence
<220> FEATURE:
<223> OTHER INFORMATION: N-mer

<400> SEQUENCE: 59
caaataaatg tccagacttc c                                              21

<210> SEQ ID NO 60
<211> LENGTH: 21
<212> TYPE: DNA
<213> ORGANISM: Artificial Sequence
<220> FEATURE:
<223> OTHER INFORMATION: N-mer

<400> SEQUENCE: 60
acaattacta aattctcagg g                                              21

<210> SEQ ID NO 61
<211> LENGTH: 21
<212> TYPE: DNA
<213> ORGANISM: Artificial Sequence
<220> FEATURE:
<223> OTHER INFORMATION: N-mer

<400> SEQUENCE: 61
agactttatt tatatattta t                                              21

<210> SEQ ID NO 62
<211> LENGTH: 21
<212> TYPE: DNA
<213> ORGANISM: Artificial Sequence
<220> FEATURE:
```

-continued

<223> OTHER INFORMATION: N-mer

<400> SEQUENCE: 62
ataatttatt gatgttatta a                                          21

<210> SEQ ID NO 63
<211> LENGTH: 19
<212> TYPE: DNA
<213> ORGANISM: Artificial Sequence
<220> FEATURE:
<223> OTHER INFORMATION: N-mer

<400> SEQUENCE: 63
ataggctact ggagtgtat                                             19

<210> SEQ ID NO 64
<211> LENGTH: 37
<212> TYPE: DNA
<213> ORGANISM: Artificial Sequence
<220> FEATURE:
<223> OTHER INFORMATION: Ligation product

<400> SEQUENCE: 64
gatatcgagt cttaagtaca cacgaataaa agataac                         37

<210> SEQ ID NO 65
<211> LENGTH: 37
<212> TYPE: DNA
<213> ORGANISM: Artificial Sequence
<220> FEATURE:
<223> OTHER INFORMATION: Ligation product

<400> SEQUENCE: 65
gatatcgagt cttaagactt ttcactggag ttgtccc                         37

<210> SEQ ID NO 66
<211> LENGTH: 37
<212> TYPE: DNA
<213> ORGANISM: Artificial Sequence
<220> FEATURE:
<223> OTHER INFORMATION: Ligation product

<400> SEQUENCE: 66
gatatcgagt cttaagcgat gttaatgggc aaaaatt                         37

<210> SEQ ID NO 67
<211> LENGTH: 37
<212> TYPE: DNA
<213> ORGANISM: Artificial Sequence
<220> FEATURE:
<223> OTHER INFORMATION: Ligation product

<400> SEQUENCE: 67
gatatcgagt cttaagaggt gatgcaacat acggaaa                         37

<210> SEQ ID NO 68
<211> LENGTH: 58
<212> TYPE: DNA
<213> ORGANISM: Artificial Sequence
<220> FEATURE:
<223> OTHER INFORMATION: Ligation product

<400> SEQUENCE: 68
gatatcgagt cttaagtaca cacgaataaa agataacaaa gatgagtaaa ggagaaga   58

-continued

```
<210> SEQ ID NO 69
<211> LENGTH: 58
<212> TYPE: DNA
<213> ORGANISM: Artificial Sequence
<220> FEATURE:
<223> OTHER INFORMATION: Ligation Product

<400> SEQUENCE: 69
gatatcgagt cttaagactt ttcactggag ttgtcccaat tcttgttgaa ttagatgg        58

<210> SEQ ID NO 70
<211> LENGTH: 58
<212> TYPE: DNA
<213> ORGANISM: Artificial Sequence
<220> FEATURE:
<223> OTHER INFORMATION: Ligation product

<400> SEQUENCE: 70
gatatcgagt cttaagcgat gttaatgggc aaaaattctc tgtcagtgga gagggtga        58

<210> SEQ ID NO 71
<211> LENGTH: 57
<212> TYPE: DNA
<213> ORGANISM: Artificial Sequence
<220> FEATURE:
<223> OTHER INFORMATION: 71

<400> SEQUENCE: 71
gatatcgagt cttaagaggt gatgcaacat acggaaaact tacccttaaa tttattt         57

<210> SEQ ID NO 72
<211> LENGTH: 42
<212> TYPE: DNA
<213> ORGANISM: Artificial Sequence
<220> FEATURE:
<223> OTHER INFORMATION: Released ligation product

<400> SEQUENCE: 72
acttttcact ggagttgtcc caattcttgt tgaattagat gg                         42

<210> SEQ ID NO 73
<211> LENGTH: 41
<212> TYPE: DNA
<213> ORGANISM: Artificial Sequence
<220> FEATURE:
<223> OTHER INFORMATION: Released ligation product

<400> SEQUENCE: 73
aggtgatgca acatacggaa aacttaccct taaatttatt t                          41

<210> SEQ ID NO 74
<211> LENGTH: 100
<212> TYPE: DNA
<213> ORGANISM: Artificial Sequence
<220> FEATURE:
<223> OTHER INFORMATION: Ligation product

<400> SEQUENCE: 74
gatatcgagt cttaagtaca cacgaataaa agataacaaa gatgagtaaa ggagaagaac      60
ttttcactgg agttgtccca attcttgttg aattagatgg                           100

<210> SEQ ID NO 75
<211> LENGTH: 99
<212> TYPE: DNA
<213> ORGANISM: Artificial Sequence
<220> FEATURE:
```

-continued

<223> OTHER INFORMATION: Ligation product

<400> SEQUENCE: 75
gatatcgagt cttaagcgat gttaatgggc aaaaattctc tgtcagtgga gagggtgaag          60
gtgatgcaac atacggaaaa cttaccctta aatttattt                                99

<210> SEQ ID NO 76
<211> LENGTH: 83
<212> TYPE: DNA
<213> ORGANISM: Artificial Sequence
<220> FEATURE:
<223> OTHER INFORMATION: Released ligation product

<400> SEQUENCE: 76
cgatgttaat gggcaaaaat tctctgtcag tggagagggt gaaggtgatg caacatacgg          60
aaaacttacc cttaaattta ttt                                                 83

<210> SEQ ID NO 77
<211> LENGTH: 153
<212> TYPE: DNA
<213> ORGANISM: Artificial Sequence
<220> FEATURE:
<223> OTHER INFORMATION: Ligation product

<400> SEQUENCE: 77
gatatcgagt cttaagtaca cacgaataaa agataacaaa gatgagtaaa ggagaagaac          60
ttttcactgg agttgtccca attcttgttg aattagatgg cgatgttaat gggcaaaaat         120
tctctgtcag tggagagggt gaaggtgatg caa                                      153

<210> SEQ ID NO 78
<211> LENGTH: 167
<212> TYPE: DNA
<213> ORGANISM: Artificial Sequence
<220> FEATURE:
<223> OTHER INFORMATION: Released ligation product

<400> SEQUENCE: 78
tacacacgaa taaaagataa caaagatgag taaaggagaa gaacttttca ctggagttgt          60
cccaattctt gttgaattag atggcgatgt taatgggcaa aaattctctg tcagtggaga         120
gggtgaaggt gatgcaacat acggaaaact accccttaaa tttattt                       167

<210> SEQ ID NO 79
<211> LENGTH: 18
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(17)
<223> OTHER INFORMATION: deoxyribonucleotide
<220> FEATURE:
<221> NAME/KEY: misc_feature
<222> LOCATION: (18)..(18)
<223> OTHER INFORMATION: ribonucleotide

<400> SEQUENCE: 79
ggagactcct gggacgac                                                       18

<210> SEQ ID NO 80
<211> LENGTH: 18
<212> TYPE: DNA
<213> ORGANISM: Artificial Sequence

```
<220> FEATURE:
<223> OTHER INFORMATION: N-mer
<220> FEATURE:
<221> NAME/KEY: misc_feature
<222> LOCATION: (1)..(6)
<223> OTHER INFORMATION: deoxyribonucleotide
<220> FEATURE:
<221> NAME/KEY: misc_feature
<222> LOCATION: (7)..(7)
<223> OTHER INFORMATION: Locked nucleic acid
<220> FEATURE:
<221> NAME/KEY: misc_feature
<222> LOCATION: (8)..(17)
<223> OTHER INFORMATION: deoxyribonucleotide
<220> FEATURE:
<221> NAME/KEY: misc_feature
<222> LOCATION: (18)..(18)
<223> OTHER INFORMATION: ribonucleotide

<400> SEQUENCE: 80
ggagactcct gggacgac                                                18

<210> SEQ ID NO 81
<211> LENGTH: 18
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(5)
<223> OTHER INFORMATION: deoxyribonucleotide
<220> FEATURE:
<221> NAME/KEY: misc_feature
<222> LOCATION: (6)..(7)
<223> OTHER INFORMATION: internal Cy3 linker between
     deoxyribonucleotides
<220> FEATURE:
<221> NAME/KEY: misc_feature
<222> LOCATION: (6)..(7)
<223> OTHER INFORMATION: internal Cy3 linker between
     deoxyribonucleotides
<220> FEATURE:
<221> NAME/KEY: misc_feature
<222> LOCATION: (8)..(17)
<223> OTHER INFORMATION: deoxyribonucleotides
<220> FEATURE:
<221> NAME/KEY: misc_feature
<222> LOCATION: (18)..(18)
<223> OTHER INFORMATION: ribonucleotide

<400> SEQUENCE: 81
ggagactcct gggacgac                                                18
```